US009023823B2

(12) United States Patent
Srivastava

(10) Patent No.: US 9,023,823 B2
(45) Date of Patent: May 5, 2015

(54) MICRO-RNA'S THAT REGULATE MUSCLE CELLS

(71) Applicant: The Board of Regents of the University of Texas System, Austin, TX (US)

(72) Inventor: Deepak Srivastava, Orinda, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/088,956

(22) Filed: Nov. 25, 2013

(65) Prior Publication Data
US 2014/0155460 A1 Jun. 5, 2014

Related U.S. Application Data

(62) Division of application No. 11/397,961, filed on Apr. 4, 2006, now Pat. No. 8,592,384.

(60) Provisional application No. 60/668,187, filed on Apr. 4, 2005.

(51) Int. Cl.
C12N 15/11 (2006.01)
C12N 15/113 (2010.01)

(52) U.S. Cl.
CPC ............ *C12N 15/113* (2013.01); *C12N 15/111* (2013.01); *C12N 2310/14* (2013.01); *C12N 2320/11* (2013.01); *C12N 2330/10* (2013.01)

(58) Field of Classification Search
CPC ........... C12N 15/113; C12N 2310/141; C12N 2310/113; C12N 15/111; C12N 2501/65; C12N 5/0657; C12N 5/0692; C12N 5/0695; C12Q 2525/207; C12Q 2600/178
See application file for complete search history.

(56) References Cited

U.S. PATENT DOCUMENTS

| | | | |
|---|---|---|---|
| 7,229,774 | B2 | 6/2007 | Chinnaiyan et al. |
| 7,232,806 | B2 | 6/2007 | Tuschl et al. |
| 7,390,792 | B2 | 6/2008 | Srivastava et al. |
| 7,718,630 | B2 | 5/2010 | Srivastava et al. |
| 8,592,384 | B2 | 11/2013 | Srivastava |
| 2005/0059005 | A1 | 3/2005 | Tuschl et al. |
| 2005/0074788 | A1 | 4/2005 | Dahlberg et al. |
| 2005/0261218 | A1 | 11/2005 | Esau et al. |
| 2005/0266418 | A1 | 12/2005 | Chen et al. |
| 2006/0019286 | A1 | 1/2006 | Horvitz et al. |
| 2006/0105360 | A1 | 5/2006 | Croce et al. |
| 2006/0185027 | A1 | 8/2006 | Bartel et al. |
| 2006/0246491 | A1 | 11/2006 | Srivastava |
| 2006/0247193 | A1 | 11/2006 | Taira et al. |
| 2006/0252722 | A1 | 11/2006 | Lollo et al. |
| 2006/0265771 | A1 | 11/2006 | Lewis et al. |
| 2007/0003939 | A1 | 1/2007 | Wang et al. |
| 2007/0050146 | A1 | 3/2007 | Bentwich et al. |
| 2007/0054872 | A1 | 3/2007 | Reppen et al. |
| 2007/0065840 | A1 | 3/2007 | Naguibneva et al. |
| 2007/0065844 | A1 | 3/2007 | Golub et al. |
| 2007/0092882 | A1 | 4/2007 | Wang et al. |
| 2007/0099196 | A1 | 5/2007 | Kauppinen et al. |
| 2007/0161004 | A1 | 7/2007 | Brown et al. |
| 2008/0124737 | A1 | 5/2008 | Srivastava et al. |
| 2008/0176766 | A1 | 7/2008 | Brown et al. |
| 2009/0005336 | A1 | 1/2009 | Wang |
| 2009/0053718 | A1 | 2/2009 | Naguibneva et al. |
| 2009/0186414 | A1 | 7/2009 | Srivastava et al. |
| 2010/0292297 | A1* | 11/2010 | Wang et al. ................. 514/44 A |

FOREIGN PATENT DOCUMENTS

| | | |
|---|---|---|
| EP | 1627925 A1 | 2/2006 |
| EP | 1777301 A2 | 4/2007 |
| EP | 1959012 A2 | 8/2008 |
| WO | WO 00/24254 A1 | 5/2000 |
| WO | WO 00/62736 | 10/2000 |
| WO | WO 03/029459 A2 | 4/2003 |
| WO | WO 2004/076622 A2 | 9/2004 |
| WO | WO 2005/013901 A2 | 2/2005 |
| WO | WO 2005/019433 A2 | 3/2005 |
| WO | WO 2005/040419 A1 | 5/2005 |
| WO | WO 2005/078139 A2 | 8/2005 |
| WO | WO 2005/079397 A2 | 9/2005 |
| WO | WO 2005/085280 A2 | 9/2005 |
| WO | WO 2005/103298 A2 | 11/2005 |
| WO | WO 2005/118806 A2 | 12/2005 |
| WO | WO 2006/015389 A2 | 2/2006 |
| WO | WO 2006/025879 A2 | 3/2006 |
| WO | WO 2006/069584 A2 | 7/2006 |
| WO | WO 2006/081284 A2 | 8/2006 |
| WO | WO 2006/107826 A3 | 10/2006 |
| WO | WO 2006/108473 A1 | 10/2006 |
| WO | WO 2006/111512 A1 | 10/2006 |

(Continued)

OTHER PUBLICATIONS

Krützfeldt et al., Silencing of microRNAs in vivo with 'antagomirs', 2005, Nature, vol. 438, pp. 685-689.*
van Rooji et al., A signature pattern of stress-responsive microRNAs that can evoke cardiac hypertrophy and heart failure, 2006, PNAS, vol. 48, pp. 18255-18260.*
Pan et al., miR-1 exacerbates cardiac ischemia-reperfusion injury in mouse models, Nov. 2012, PLOS ONE, vol. 7, issue 11, e50515, pp. 1-9.*
Abrahante et al, "The *Caenorhabditis elegans* hunchback-like gene lin-57/hbl-1 controls developmental time and is regulated by microRNAs," Dev. Cell, 4:625-37, 2003.
Altschul et al., "Gapped BLAST and PSI-BLAST: a new generation of protein database search programs," Nucleic Acids Res., 25:3389-3402.
Brennecke et al., "bantam encodes a developmentally regulated microRNA that controls cell proliferation and regulates the proapoptotic gene hid in *Drosophila*," Cell, 113:25-36, 2003.

(Continued)

*Primary Examiner* — Dana Shin
(74) *Attorney, Agent, or Firm* — Parker Highlander PLLC

(57) ABSTRACT

The present invention describes microRNAs that regulate the differentiation, proliferation and death of cardiac and skeletal muscles cells. These molecules represent unique targets in the developmental pathways of muscle cells. They also can be used as active agents to induce differentiation in progenitor cells, and their down-regulation permits the maintenance and expansion of progenitor cell populations.

17 Claims, 34 Drawing Sheets

(56) References Cited

FOREIGN PATENT DOCUMENTS

| WO | WO 2006/119266 A2 | 11/2006 |
| WO | WO 2006/133022 A2 | 12/2006 |
| WO | WO 2006/137941 A2 | 12/2006 |
| WO | WO 2007/000668 A2 | 1/2007 |
| WO | WO 2007/002375 A2 | 1/2007 |
| WO | WO 2007/016548 A2 | 2/2007 |
| WO | WO 2007/028030 A2 | 3/2007 |
| WO | WO 2007/033023 A2 | 3/2007 |
| WO | WO 2007/042899 A2 | 4/2007 |
| WO | WO 2007/070483 A2 | 6/2007 |
| WO | WO 2007/073737 A1 | 7/2007 |
| WO | WO 2007/081196 A1 | 7/2007 |
| WO | WO 2007/081204 A2 | 7/2007 |
| WO | WO 2007/081680 A2 | 7/2007 |
| WO | WO 2007/103808 A2 | 9/2007 |
| WO | WO 2007/112754 A2 | 10/2007 |
| WO | WO 2008/015028 A1 | 2/2008 |
| WO | WO 2008/042231 A2 | 4/2008 |
| WO | WO 2008/043521 A2 | 4/2008 |
| WO | WO 2008/061537 A2 | 5/2008 |
| WO | WO 2008/147430 A2 | 12/2008 |
| WO | WO 2008/147839 A1 | 12/2008 |
| WO | WO 2008/150897 A2 | 12/2008 |
| WO | WO 2009/026576 A1 | 2/2009 |

OTHER PUBLICATIONS

Bruneau, "Developmental biology: tiny brakes for a growing heart," Nature, 436:181-182, 2005.

Chang et al., "MicroRNAs act sequentially and asymmetrically to control chemosensory laterality in the nematode," Nature, 430:785-9, 2004.

Chen et al., "The role of microRNA-1 and microRNA-133 in skeletal muscle proliferation and differentiation," Nature Genetics, 38:228-233, 2006.

Conboy et al., Notch-mediated restoration of regenerative potential to agend muscle, 2003, Science, vol. 302, pp. 1575-1577.

Doench et al., "siRNAs can function as miRNAs," Genes Dev., 17:438-42, 2003.

Du et al., "Myocardin is a critical serum response factor cofactor in the transcriptional program regulating smooth muscle cell differentiation," Molecular and Cellular Biology, vol. 23: 2427-2437, Apr. 2003.

Gale et al., Haploinsufficiency of delta-like 4 ligand results in embryonic lethality due to major defects in arterial and vascular development, 2004, PNAS, vol. 101, pp. 15949-15954.

GenBank Accesion No. AJ459701 (2002).

Großhans et al., "The temporal patterning microRNA let-7 regulates several transcription factors at the larval to adult transition in C. elegans," Dev. Cell., 8:321-330, 2005.

Haley and Zamore, "Kinetic analysis of the RNAi enzyme complex," Nat. Struct. Mol. Biol., 11:599-606, 2004.

John et al., "Human MicroRNA targets," PLoS Biol., 2:e363, 2004.

Johnston and Hobert, "A microRNA controlling left/right neuronal asymmetry in Caenorhabditis elegans," Nature, 426:845-9, 2003.

Kiriakidou et al., "A combined computational-experimental approach predicts human microRNA targets," Genes Dev., 18:1165-78, 2004.

Kwon et al., "MicroRNA1 influences cardiac differentiation in Drosophila and regulates Notch signaling," Proc. Natl. Acad. Sci. USA, 102:18986-18991, 2005.

Lagos-Quintana et al., "Identification of Tissue-Specific MicroRNAs from Mouse," 12:735-739, 2002.

Lai, "Micro RNAs are complementary to 3' UTR sequence motifs that mediate negative post-transcriptional regulation," Nat. Genet., 30:363-4, 2002.

Lee et al., "An extensive class of small RNAs in Caenorhabditis elegans," Science, 294:862-864, 2001.

Lee et al., "Expression of small interfering RNAs targeted against HIV-1 rev transcripts in human cells," Nat. Biotechnol., 20:500-5, 2002.

Lee et al., "The C. elegans heterochronic gene lin-4 encodes small RNAs with antisense complementarity to lin-14," Cell, 75:843-54, 1993.

Lewis et al., "Conserved seed pairing, often flanked by adenosines, indicates that thousands of human genes are microRNA targets," Cell, 120:15-20, 2005.

Lewis et al., "Prediction of mammalian microRNA targets," Cell, 115:787-98, 2003.

Lim et al., "Microarray analysis shows that some microRNAs downregulate large numbers of target mRNAs," Nature, 433:769-773, 2005.

Miner et al., Skeletal muscle phenotypes initiated by ectopic MyoD in transgenic mouse heart, 1992, Development, vol. 114, pp. 853-860.

Montarras et al., Autonomous differentiation in the mouse myogenic cell line, C2, involves a mutual positive control between insulin-like growth factor II and MyoD, operating as early as at the myoblast stage, 1996, Journal of Cell Science, vol. 109, pp. 551-560.

Moss et al., "The cold shock domain protein LIN-28 controls developmental timing in C. elegans and is regulated by the lin-4 RNA," Cell, 88:637-46, 1997.

Olson, "Interplay between proliferation and differentiation within the myogenic lineage," 1992, Developmental Biology, vol. 154, pp. 261-272.

Poy et al., "A pancreatic islet-specific microRNA regulates insulin secretion," Nature, 432:226-30, 2004.

Rhoades et al., "Prediction of plant microRNA targets," Cell, 110:513-20, 2002.

Shawber et al., Notch signaling inhibits muscle cell differentiation through a CBF1-independent pathway, 1996, Development, vol. 122, pp. 3765-3773.

Sokol et al., "Mesodermally expressed Drosophila microRNA-1 is regulated by Twist and is required in muscles during larval growth," Genes & Development, 19:2343-2354, 2005.

Srivastava et al., "A subclass of bLHL proteins required for cardiac morphogenesis," Science, 270:1995-9, 1995.

Srivastava et al., "Regulation of cardiac mesodermal and neural crest development by the bHLH transcription factor, dHAND," Nat. Genet., 16:154-60, 1997.

Stark et al., "Identification of Drosophila MicroRNA targets," PLoS Biol., 1:E60, 2003.

Vella et al., "The C. elegans microRNA let-7 binds to imperfect let-7 complementary sites from the lin-41 3'UTR," Genes Dev., 18:132-7, 2004.

Wang et al., "Activation of cardiac gene expression by myocardia, a transcriptional cofactor for serum response factor," Cell, 105:851-62, 2001.

Wightman et al., "Posttranscriptional regulation of the heterochronic gene lin-14 by lin-4 mediates temporal pattern formation in C. elegans," Cell, 75:855-62, 1993.

Written Opinion of the International Searching Authority, PCT appl. No. PCT/US2006/012219, 10 pages (Nov. 30, 2006).

Yekta et al., "MicroRNA-directed cleavage of HOXB8 mRNA," Science, 304:594-6, 2004.

Zhao et al., "Serum response factor regulates a muscle-specific microRNA that targets Hand2 during cardiogenesis," Nature, 436:214-220, 2005.

Zheng, Dbl family guanine nucleotide exchange factors, 2001, TRENDS in Biochemical Sciences, vol. 26, pp. 724-732.

* cited by examiner

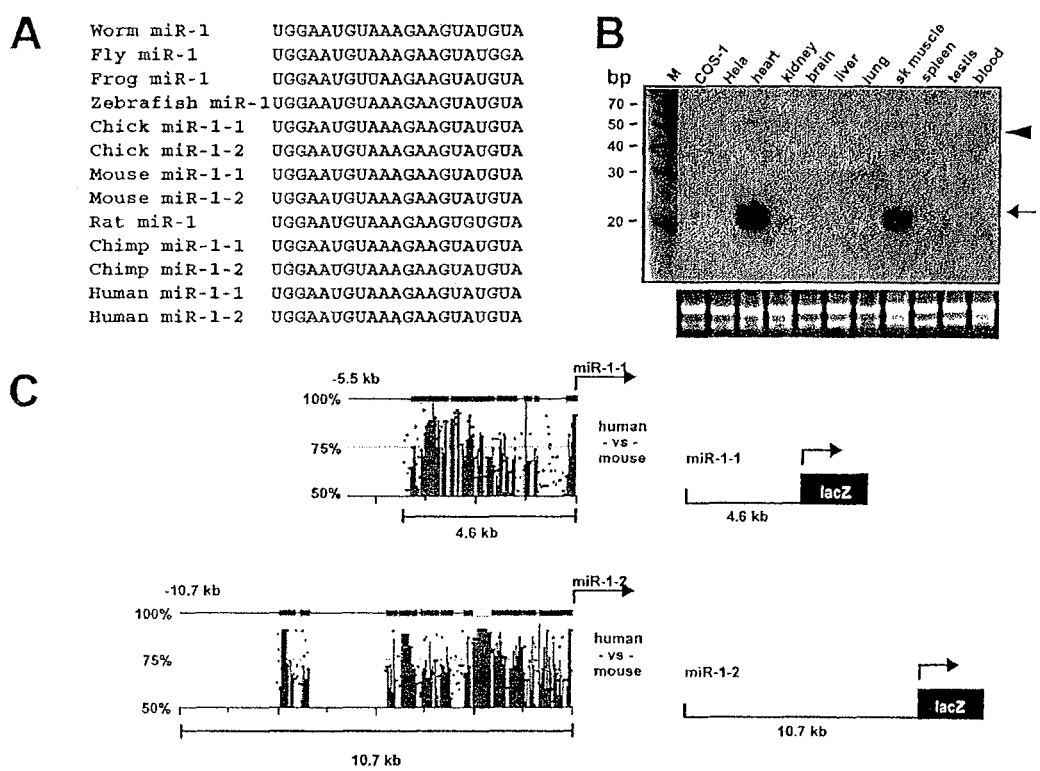
FIG. 1A-C

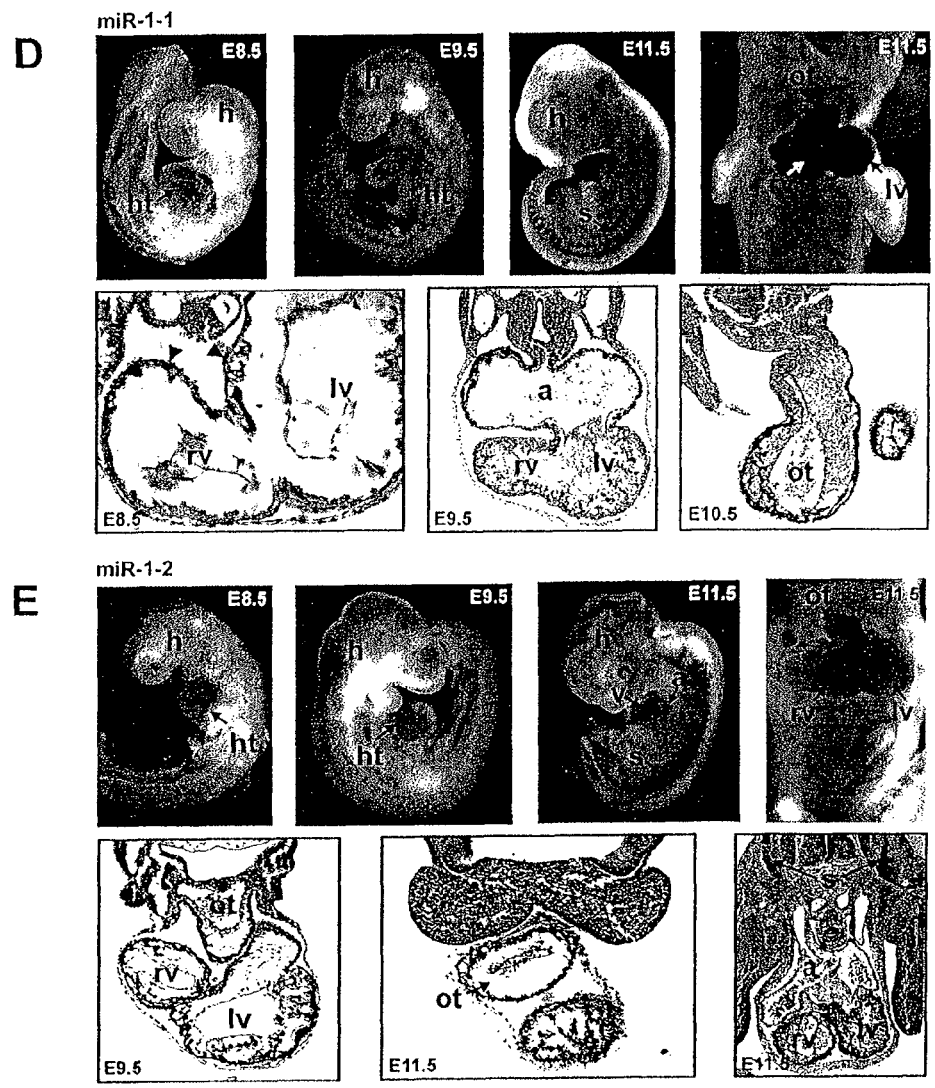
FIG. 1D-E

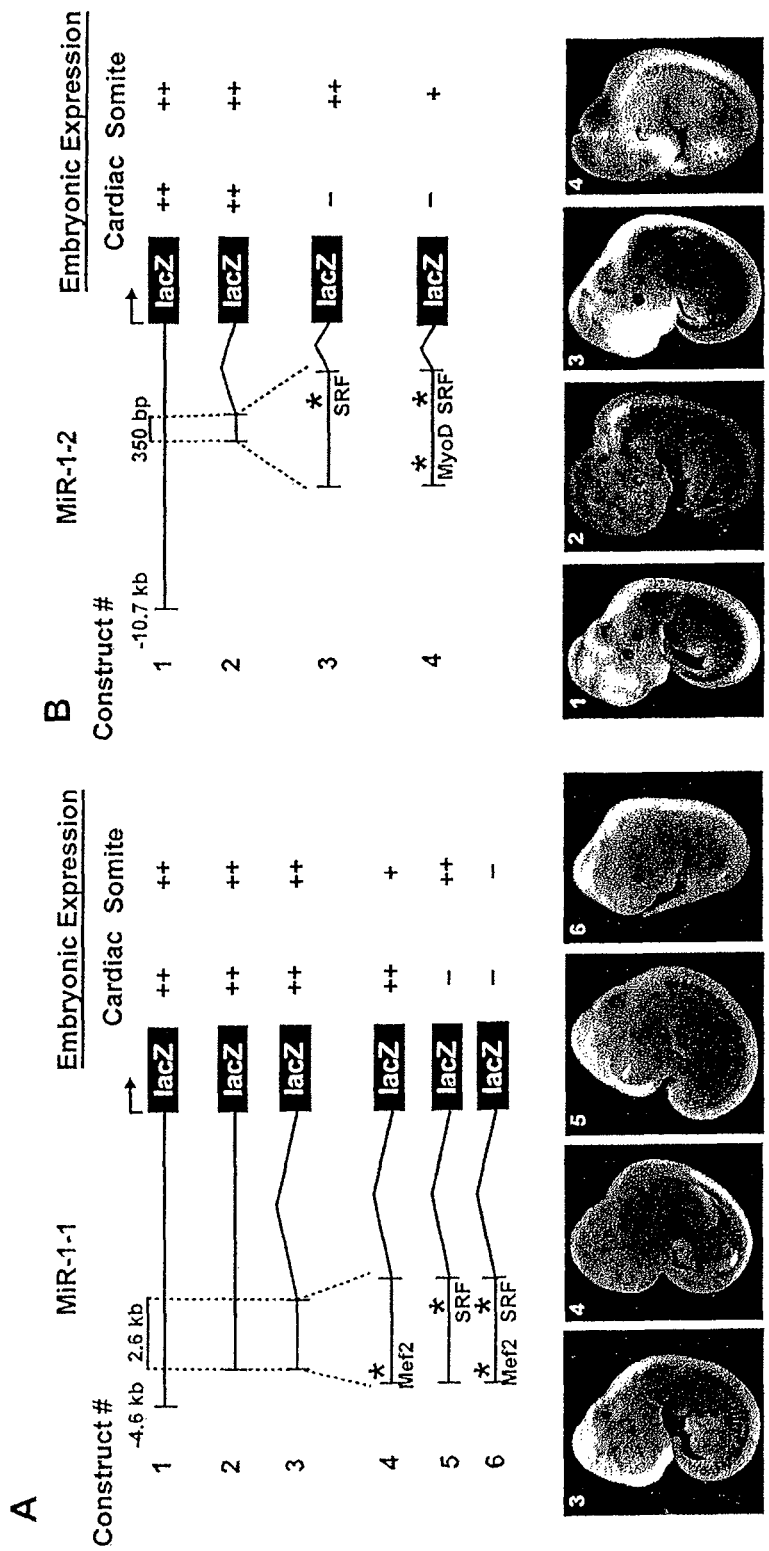
FIG. 2A-B

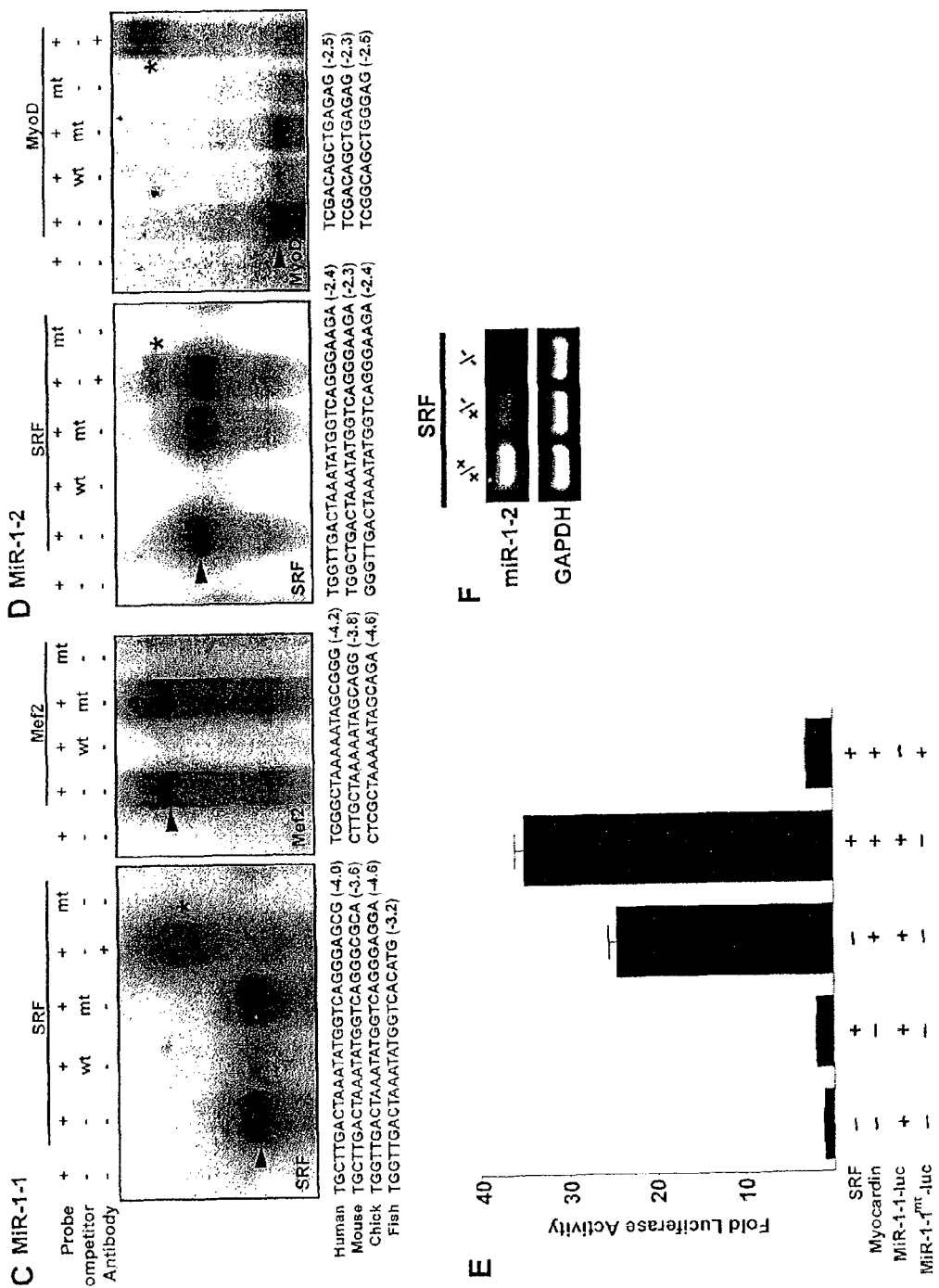
FIG. 2C-F

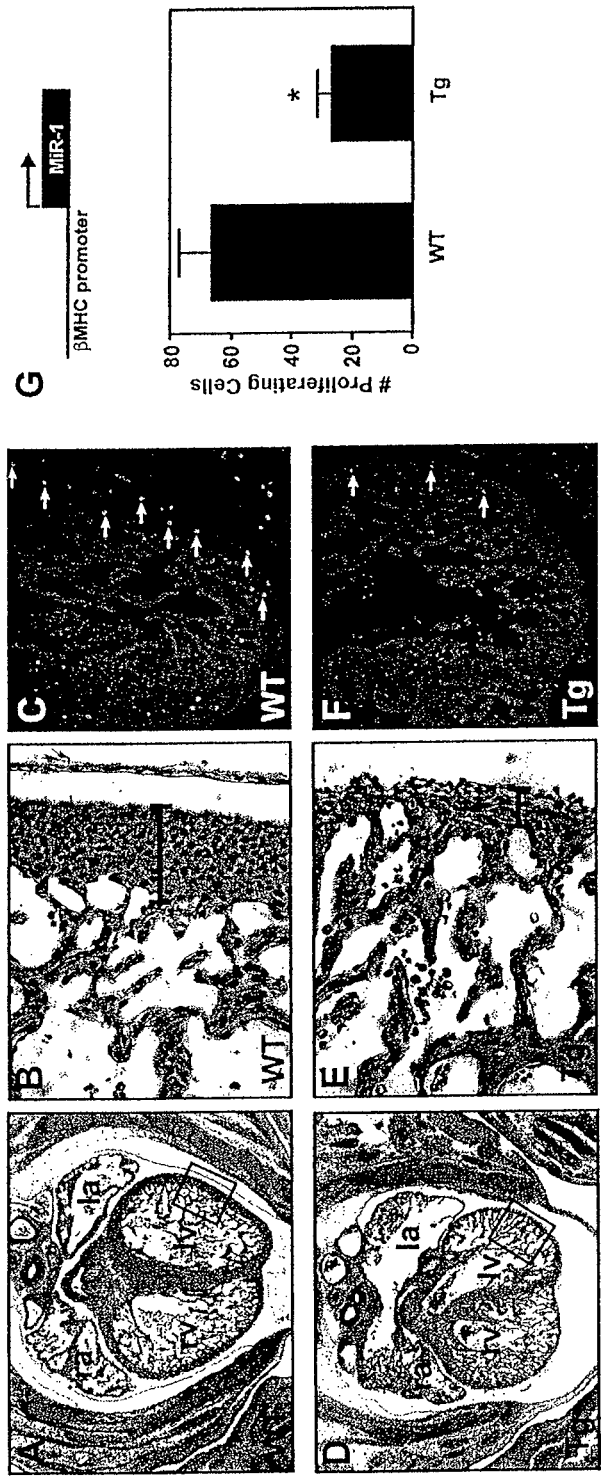
FIG. 3A-G

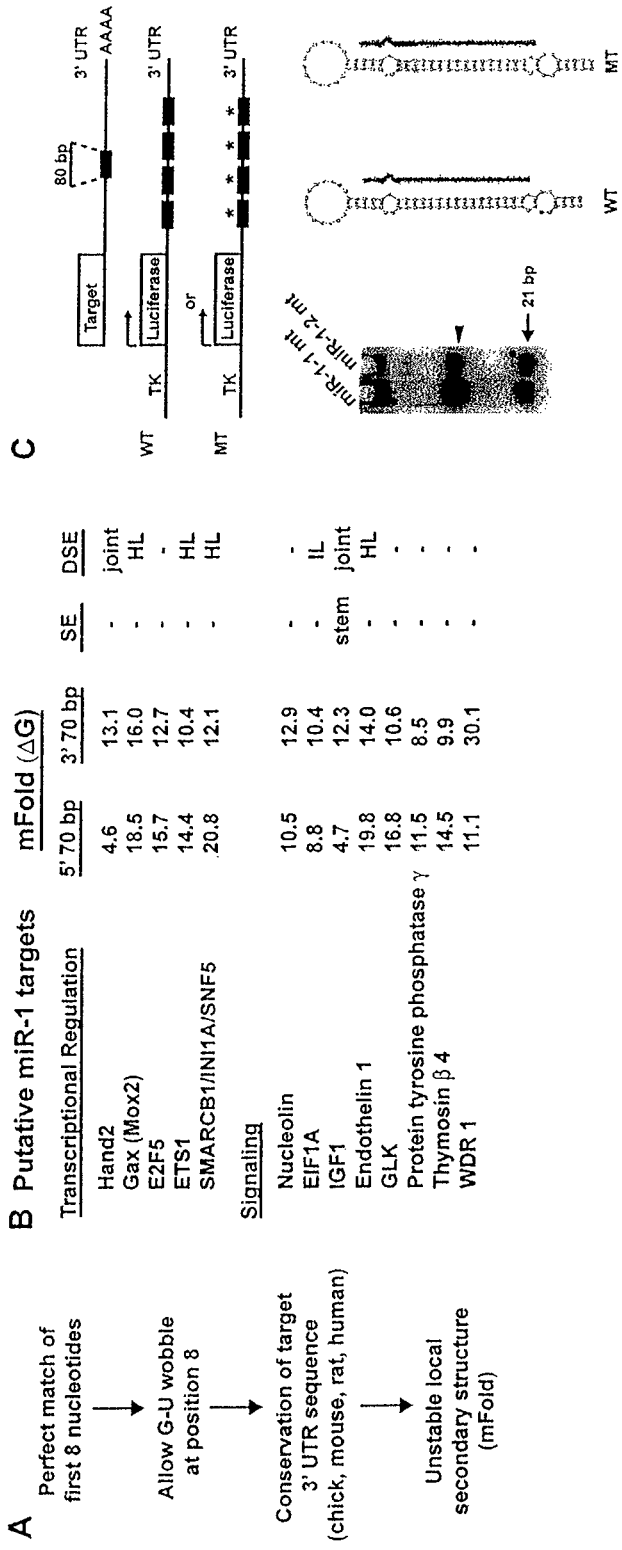
FIG. 4A-C

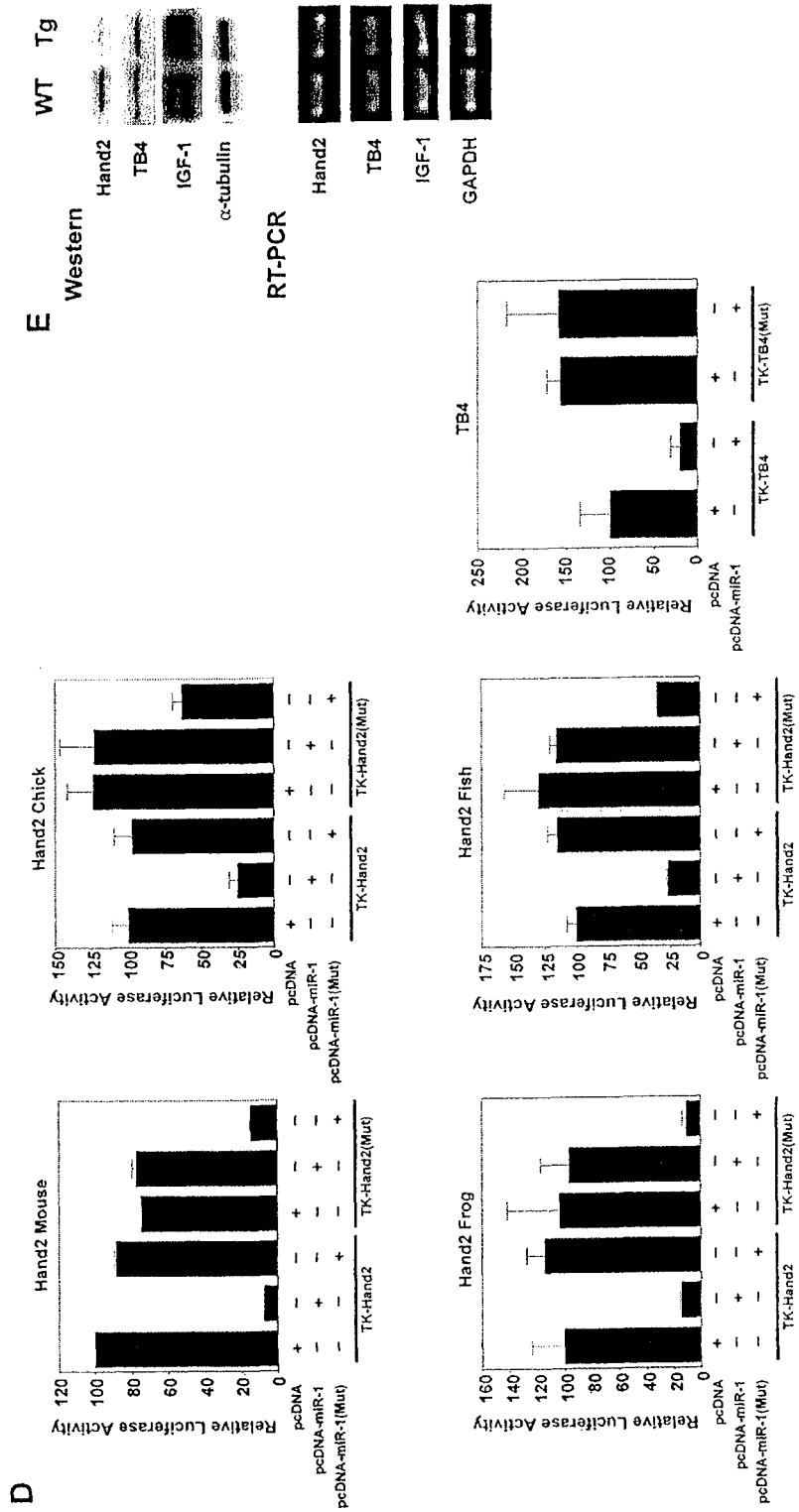
FIG. 4D-E

```
Lin-4      　　　　AGUC UGAACU  CC▓▓▓▓▓CU ▓▓▓▓GUGAACUCCA▓▓▓▓CU
Lin-14_CB  ATTTCC▓▓▓.T▓.......GC▓▓▓▓▓CAAC▓▓▓AAAAAAACC.▓▓▓▓CAAT
Lin-14_CE  TTTGTC▓▓▓CT▓AAAAATTGC▓▓▓▓▓CAAC▓▓▓AAA.......▓▓▓▓CAAT
Lin-14_CR  TCAGTC▓▓▓CT▓AAATTTTGC▓▓▓▓▓CAAC▓▓▓AAA.......▓▓▓▓CAAT
                  *         Site I           *       Site II Lin-14_CB  TTGTCAAAACTTTGGTCTCTCATCATATATCTTACCTCCTCTTGTCACACAACCCCCG
Lin-14_CE  TTGTCA...CCTTGGTCTCTCATCATATATCTTACCTC...TTGTCACAC..CCCCCA
Lin-14_CR  TTGTCA...CCTTGGTCTCTCATC.TATATCTTACCTC...TTGTCACACCCCTCTCG Lin-14_CB  TCCCAAATTTAGATCCCAACTCAAGTGTTTTTCTTTTTTTTTCCTTTCCTCTATATTT
Lin-14_CE  TCCCCAGT..........CTCAAGTTCATTTCTTACTTTGTAAC..............
Lin-14_CR  TCCTCAA.............GTGTTTTTTCTTTTTATTGTTTT.......ATATTC Lin-14_CB  TGTTTTCTATTCACAATTGTGTCTTTTTTCTTACCT...TTCCGACTAGTGCCCCAAA
Lin-14_CE  .................................TCCGT.........TTAGTGCGCCCAA
Lin-14_CR  CAAATTGT.....................CTTTTAAATTCCGATTAGTGTGCCCAA Lin-4      　　　　AGUG UGAA            CUCCA▓▓▓▓▓
Lin-14_CB  TTTC▓▓▓▓CAT▓▓CGATTAC..TC.C...AAA.CCAA▓▓▓▓▓AC.......TTTT
Lin-14_CE  TT.C▓▓▓▓CAT▓▓TGATTACACTCTCTTTTAATCCAA▓▓▓▓▓ACCAATT.TTTTT
Lin-14_CR  TT.C▓▓▓▓CAT▓▓CGATTAC..TCT......ATCCAA▓▓▓▓▓ACTTTTCATTTTT
               ** *           Site III Lin-4      　　　　AGU▓UGAACUCCA▓▓▓▓CU    AGU▓U▓AACUCCA▓▓▓▓▓
Lin-14_CB  .▓▓▓T.....GAA▓▓▓ATTCATTT▓C.▓AC.......▓▓▓▓▓ACCACTT
Lin-14_CE  TC▓▓▓T.....GAA▓▓▓ATTC...T▓C.▓AC.......▓▓▓▓▓ACCA...
Lin-14_CR  TC▓▓▓T....TGAA▓▓▓ATTC...T▓C.▓AC.......▓▓▓▓▓ACTACTT
                *                        *
                Site IV                        Site V Lin-14_CB  TT.A.CTC..CAACTTT....................CTAATATCAAAACCAATTA
Lin-14_CE  .TTACCTCATCCACTTTTCAGTTGTTTGGGGCCAAATATCTA.TATCCAAAGTAGT.A
Lin-14_CR  .TTACCTCATCCACTTTTCAGTTGTTTGGGGCCAAATTTATA.TATCCAAAAGTGCTA Lin-14_CB  GTCACGAATT.TAGTATTTTTATATATTTCTATCCGCCCTATTTTTA
Lin-14_CE  GTCTACAATT.TAGTATTTT.....ATTATTACCTCCCGCCGTTTTA
Lin-14_CR  GTGCACACTTCTAGTATTTT.....ATTATTACCCAACC...TTCTA Lin-4      　　　　AGU GUGAACUCCAG  ▓▓▓CC▓
Lin-14_CB  GCTTT▓▓▓T▓GTAAAAACCAA.▓▓▓GA▓CATTTGAAAATGATCTCATTTGAAAAACGA
Lin-14_CE  GCTTT▓▓▓A▓C▓TAA....AA.▓▓▓GA▓CTTTTGAAAATGATCTTCACCTCATTCAGA
Lin-14_CR  GCTTT▓▓▓T▓GT......CAAT▓▓▓AA▓CATTTGAAAATGATTTCCTCCTTTCACCAG
                * ***      Site VI
```

FIG. 6

```
Lin-14_CB   A..ATAGGCACCAGAAT.GATTTTCAAATGATTCTGATTATCATCTACACTCAATGCT
Lin-14_CE   A..GCAAAAATCAGG...CATTTTCCAAAGATTTTGAA.AACACATAAACCTCCTTCC
Lin-14_CR   ACGGTGCAATTCAGATGACATCTTCAAACGATTCTGAA...TACAAACACTT.CT...

Lin-4                   ACUGUGAACUCCA
Lin-14_CB   ..GTCAAAAAACUCA..AATTCC..G           CCT.CTTTTTCTCATTCTTCT
Lin-14_CE   AAGTC..AAAACUCACAA..CCA.A            CCT...TTTTCT..TACTTCT
Lin-14_CR   ..GTC..AAAACUCACA..TCCA.A            CCTTC.TTTT....TTCTTCT
                            Site VII
```

FIG. 6 Cont.

```
Lin-4                     ACUCUGAACUCC  ACUUCAG
Lin-28_CE   CCTACCTCCTCAAATGGAG......CGUAAGCATTCTTTTTTTT
Lin-28_CR   TCTACCTCCTCAAATGGAG......CGUAAGCATTCCAATTTTG
Lin-28_CV   TCTACCTCCTCAAATGGAG......CGUAAGCATTTTTTAAATG
                          **
                        Site I
```

FIG. 6 Cont.

```
Lin-41_CE   .........GCCACGGTTG.GCGAACGG.GTAAAAAGGAAGAGCCGATCG
Lin-41_CR   ...CTGAATCCCGGATTTATATGAGCCCTGTTTTTTTTAAATGTTGTATT
Lin-41_CB   GAAAAGGGCGCAAAAACTATATATGTATTCTCCCCCGAATCCCCGGCTCT

Lin-41_CE   CCTC...GTTACTCAAGGAAAAGGCTCGACGTCGTTTTATCTGAAAATTCTTTGA
Lin-41_CR   CCTCAAAGTATTTCGGAGGAGGAGATTATCAGTAGTTTTTCGGAGGAATCT...A
Lin-41_CB   TGTT...TTATCTTTTTGGCTCCGCCCCCTTTTAATTATTCTTGTTCGTCATACA

Lin-41_CE   TATTTAGAGAAATTTGAGAAT..ATTTCGATGAGATTCA..TGTAGGTTTTTCCA
Lin-41_CR   ATTTTATCAAACTTTTGGTGTCGACTTTCTAGATATTTT..TCTAAAACATAATC
Lin-41_CB   GTTATGCAAGTTTTCTCGTCACCATTTTAATGGTTTTTCCCTTTCGCCCCGCCCC

Lin-41_CE   AAAAATCGAACGAATTTTGTCGGAATATT........TGAAATCT........
Lin-41_CR   TAGAAATGGACTTCATTCGTCCAAAAATTAC......TGTAATCTTCTATCTC
Lin-41_CB   CATGCCTTTTTTCTATGAGCCCCATTTTTCTCTAGGATCAAATTTCCATTTTG

Let-7                               UGAUA UGUUGG
Lin-41_CE   CAGGAAA...AGTCTAAAGAATTAAAACACCG.ACAA..............
Lin-41_CR   CAGGATCCCCATTCACTGTAATTACAGTACGGTATAG..............
Lin-41_CB   AAAAGAGCTTTTTCTAAAAAAGCTCTTTTTTTCGGGATTTTTTGACTCCG
                                                Site VI Let-7             AUGAUGGA GU Let-7       UGAUAUGUUGGAUGA U GGAGU UGAUAUG  UUGG  AUG AUGGAGU
Lin-41_CE   ......TAGCACCT.CTTTT GGAGAAATTGCACC.AACUCAAGTA AGT
Lin-41_CR   CTTGTTTAAAATCAACTATCA CG .TC.TGCACCCACC CAAG.. AGG .C
Lin-41_CB   CCCACTTTTTGTCCCCGCCCC GGATCACACT..CCTC CAAG.. GGG CC
                                 Site V                    *
                                                  Site III Let-7       UGAUAUGUUGG AUGGAGU CAGU
Lin-41_CE   TTTATACAACGGTT  A  TC ACGCGATGTAAATATCGCAATCCCT
Lin-41_CR   TTTATACAACGGTT  A  TC AAGTCATTT..TTATGGCGACCCCT
Lin-41_CB   TTTATACAACGGTT  A  TC AAAACA..............CCCC.
               *                                    spacer
              Site I Let-7       UGAUAUGUUGG AUGGAGU U
Lin-41_CE   TTTATACAACCATT   C  T TGA...ACCATTG.AAACCTTCTCCCGTACTC
Lin-41_CR   TTTATACAACCATT   C  T AGA...ATTTCCCCAAATACAAAAACGTCCTG
Lin-41_CB   TTTATACAACCATT   C  T TTCCCGCCTCCTCTTTTTTGGAAAAGTTATA
              *         *
              Site II
```

FIG. 6 Cont.

```
Lin-41_CE   CCACCAATAGATTATTGCACTTTTCTGAGAGTTTTTCTGTGTTGGAA...
Lin-41_CR   TTTGTGACAAA...TTGCACTTTTCCGTT.GTTTTTCAATTTTGGAAA..
Lin-41_CB   TATATTGCACTTTTTTTGAAAAAAAAACCAATTTTTGGGTCTAAAAAAAT

Lin-41_CE   ......TCATAAT..........TTTCTAAACTGATTCGCAT..AATTTC
Lin-41_CR   ..TGACTGAAAATGTGGATTTCATTCCTAGAAAGGTT..AAT..AATCCC
Lin-41_CB   TATCGACAAAAAACTTTTTTTGACTCTAAAAATTGTTTTTTTCAAAAACA

Let-7           UGAU    AUGUUGG AUGA UGGAGU
Lin-41_CE   CAACACTGAAAAACTTTCTCAAC..ACCTCTGGTGACTATTTTCTTTTCC
Lin-41_CR   CATTTTTCAGCCACTTTCAGATTTGAAAAATGACTAATATTGTCTAGTTA
Lin-41_CB   AATTTTTTGAAAATTTTCCGGTGTCAATTGTTGTCTCCACACACTGCACC
                                Site IV Lin-41_CE   GGTGTTAATTGTCCCAATTGCCTAATGTCCCCAGTGTTCAT..TTAAGCT
Lin-41_CR   CATGGTGACTATGTCCGGTGTCAATTGTCCCCCACTTTCCCCCTTATATG
Lin-41_CB   C.TCCTGTTTTTTTCTGGC.TCCATTTTGTGTAAGCCCCGCCCCCTCCCT Lin-41_CE   CCCCATTTATTTTTATTTCACTGTCTTGGTTTTTGTGCCCTAGCGCTAAA
Lin-41_CR   CACCTTTTTATGGTCTTTTCTCTTTTTGACCCCGCTATTTCTCCGAAAAT
Lin-41_CB   AAAAATAGCCCCGCCCCTTTTCCTCTCGGAAAAGAAATAGAGCCAAATT Lin-41_CE   TATTGTT... .....TTATT TTAAT.GCAT GCTT
Lin-41_CR   TGGCGCCAAA ...TATTGTT TTAAT.GCAT GCT.
Lin-41_CB   TAATATATAA AAATATTGTT TTAATTGCAT GCT.
```

FIG. 6 Cont.

```
daf-12_CB    TAGTCCTACCCTA..CCT..TTA..T.ATACCTCGCC...TCCCC...CTTCCG
daf-12_CR    TAGTACCACTTCAAACCTCGTCAACTGATGCCATGCCATATCACTATACCTCAC
daf-12_CE    TAG....AAATCA..TCT.ACCAAACGATGCCATGCC...TCAATA..CCTCAC daf-12_CB    AA......TCAACGTTGCCTACC.CCAAAACGAT...TCTAGCCACATTTCCC.
daf-12_CR    AA......TCAACGTTGCCTCCA.TCATTAAAAT...TCTAGCCACATTTCCCA
daf-12_CE    AACTTGATTCTATATTGCCTCCATCCAACAAACTCAATCTAGCCACATTTCTTC daf-12_CB    .CTCT....TACCTCA.....TC.CCCCTA.TACTCACACAA.TCTTAT.TTAA
daf-12_CR    CCCCT....TACCTCGAAACTTC.CCCCCAGCATCCCTTCTG.ACTTGTCTTAT
daf-12_CE    TTTTTCACGTACCTCAA....CCACCCTTTCCATCC.TACAAATCGTATAATAT daf-12_CB    AC.......GTT......AGCA..AATT......TATCATATCATTGCTTATAT
daf-12_CR    ACCTCTCCTGTTTTCTTGAATAGGAACTAGTCACTATCATATCATTGCTTATAT
daf-12_CE    TCCTCTACCTCTTT....AACC..AATTCATCATCTTTTTAT.ATTGTTTTTAT daf-12_CB    C.........CTCTT.......TTTTCTTCA....AATATTCT....ATCAGT
daf-12_CR    CTTTTTTCGTCTCTTA..TTCTTTTTGTTCAT.TCATTTTTCTTGAAACCAGC
daf-12_CE    TTGCATTCAACTTGGAAATAGCCACTATTCATATCACTATTGCGTATTTCCTT daf-12_CB            ..........TAT.GT........... ...CT......TATGT.CTTAAGGCCA
daf-12_CR    ACCGAACAATATTGTTGAAGAAGAA GGGCTGAATAGTACAA.CAAAAAACCA
daf-12_CE    TC...ATTTTCTTGT........... ...CT......TATTTTCTTGAGACCA daf-12_CB    G.......AAATTTTATTGGCAAAGAGA....AAATCA..AGAGGTTCT.CTTC
daf-12_CR    AAA...AAAAATTCAAAAAACAAAAAATTTCCAATCACTAAAAATCCTTCTTC
daf-12_CE    GCACCAGAAGATTTTTTCGATGGAGAAC....TAAGCATGATAATTTGAAGTTT daf-12_CB    CCCAAT.AAAATTAGCTGGCTATATACGGTTACAGTTTTTCTTTTCTTTTCTCT
daf-12_CR    TCCAAC.AAAATTTCCTGGC.A.ATACGGTTA......TTCTTTTCTTTT....
daf-12_CE    TCCATTTAAAAAATGCAGGT.A.ATACGGTTA.....ATTCAAT.CT.......

daf-12_CB    CCTGCGAGTTGATGTTCGGTCTCCGGTTTTCTCTGTTCTACTTCTCCTCCTAAC
daf-12_CR    ...GCGAGTTGATGTTCGGTCTCCGGTTTCA.TGTTCTACTTCT......GAC
daf-12_CE    ...GCGAGTTGATGTTCGGTCTCCGGTTTCA.TGTTCTACTTCTAA...TGAC daf-12_CB    TAGAAACCATTTTTTATCCCAGCATCCGGTCGTGTTAACTTCTCTAA..AATCT
daf-12_CR    TAGAAACCTTTTTCTATCC.AACATCCGGTCGT.TT...TTCTCTTGCTAATCT
daf-12_CE    TAGAAACC..CTTTTATCT.AACATCCGGTCCTCCTA...TCCCTAATGTACCC daf-12_CB    CTCAAAATCCTTCATCCCAGTAGCCCTTTGTTTTCAAATTCCCAGTTATATTGC
```

FIG. 6 Cont.

```
daf-12_CR   CTTCAA....TTCAGCCCAGTAG.......TTTTCACATCCCC.GTT.TATTGC
daf-12_CE   AGTAGA.TATTTTTTCCCCGAA........TGATTAAACCTCC.....CA..GT Let-7                        U GA  AUGUU  AU        U
daf-12_CB   CGTCTATTGTATTATGTGAT C AC AAC TAACCC        TATATACTCAA
daf-12_CR   CGTTCATTGTATTATTTT  GC AC AAC GTACCC        TA.ATTTTC..
daf-12_CE   CAAATATTGTATTTTGTGAT C ATG AC  TAGCCC        TTAAT..TCCG
                             *  *
                                        Site I daf-12_CB   CCACTCAAATATCTCAGATTTTCATTCGAAGAACTGGTCTGGCACTGTTGAATT
daf-12_CR   TTATCTAACTATCTCA........TTGAAGAACTGGTCTGGTACTGTTGAAT.
daf-12_CE   TCAAT..ACTATCTCAGATTTTCA.TTGAAGAACTGGTCCGGAATTATTGAAT.

daf-12_CB   CTTCATTTGAAT..TTTGTA..ATTTTT.TTCAAAGTT.TCGT..TGTTGAGTT
daf-12_CR   CTTCATGTAGATCGCTCATCTTATTCCCGTTCCTAGTTGTCGCCCTATCTGTTT
daf-12_CE   CATCAGCTAGAA....AATG..GTTTTC.CTC..AG...TCAT..T.TTAAACT daf-12_CB   TCTTTCATTTTTCCGTCTCTTTCTCCATCCCAAA..TTCTCCCTGGCATTTTGT
daf-12_CR   TCCCCCTTGTTTCCCTCTCCT.CACCTTCTCAAAGTTTTTCCTCCACAGCCGG.
daf-12_CE   TTTTTTCTATTTAAGACT.TT.CAAC.TCCCAA......CGCCTGGCATTTT..

daf-12_CB   TCATCTTCTA.AGATTTCTTTCGTATTTTTGTGGTCCTGTAGTTTACCGATTTT
daf-12_CR   .CATTTTTTTCAGATTTCTTTCGT..TTTTGTGGTC.TGTAGTTTACCGATTCC
daf-12_CE   ...TTTGTTTCAGATTTCTTTC.T..TTTTGTGGCC.TGTAGTTTACCGATTCA daf-12_CB   TGTGCGCACCCGAAAATTCTTCAGTCCTAAAAAAAAGTCAATT.CTTGCTTAAT
daf-12_CR   TGCTCGCGCCCAAAAGTT.TTCA........AAAAAGTCAATT.CTTGCTTAAT
daf-12_CE   TGCGCGCACCCAAAAAAT.TTCA.........ACAAGTCAATTTCCCGCT....

daf-12_CB   AACTTAATGTTTTATTGTGATTTGTCACTATTTCATTGTGATTTTGTGATTGAG
daf-12_CR   AACTTAAGTTTCTATTGTGATGTGTCACTATCTTATTGTGATTTTGTGATTGAG
daf-12_CE   AAC.....GTTATATTGTGATGTGTCACTATTTTATTGTGATTATGTGATTGAG daf-12_CB   AAACCCC.....CTATCTTC.TTCTTT.TTTTGTTTCAAGTACAATTTTTCCCG
daf-12_CR   AATCTAA.....TCATCCCT.TTATCTGTCTTTTTTAAAGTACAATTTGTTC.G
daf-12_CE   AATTTACTGCTTCTACATCTATCCTCTATCCCTGTTCA.GTACAATTTTGAC..

daf-12_CB   ATTTCTATCTTTCCCCTTCCCACTACCACTGCACTTTTTTTCCTACACACCCTT
daf-12_CR   ATTTCTATCTTT....TTCCC..CATC.CCGCACCATCTTTTCTTCACACTCTT
```

```
daf-12_CE    .TTTCTATCCTTC..CTTCTT.......CAGCAC...........CAC.CTATT daf-12_CB    TCTTTTCTGCA...CACTGGTCT.TGTAAAGCTACGGTGATACTAATGGACTGT
daf-12_CR    TCTTTTCAACACTGCACTGGTTC.TGTACAGCTACGGTAGT..TAA....CTG.
daf-12_CE    TCTTTTCAACACTGCACTGGTTCATGTTTAGCTACGGTGAATTTATC...TTG.

daf-12_CB    ACTGTAGCC.TATGTAACTGTTTTTCCCCTGCTAGCTCTTCTTCTTCTTCTTTT
daf-12_CR    ACTGTAGCCCTATGTAACTGTTT.....................TTTTCT.TCTT
daf-12_CE    ACAGTAGCT.TATGTAACTTTTT.....................CTGTCTGTCTT Let-7                    UUGAUAUGUUGGA UGAUGGAGU
daf-12_CB    CCTCTTTCGTAATTATACAACACCAC.ACCUCTA..TTTTTCTTTTGCACTACCT
daf-12_CR    TTCTCTTTTTTAATATGCAACACCAC.ACCUCTTCCTTTTCCTCGTCTACCTCGT
daf-12_CE    TTCTCTTTTTTAATATGCAACACCAC.ACCUCTA..TTTTCC..TTGCACTACCT
                            *
                          Site II daf-12_CB    CGATCACACC...ATTTCTC
daf-12_CR    TCCCTCTCC..A.ATTTCTC
daf-12_CE    CGATCACACCTCCATTTCTC
```

FIG. 6 Cont.

```
Let-7                    UGAUA UGUUGAU         U
Lin57_CR     ATTTTTCTCAGCCT.T AT C..      AAAACAT
lin57_CB     TTTTT.CTGTTTA..T T G..       AAAACAT
lin57_CE     ATTTT.CTCTCTGTCT A. TT       CAAACAT
                              *
                            Site I Lin57_CR     ATTCCCATACTTGTATTAAATGCCAAAACGAAG...ATATTCA..ATTC
lin57_CB     ATTCCCGTACTTGTTTCAATGACGCCAAAACGAAA.ATACCTA..AAAG
lin57_CE     ATTTTACTACTTGTATTG..AATGCCAAAAAATACCATATTTATTAAGG Lin57_CR     AACCCCCAC.TCT.CA.TCTTGTATTCTCAGAACGTGTCACTACTTAG
lin57_CB     AGCCTTACTC.TCTGTA.CCCCCAATCTATTAAACGTGTCACT.CTTAG
lin57_CE     AGCATTGTTCATTTACAGTTTTGTACTCTCAGAGCGTGTTATTATCTAG Let-7                           UGA   UGGAUG   AGU
Lin57_CR     AAGTAATTGTATACTGTTGTC...A    TG.TAG   CC.......CAA
lin57_CB     AAGCAATTGTATACTGTTTGCCAAA    TG.TAG   CCTTCTCCTCCA
lin57_CE     AAGCAATTGTATACTGTTCTC...A    TG.TAG   TC.....CCCCA
                                    *
                                  Site II Lin-4                                       A UG  AACUCCA  GU
Lin57_CR     GAATACTTGTTTCAGTTACTATGTACCCTT CA ..TA...       TAG
lin57_CB     GAATACTTGTTTCTGTTACTATGTACCTTC CA ..AT...       TAT
lin57_CE     GAATACTTGTTTCTGTTACTATGTACCCCT TT TAAC...       TAT
                                           *  *      *
                                            Lin-4 site I Lin57_CR     GTA...TTCTTTTTGTGTGCTCCATTT...TCTCCAGA
lin57_CB     GGAAATTTTTCTTTGCGTGCTCCAAAAAAACCTTCAAA
lin57_CE     GAAA......CTTTTTATGTTTCA......TTTTCTAT Lin57_CR     TGTCATT.TTCTTGTTCATTTCTAATTCT..AAGCTCCTCCTCCTCTAAT
lin57_CB     TGATTTCATTCTCATTTTTTCTCAATTTCTAAGGCCCCTTCTCCACTAAT
lin57_CE     TGATTTC......ATTTGTTTGTCATTTTCAAGCTCCTCTTTCCAC..AT Lin57_CR     AAGCTTTAAT......TGCATGTCTTTCACAC...TTATTTATTTTCTAT
lin57_CB     AAGCTTTATTCTCTTTTGCATGTCTTTCAAACAACTTATTTATTTTCTAT
lin57_CE     AAGCTTTAAC......TGCATGTCTTTCATTT...TTATTTATTT.CTAT Lin57_CR     TTGCC.AATTGTTTAATATGTGCAACACTTGT.TTTGATGTTACAGTTCT
lin57_CB     TCACCCAATTTTTTAATATGTGCATGATTCTTCTTTCTTGTTATAGCATT
lin57_CE     TTGCC.AATTGTTTAAC.TATGCA.CACATTTGTTTCATGTTT.......

Lin57_CR     CTATGATCTAGCATTTTGTGTATTTTTTCTTCTCATTGCAACCAAACCCC
lin57_CB     TTGTG......TATTTTCCCCTTAATTATAGCCCCCTACAACCGTCCCCC
```

FIG. 6 Cont.

```
lin57_CE                                     ...........................CTCCAGAGA........

Lin57_CR    TACCTCTCACACCTCGAAATCATTGCGAACTC...TCATGTCCATCC...
lin57_CB    TACCTCTCTC.CCCAAAAATCAT.ACGAACTCGTCTCTTGTCCATCCCAT
lin57_CE    TAACTTTCCC......AAAT.............TCAAGTTTGCGCC..

Lin57_CR    ...AAATCGTGT....TGTTCTTTATTCTTACGGTT..TTGATGTTTCC.
lin57_CB    ACCAACTCGTGTCTCCTTTCTTTTTTTCCTACGGTT..ATCGTGGTTCCC
lin57_CE    ...AACTCGTGC....TGCTCTTTTATTGTACGGTTTTATAACGTTTCC.

Lin57_CR    ....TCCACGGAATCAGGGATTGTAGCGCAGTTTTAACCGTTTTGAACTA
lin57_CB    AACATTTTGGGAATCAGAGATTGTATTGCAGTTTTAACCGTTTCGAACTA
lin57_CE    ....GTCTTGAAATCAGAGATTGTA...GCCGTTTT.......TTGAAA.A Lin57_CR    GAAT..ATGCCAAAGATTCGTTATTT.TCATCTAGTT.GTCATTAATTTT
lin57_CB    GAATTCATGCCAATGATTCGT..TTT.TCATCTAGTTTGTCATTACTTTT
lin57_CE    GGAT..ATGCCAAAGAATCGTCCCCCACCCTCTAGTT.GTCATTTGTTAA Lin57_CR    T...ATAGCCGAAGTGACCAT...CCATCCCCGCTTTTCTCAATTGTTTC
lin57_CB    TTTCATAACCGAAGTGACTTTTTCCCAAACCCGCTTACAACTTTTCTACC
lin57_CE    ....ATAGCCGAAGTGACCCA....ACAACCCGCTTTTGTCCCTCTAC.

Lin57_CR    CCATT...TTCTCTACTAATAACCGTTTTTCTATTTTCC..CTATATTTA
lin57_CB    CCATCAAGCAATTTAATAATAACCGTTTTTTTTGTTCATGCTACCTCAA
lin57_CE    .............TAATAACCGTTTTATTATTATTATCACTCAATATTTA Lin57_CR    TCTTTTTATGTACCTCTTTCACG..CTCCCATGTCCTCACGTGATCAATG
lin57_CB    TTTGCTTATGTACCTCTTTCAAAAACTCCCATGTCCTCCCAAAAATTCTG
lin57_CE    TCTTTTTATGTACTTCTTTCACTG.CTCCCATGTC.....GTGATTTCTG Let-7                          UGAUA UG UUGGAUGAGGU U
Lin57_CR    ATTTCACAGAACTCGTAACTATCTCGCACCATCATTCTACTCAATACAT
lin57_CB    ATTTCA..........GTCCCCC......CATACAT
lin57_CE    ATTTCACATT.TTCCAGACTATCTCGCACTTTCATTCTACTCAATACAT
                                          *          *
                               Site III Lin57_CR    CCCAG..CTTTTGCCATACATTCTCCGATTCGAATTC.TTGTGTGCTTTT
lin57_CB    CCCAAGCCTTTTGCCATACATTCTCCGTTTCAACCTAATTGCGTGCTTAT
lin57_CE    CCCAGCTTTTTGCCATACATTCTCCGATTCGAATTC.ATGTGTGCTCGT Lin57_CR    CTCAAATAATC...ATTTCCTTTAC....TCGTATTAATCGTTTTTCTTA
lin57_CB    TATTCATCCTTTGTATAGCCTTTTCAGCTTCATCAAAATTTATTGGCCCA
```

FIG. 6 Cont.

```
lin57_CE      ..TTAACTATT...ATTACCTGTAT...CCACCGATTACTTTTTTGTTTA

Lin-4                      A UG GAACUCC          CU
Lin57_CR      CCTCCTTGCTCCCATC ..       ........ AATAATCCA
Lin57_CB      CCTCATCTCCCAGAAC .C       ........ AATT.TACT
lin57_CE      TTCGCTCCCTTTTTTC ..       ........ AATG.....
                                *
                            Lin-4 site II Lin57_CR      GCGTTTCTTTTCTCTTGAATGCTCGCTCCAACTCTATG
lin57_CB      ATGCTCCATTTTCAGTAAAAACCTCCTCCT.CTCTATG
lin57_CE      ATTTATAGTTTTCAATTTGTCTTCTCACAACTCATCTA Let-7                UGAU         AUCUUGGAUG             AUCGA
Lin57_CR      A    ACTTGTCC...GAT  AGTTTCTT..CTCTATG          TT
lin57_CB      A    ACTTGTCTCTTGAT  TGTTATCCAATATTATG          TT
lin57_CE      A    ACTTGTCC...GC. AC..........CT.TATG         TT
                *                        Site IV Let-7              UGAUAUG  UU    GGAUG  AUCGA
Lin57_CR      GATTCTTTT. CC  CC..GA......TT..TA       ATTCCA..
lin57_CB      GA...ATTT. CC  CCCCAATCCTTTTTTCTT       AACTCATT
lin57_CE      GACTCATTTT CC  CACCCAATACAATT..TA       ........
                *                        Site V Let-7                                  UGAUAUCUUG  GAU AUCGA U
Lin57_CR      ..........ATACTGGC.TATGA            GCTT         CC.
lin57_CB      TTTTCTCTCCATACTGGCCTATGA            GCTT         CCC
lin57_CE      ..........ATACTGTCTCTTAC            GCTT         CAA
                                       *   *  *
                                         Site VI Let-7                        UGAU   AUCUUGCA  U  AUCGACU
Lin57_CR      AATTTTCCA.CAATTCTA   AATT  CCA  T.        GC
lin57_CB      AACTGTCCC.CAATTCTA   ATG.  CCT  TT        AA
lin57_CE      TTTTTACCATCTATTCTA   AT.   CCA  T.        AC
                                 **      ***
                                   Site VII Let-7                    U AUAUCUUGGAUGA    AUCGA
Lin57_CR      CCAT...GTTTTC            .G  TCC      AGCCTT..C
lin57_CB      AAATTAAACCCCA            .G  .CC      AACTCC..C
lin57_CE      CCATT...TTCTA            .G  .CC      AACTTCAGT
                            *           **
                                Site VIII
```

FIG. 6 Cont.

```
Lsy-6_CE              GCU  C   AG
Cog-1_CE   TTTCTTTTTTTTTCCA  CAT  CA       ACCAA
Cog-1_CB   TTTTTCTCTACTTAAA  ...  CA       TCCCC
Lsy-6_CB              GCC  C   AG
                               *
                             Site I Cog-1_CE   ACTCCCTTTTACCGTTAAACCATGCCCAA
Cog-1_CB   CCAAAACTTCACCCGTTTTCTTTATTAAA
```

FIG. 6 Cont.

```
mir-273                              ▓CGGCU▓UGU▓
die-1_CE    CTACCTTTT.TTCTTCT▓AT▓..▓GTT▓▓▓▓▓▓▓CAAATGTTCCGGAA
die-1_CB    CTAAGTCTTATTTCTCT▓AA▓..▓TAT▓▓▓▓▓▓▓CCCTTTTACTGG..
                             **  *     *    *
                                    site II die-1_CE    CCAAATGAAAATCCCCGCCTTTCTCGTCTTTTGAAGTCCGTATCCTCCTTGT
die-1_CB    ..ACACGGAAGACACATTTTCATACATTTTTTAAACTTCGAATTCTGTGGTC die-1_CE    AATCTTCCACCACCACTCGCCCCAGTTCTTGATCTCCGTTACCGAATGTTAA
die-1_CB    CATCTTCCCCAAATCCTCGCCCC.GTTTCCGATCTCTCTT.CCGA...TTAT die-1_CE    AACACGTGAATATGTAATTGTTTTTTGTCTC........ATCTTCCGCTCCC
die-1_CB    GTCTCCTCGATTTTTAATTTTTCTTCCGATGTAAAAAAAACCCATCACCACC die-1_CE    CG..AAACCTCTTTCATCACAGCC.............................
die-1_CB    CAGCAAACCTCTTTCATTCAAAATTT CATCAATTTTATCGTTTTTTTTC mir-273                     ▓UC▓▓CU▓U▓U▓A ▓▓▓▓UG
die-1_CE    .......CCCCAAAT.T▓TC▓▓A▓▓.▓AGCA▓▓▓▓▓CCAAACATA
die-1_CB    TAAATGTCACTCTGTCT▓TC▓▓A▓▓.▓AGCA▓▓▓▓▓AATTTCATT
                             ** *
                                 site I
```

FIG. 6 Cont.

```
Hid_D.sim    ATGATTTATG TTTATTT... GTAATATT.. ....TTTTGT CATTGTTTGT
Hid_D.ere    ATGATTTATG TTTATTT... GTAATATT.. ....TTTTGT CATTGTTTGT
Hid_D.mel    ATGATTTATG TTTATTT... GTAATATT.. ....TTTTGT CATTGTTTGT
Hid_D.yak    ATGATTTATG TTTATTT... GTAATATT.. ....TTTTGT CATTGTTTGT
Hid_D.pse    ATGATTAGTA TTTTTTTTTT GTAATATT.. ....TTTT.T TGTCATT.GT
Hid_D.ana    ATGATTTATG TTTAATT... GTAA..TT.. ....TTTTGT CATTGTTTGT
Hid_D.vir    TTAGTTAAAT TTGGTAGTCA GTAAGCAGGA TATATTTTCA TGAGGATTA.
Hid_D.moj    TTAGTTAAAT TTGTTAGTCA GTAAGCTT.. TGATTTTTCA AGTGGATTAC
```

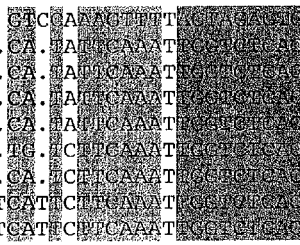

```
Bantam
Hid_D.sim    TCATCAT.CA..AT.CAAAT...........AATATA..ATA GTTTTAAGCT
Hid_D.ere    TCATCAT.CA..AT.CAAAT...........AATATA..ATA GTTTTAAGCT
Hid_D.mel    TCATCAT.CA..AT.CAAAT...........AATATA..ATA GTTTTAAGCT
Hid_D.yak    TCATCAT.CA..AT.CAAAT...........AATATATAATA GTTTTAAGCT
Hid_D.pse    TCATCAT.TG..CT.CAAAT...........AATTTA..GTT GTTTAAGTCC
Hid_D.ana    TCATCAT.CA..CT.CAAAT...........AATCTA..GTA GTT..AAGCC
Hid_D.vir    .TTTTGTT.AT.CT.CAAAT...........AATTTA..GTT ATTAAGCA.A
Hid_D.moj    ATTTTGTT.AT.CT.CAAAT...........AATCTA..GTT .TTAAGCACA
                    ** *           *
                          Site I Hid_D.sim    CCACGCCCAG GAGGTTGATG GCAAAACGAT TGAAACTTGG CCAGAAGAGA
Hid_D.ere    CCACGCCCAG GAGGTTGATG GCAAAACGAT TGAAACTTGG CCAGAAGAGA
Hid_D.mel    CCACGCCCGG GAGATTGATG GCAAAACGAT TGAAATTTGG CCAGAAGAGA
Hid_D.yak    CCACGCCCAG GAGGTTGATG GCAAAACGAT TGAAACTTGG CCAGGAGAGA
Hid_D.pse    CAGGACCCGG GAAATGTCCA GCCGGGAAAT TG...TCTGC CCCTGAAAAA
Hid_D.ana    CCCGCCCCAG GGAGCGAGTT CGAGCGAGGT TGAAAATTCG CCCAGAAATA
Hid_D.vir    CATTGTTCAA GAAAT...TT GCGCAA.... .AATGTCCAT TGAAATAGTC
Hid_D.moj    CATTGTACAA GAAAT...TT GCGCAACAAT TGAAATTTAC CAAAAGCAAC Hid_D.sim    G..ATAGTTT TCCC.ATTCG T.ACA
Hid_D.ere    G..ATAGTTT TCCC.ATTCG T.ACA
Hid_D.mel    G..ATAGTTT TCCCCATTCG T.ACA
Hid_D.yak    G..ATAGTTT TCCC.ATTCG TCACA
Hid_D.pse    G..GCCGCCC TCTC..TCCG ....A
Hid_D.ana    GCGATAGGGT TATCCCATTC TCAGA
Hid_D.vir    C...AAAGCT TCACGACACG TTTTC
Hid_D.moj    GGGAAAGGGT GGACGAAACA TTTTC
```

FIG. 6 Cont.

```
Bantam         TCGAA         TT                              TG
Hid_D.sim      CA..CTTTT .CC ..AAT..GCACA..........TT        TC
Hid_D.ere      CAG CTTTT .GC ..AAT..GCACA..........TT        TC
Hid_D.mel      CAG CTTTT .GC ..AAT..GCACA..........TT        TC
Hid_D.yak      CAG CTTTT .GC ..AAT..GCACA..........TT        TC
Hid_D.pse      AAA CTTTT .GC ..AACACGCACA..........CA        TC
Hid_D.ana      CAG CTTTT T C ..AAT..GCACA..........CG        TC
Hid_D.vir      AGG TTACC T G TTAACAC..TCAAAGCCAAGCGTTG       TT
Hid_D.moj      AGG TTATC T G TTAACACACTCAAAGCCAAGCGTTG       TA
                 *      * **       Site II (large spacer:26bp)

Hid_D.sim      ACAA. TGGAAATTAA TGAAA.....
Hid_D.ere      ACAA. TGGAAATTAA TGAAA.....
Hid_D.mel      ACAA. TGGAAATTAA TGAAA.....
Hid_D.yak      ACAA. TGGAAATTAA TGAAA.....
Hid_D.pse      CCAAA TGGAAATTAA TGCAA.....
Hid_D.ana      ACAA. TGGAAATTAA TGGAA.....
Hid_D.vir      AA..C TGGAAATTTA TAGAGGGCGC
Hid_D.moj      AAAAC TGGAAATTTA TAGAAC....

Hid_D.sim      ......ATTG ATCTCCGCAG CTAGCCAAAG TTAAAAAGA AAT.......
Hid_D.ere      ......ATTG ATCTCCGCAG CTAGCCAAAG TTAAAAAGA AAT.......
Hid_D.mel      ......ATTG ATCTCCGCAG CTAGCCAAAG TTAAAAAGA AAT.......
Hid_D.yak      ......ATTG ATCTCCGCAG CTAGCCAAAG TTAAAAAGA AAT.......
Hid_D.pse      ......GTTG ATCTCCAACG ATAGCCAAAG TCAAAGGAAA AAGTAATTCA
Hid_D.ana      ......ATTG ATCTCCGCAC ATAGCCAAAG TAAAAAAGA AAT.......
Hid_D.vir      AACTCAATTG ATCTCCATAG CTAGCCAAAG TCAAAGTCA A.........
Hid_D.moj      .ACTCAATTG ATCTCCACAG CTAGCCAAAG TCAAAGTCA AACACACACA Hid_D.sim      .......... ......GAAG AGGAAAA... ....CATATT ..........
Hid_D.ere      .......... ......GAAG AGGAAAA... ....CATATT ..........
Hid_D.mel      .......... ......GAAG AGGAAAA... ....CATATT ..........
Hid_D.yak      .......... ......GATG AGGAAAA... ....CATATT ..........
Hid_D.pse      .......AAC GAAGGAGAAG GGGAAAGAC. ....CATGTT ..........
Hid_D.ana      .......... ......GAAA AGGAAACCCC ....CTCATT ..........
Hid_D.vir      ........CA CACGCAGCAA ATCAAATTTT TGTTTGTTT. ..........
Hid_D.moj      CATACACACA CATGCAGCAA ATCAAATTTA TATTTATGTC CCCTTTCTGT Hid_D.sim      .TTATAGGCA ACTTTCACTA ...TATGCT. ..AGAATTTC CA........
Hid_D.ere      .TTATAGGCA ATTTTCACTA ...TATGCT. ..AGAATTTC CC........
Hid_D.mel      .CTATAGGCA ATTTTCACTA ...TATGCT. ..AGAATTTC CC........
Hid_D.yak      .TTATAGGCA ATTTTCACTA ...TATGCT. ..AGAATTTC CA........
Hid_D.pse      .CAGAGGGCA ACTTCCGAT. ...TTTGCT. ..GGCGTTTT CT........
Hid_D.ana      .TTCGTGGCG ATTTTCAATA ...ATCACTT TCAGAGCTCC CCA.......
```

FIG. 6 Cont.

```
Hid_D.vir     .TTTTTATTA TTTTTTGGTA AGTTTCAAAG C..ATTTTGC C.AAATTTCT
Hid_D.moj     ATTTTTGGTA ACTTTTGGTA AATTTCAATT TCAGTTTTGC CTAAATTTCT Hid_D.sim     GGGCGTTTCA ATGCTAATCG AATACA.... GTGA.CATGA A.........
Hid_D.ere     GGGCGTTTCA ATGCTAATCG AATACA.... GTGA.CATGA A.........
Hid_D.mel     GGGCGTTTCA ATGCTAATCG AATACA.... GTGA.CATGA A.........
Hid_D.yak     GGGCGTTTCA ATGCTAATCG AATACA.... GTGA.CATGA A.........
Hid_D.pse     GGCGTTTCA  ATGCTAATCG AATACACAAC GTGAACATGA A.........
Hid_D.ana     GGGCGTTTCA ATGCTAATCG ATTACC.... GTGA.CATGA A.........
Hid_D.vir     TGACGTTTCA ATGCTAATCG AACA...... GTGAAAAAAT AGTAAGGAAT
Hid_D.moj     TGACGTTTCA ATGCTAATCG AACA...... GTGGAAAACA A.........

Hid_D.sim     ..AGCAAACATAGCGAAAATATTAAGAAAATCAATCAAAA................
Hid_D.ere     ..AGCAAACATAGCGAAAATATTAAGAAAATCAATCAAAA................
Hid_D.mel     ..AGCAAACATAGCGAAAATATTAAGAAAATCAATCAAAA................
Hid_D.yak     ..AGCAAACATAGCGAAAATATTAAGAAAATCAATCAAAA................
Hid_D.pse     ..AGCGAAAATAGTGAAAAACAAAAAATCA.......AAA................
Hid_D.ana     ..AGCGAACATAGCGAAAATAGTAAGGAAAATTAATCAAAAAGAATAAATAAGA
Hid_D.vir     TTAAAGAGCAAAAAATAATTAAGAAAATGAACATATTAAAAGAAAAGAAAAATGA
Hid_D.moj     ..AAATACCGAAATGAAAACAAAATAA.AAATATATTAGAA.AATTAACATATGA Bantam                                GTCGAAAGTTTT       GTAAACTC
Hid_D.sim     ......AGAAAGAAAAACAAATCCGAAAATCGCATCAAATCAGGATTTAT.
Hid_D.ere     ......AGAAAGAAAAACAAATCCGAAAATCGCATCAAACAAGGATTTAT.
Hid_D.mel     ......AGAAAGAAAAACAAATCCAAAAATCGCATCAAACAAGGATTTAT.
Hid_D.yak     ......AGAAAGAAAAACAAATCCAAAAATCGCATCAAACAGGATTTAT.
Hid_D.pse     ......GAAAGGTAAAAACAATCCAAAAATCGCATCAAACAGGATTTAT.
Hid_D.ana     AAGATAGAAAAGAAAAAACAATCCAAAAATCGCATCAAACAGGATTTATT
Hid_D.vir     AAAACAAAAAAAAAAAAACTATCCAAAAATCGCATCAAACAGGATTTTTT
Hid_D.moj     AAAGAAAAAGAAAAAAAAACTATCCAAAAATCGCATCAAACAGGATTTTTT
                                     *                *
                                     Site III Hid_D.sim     ..ACAATACA ATTACATCAA CCGTTTTTT. ACAATGAGAA
Hid_D.ere     ..ACAATACA ATTACATCAA CCGTTTTTT. ACAATGAGAA
Hid_D.mel     ..ACAATACA ATTACATCAA CCGTTTTTTT ACAATGAGAA
Hid_D.yak     ..ACAATACA ATTACATCAA CCGTTTTTT. ACAATGAGAA
Hid_D.pse     ..ACAATACA ....CA.CAG TTTTTTTTT ACAATGAGAA
Hid_D.ana     T.ACATTACA AATATTTCAA CCGTTCTTT. ACACTGAAAA
Hid_D.vir     TTATCATTTA CAT.CAGCAA TTTTTTACTT GCATT....A
```

FIG. 6 Cont.

```
Hid_D.moj    T.ATCATTTA CAT.CAGCAA TTTTTTACTT GCATTGAGAA

Hid_D.sim    A.....TGTT ATAAAAA.GC A.......GA AAGTGAAAC. ....A.....
Hid_D.ere    A.....TGTT ATAAAAA.GC A.......GA AAGTGAAAC. ....A.....
Hid_D.mel    A.....TGTT ATAAAAA.GC A.......GA AAGTGAAAC. ....A.....
Hid_D.yak    A.....TGTT ATAAAAA.GC A.......GA AAGTGAAAC. ....A.....
Hid_D.pse    AAAAAATACA ATAAAAA.AT AAGA.GAAGA AAATGAAAAG TGAAA.....
Hid_D.ana    GACAAATGTT ATGAAAA.GC AGAAAGTGAA AAGTGAAAAC ....A.....
Hid_D.vir    AACGC.GATG AGAAATATGT ACATTAGGCA TAATTA..TG TAAAAGTTTA
Hid_D.moj    AATAT.TATT GTAAAAGTCT AGGGTTAAGA TCGCCAAGCG TTTTAGTTTA Hid_D.sim    .......... .......... .......... .....CAGAA ACA.TAAACA
Hid_D.ere    .......... .......... .......... .....CAGAA ACA.TAAACA
Hid_D.mel    .......... .......... .......... .....CAGAA ACA.TAAACA
Hid_D.yak    .......... .......... .......... .....CAGAA ACA.TAAACA
Hid_D.pse    .......... .......... .......... .....CAGAA ACA.GAAACA
Hid_D.ana    .......... .......... .......... .....GAGAA ACAGTAAACA
Hid_D.vir    GGT..TTAGA ATCGCCAAGC GTTTTAGTTT A....CATAT TCATAGCCTT
Hid_D.moj    CATATTTCTT AACACTAAGT TTTTATGTCT AAAGTTAAAT GCAAAAAAAA Hid_D.sim    AAAA...... .......... .......... .......... ..TTAAC...
Hid_D.ere    AAAA...... .......... .......... .......... ..TTAAC...
Hid_D.mel    AAAA...... .......... .......... .......... ..TTAAC...
Hid_D.yak    AAAA...... .......... .......... .......... ..TTAAC...
Hid_D.pse    AAAAGGGAAA GAGAAAGAGA AACGGAAAAC GGAAAACAAG AGTTAAGTGT
Hid_D.ana    AAAA...... .......... .......... .......... ..TTAAT...
Hid_D.vir    AAGTTTCTTT TATGTAAAGT TTTCCGCTTG TCATTCGACA AATCAAA...
Hid_D.moj    AAAAAAAACA CAAAAAAAAA AACACTAAAA AAAAAAAAAA AATCAAAAAC Hid_D.sim    .......... ....GAAAAG CTTAGAATTA AGTTCGCCAA GCGTTTTAGT
Hid_D.ere    .......... ....GAAAAG CTTAGAATTA AGTTCGCCAA GCGTTTTAGT
Hid_D.mel    .......... ....GAAAAG CTTAGATATA AGTTCGCCAA GCGTTTTAGT
Hid_D.yak    .......... ....GAAAAG CTTAGAATTA AGTTCGCCAA GCGTTTTAGT
Hid_D.pse    .......... ..AAGAAAAG TCTAGGCTTA AGTTCGCCAA GCGTTTTAGT
Hid_D.ana    .......... ....GAAAAG C.TAATCTTA AGTTCGCAAA GCGTTTTAGT
Hid_D.vir    .......... .......... .GCAATTCAA ATCTAAGTAA ATGTATT.GT
Hid_D.moj    TTAAAAAATA TGGGAAAAAA TGTACATCGA ATCTAAGTAA ATGTATTTGT Hid_D.sim    TCTACTTTCT AG.AATGTCT AAG.TCGGTT TAGTGAGTTT ATTGAGCTGT
Hid_D.ere    TCTACTTTCT AG.AATGTCT AAG.TCGGTT TAGTGAGTTT ATTACGCTGT
Hid_D.mel    TCTATTTTCT AG.AATGTCT AAG.TCGGTT TAGTGAGTTT ATTAAGCTGT
Hid_D.yak    TCTACATCTT AG.AATGTCT AAG.TCGGTT TAGTGAGTTT ATCGAGCTGT
Hid_D.pse    TCTAAATTCA AC.AGAGTTT AAGGTAGATT TAGTGAGTTT TTCACGCGTT
```

FIG. 6 Cont.

| | | | | | |
|---|---|---|---|---|---|
| Hid_D.ana | TTAAGCTTTA | GTTATAGATT | AAAGTCGATT | TAGTTCGTTT | TTTGAGCTGT |
| Hid_D.vir | TTATCATATG | TTAAATGCCT | GTAAGTAGAG | CAATATTTTT | TGGTAGCTT. |
| Hid_D.moj | TTATCATATG | TTAAATGCCT | GTAAGTAGCG | CAATATTTTT | TGTTAGCTTT |

| | | | | | |
|---|---|---|---|---|---|
| Hid_D.sim | C...TTCGGA | CACAAGTTTA | CTTGTA.... | TATGTATATA | .......... |
| Hid_D.ere | C...TTCGGA | CACAAGTTTA | CTTGTA.... | TA......TA | .......... |
| Hid_D.mel | C...TTCGGA | CACAAGTTTA | TTTGTA.... | TAT....... | .......... |
| Hid_D.yak | C...TTCGGA | CACAAGTTTA | CTTGTA.... | TAT......A | .......... |
| Hid_D.pse | TAT.TTTGTA | CATACATATA | CCTAAAGCAA | TATTATTCTG | TGTAGCCAT. |
| Hid_D.ana | C...TCTGTA | TGGCAGTCTC | TCCTTATTAT | TATTATTTTT | TTTTTTTGTA |
| Hid_D.vir | AAGAGTTATT | CATTTTACAG | ACGAGATACA | GAGAGAAAGG | GA......GA |
| Hid_D.moj | AAGATAAAAT | CATTTCGCAG | ACGGCAAAGG | CAAAGAAAGG | GACGTAAAGA |

| | | | | | |
|---|---|---|---|---|---|
| Hid_D.sim | ....AAGCAA | TAT....... | .......TAT | TTGTGTAGCC | TAAGTGACAG |
| Hid_D.ere | ....AAGCAA | TAT....... | .......TAT | TTGTGTAGCC | TAAGTGACAG |
| Hid_D.mel | ....AAGCAA | TAT....... | .......TAT | TTGTGTAGCC | TAAGTGACAG |
| Hid_D.yak | ....AAGCAA | TAT....... | .......TAT | TTGTGTAGCC | TAAGTGACAG |
| Hid_D.pse | ....AAGCGA | TAGCCCAGAC | CCCCAGATAC | ATGTATACCC | AGATTCCAGA |
| Hid_D.ana | TATAGAGCAA | TATTATTTGA | ATAT.GATAT | AAGTGAGATA | CCACTTAAGT |
| Hid_D.vir | GTTGCCCACA | CA........ | .........T | ACAC.TAGTT | AATATAACAG |
| Hid_D.moj | GTTAGAGAAA | GAGAGAGAGA | GAGAGAAGAT | ACAC.TAGTT | AATGTAAACG |

| | | | | | |
|---|---|---|---|---|---|
| Hid_D.sim | TCCCAA...T | CAAATCAAAT | ......CCAA | TCCAATATCA | ..CCC..AGT |
| Hid_D.ere | TCCCAA...T | CAAATCCAAG | ......CCAA | TCCAATATCA | ..CCC..AGT |
| Hid_D.mel | TCCCAA...T | CAAATC.... | .......CAA | TCCAATATCA | ..CCC..AGT |
| Hid_D.yak | TCCCAA...T | CAAATCAAAT | ......CCAA | TCCAATATCA | ..CCC..AGT |
| Hid_D.pse | TCCCAGATCC | CAGACTCCAT | AT...CCTTA | TCCACTGCCA | ..GCCGCAGC |
| Hid_D.ana | ACCCAT.CAT | CAAATC.... | .......CAA | TCCAATCCCA | ..GCCA.GAT |
| Hid_D.vir | CAGCAAGCAG | CAAAGGTAGA | CAAAATTT.G | TTTATTATGA | ......TTTT |
| Hid_D.moj | CAGCAAGCAG | CAAAAGTAGA | GAAAATTTTG | TTTAATATTC | ATGTTTTTTT |

| | | | | | |
|---|---|---|---|---|---|
| Hid_D.sim | CCCGGA.... | ........CA | ATTCCCAGCA | AAACAA..TA | GACTATTTTC |
| Hid_D.ere | CCCGGA.... | ........CA | TTTCCCAGCA | AAACAA..TA | GACTATTTTC |
| Hid_D.mel | CCCGGA.... | ........CA | TTTCCCAGCA | AAACAA..TA | GACTATTCTC |
| Hid_D.yak | CCCGGA.... | ........AA | AATCCCAGCA | AAACAA..TA | GACTATTTTC |
| Hid_D.pse | CCCAGATATA | CATACATACA | CTTTCAAGCA | AAATAG..AA | CACTACACTT |
| Hid_D.ana | CCCAGA.... | CCATGACACA | CAATGAAATA | GAATATGCTT | TCTCGTACAT |
| Hid_D.vir | TTCTTACGTA | TTTTTTTTTT | ATACACATAC | CCATAA..TT | TGTAAACAAC |
| Hid_D.moj | TTCTTACGTA | TTTTTTTTTT | TTTTTTATTA | TTATA...CA | TACTTACATT |

| | | | | | |
|---|---|---|---|---|---|
| Hid_D.sim | GCGTACACAT | GTATCAATCT | TAATTTGAAT | TACCACAAAA | ....C..CAA |
| Hid_D.ere | GCGTTCACAT | GTATCAATCT | TAATTTGAAT | TACCACAAAA | ....C..AAT |
| Hid_D.mel | GCGTTCACAT | GTATCAATCT | TAATTTGAAT | TACCACAAAA | ....TGAAAT |

FIG. 6 Cont.

```
Hid_D.yak    GCGTTCACAT GTATCAATCT TAATTTGACA TACCACAAAA ....C..AAA
Hid_D.pse    CTCAACTTAT GAACTAATCA TGACACACAC ACACGCACA. ....CACACA
Hid_D.ana    ACCTGCCTAT GTATTAATCA TAATTTGAAT TATCACAAAC AAATCAAAAA
Hid_D.vir    TATTCCACAC ACC.CAAAAA CAAAAACAAA AAAAAAAAAA A...AACAAA
Hid_D.moj    TAATTTGTAT ACAACTATTC CAAGCCCCCA ACCCAAAAAA A...AAAAAA Hid_D.sim    GAA.ATACTC CAACCATAC. CCAAATGAAA AATTATTTTT GTAAATTGTT
Hid_D.ere    GAA.ATACTA CAACCATAC. CCAAATGAAA AATTATTTTT GTAAATTGTT
Hid_D.mel    GAA.ATACTA AAACCATAC. ACAAATGAAA AATTATTTTT GTAAATTGTT
Hid_D.yak    GAA.ATACTC CAACCACAC. CCAAATGAAA AATTATTTTT GTAAATTGTT
Hid_D.pse    CAA.ACACCA CTTCCAAAAA CCCAATGAAA AATTAATTTT GTAAATTTGT
Hid_D.ana    CAGTACAATA CTTCCAAAAA CCCAATGAAA AATTATTTTT GTAAATTTTT
Hid_D.vir    AACGAAAAAA ATCACAAAAA ATCTATGAAA A....TTTTT GTAAATTTTT
Hid_D.moj    AACAAAACAA ..CA.AAAAA CTCAATGAAA A....TTTTT GTAAATTTTT Hid_D.sim    T..GCATCAA GTGAGCA.GG G........G GTTAAACTAA GGAAC.....
Hid_D.ere    T..GCATCAA GTGAGCA.GG G........G ATTAAATTAG GGAAA.....
Hid_D.mel    T..GCATCAA GTGAGCAAGG G........G ATTAGATTAA GGAAT.....
Hid_D.yak    T..GCATCAA ATGAGCA.GG G........G GTTGAACTAA GGAAC.....
Hid_D.pse    T..GCATCAA ATGAACC.GG .......... ...AAACGGC GGGAG.....
Hid_D.ana    TT.GCATCAA ATGAACCGGG AT.......G GCCAAGACAG TTTAA.....
Hid_D.vir    CTAAAATGAA CTCAACGCAA AG...TTGTC ATTGGCC..A GCAAA.....
Hid_D.moj    CTAAAATGAA CTCAACGCAA ATATTCTGTC ACCGACCGCA GCGAAGGAGC Hid_D.sim    ......CATC CTTGCTT... .......... .......TAT CCTCTGC
Hid_D.ere    ......TATC CTTGCTT... .......... .......TAT CCCCTGC
Hid_D.mel    ......CATC CTTGCTT... .......... .......TAT CCCCTGC
Hid_D.yak    ......CATC CTTGCTT... .......... .......TAT CCCCTGC
Hid_D.pse    .........C CTGTCTT... .......... .......CCC CTCTGGT
Hid_D.ana    ......GATT ATTTCTTA.. .......... .AAGCTACCT TCCTGGT
Hid_D.vir    .ATT...GTT GTGTTTTG.. TTGCCAGTGC CCAGCGCCAG CGATGGT
Hid_D.moj    AATTTGCATT GCTCTTTGCC TTGGGAGTGG CAGAAGTTGG CGCCGAT Bantam                            GTGAAAGTTT        G
Hid_D.sim    TTATTGCTAAT AGTTTTCACGA        GTAAAGTTTTGT GGCCTTGC..
Hid_D.ere    TTATTGCTAAT AGTTTTCACGA        GTAAAGTTTTGT GGCCTTGC..
Hid_D.mel    TTATTGCTAAT AGTTTTCACAA        GTAAAGTTTTGT GGCCTTGC..
Hid_D.yak    TTATTGCTAAT AGTTTTCACGA        GTAAAGTTTTGT GGCCTTGC..
Hid_D.pse    TCATTGCCAAT AGTTTTCACAA        GTAAAGTTTTGT GGCCTCGCAG
Hid_D.ana    TCATTGCTAAT AGTTTTCACAA        GTAAAGTTTTGT GGCCTAGC..
Hid_D.vir    TCATT.CTAAT AGTTTTCACAA        GTAAAGTTTTGT GGCCGCGC..
Hid_D.moj    TCATT.CTAAT AGTTTTCACAT        GTAAAGTTTTGT GGCCGCGC..
                     *  *           *
                            Site IV
```

FIG. 6 Cont.

```
Hid_D.sim    .GCCCAAAAG TCG....... ..TAAAGATT TTTGGTTTGC CATAAATACT
Hid_D.ere    .GCCCAAAAG TCG....... ..TACAGATT TTTGGTTTGC CATGAAAACT
Hid_D.mel    .GCCCAAAAG TCG....... ..TACAGATT TTTGGTTTGC CATAAATACT
Hid_D.yak    .GCCCAAAAG TCG....... ..TACAGATT TTTGGTTTGC CATAAATACT
Hid_D.pse    GGCCCAGAAG TCAACATGGA AACATTGATT TCTGGCCTGC CATGAATACT
Hid_D.ana    .GCCCAGAAG TCGAC..... ..AACAAGAT TTTTGGTTGC CATAAATACT
Hid_D.vir    .GCCCAAAAG TCA....... ...ACAAGAT TTTTGGTTGC CATAA..ACT
Hid_D.moj    .GCCCAGAAG TCA....... ...TCAAGAT TTTTGGTTGC CATAA..ACT Hid_D.sim    CGAACAAAAA .GTTAAAGAA AAAC.GAAGC AAATGGAAAA ........AA
Hid_D.ere    CGAACAAAAA .GTTAAAGAA AAAC.GAAGC AAATGGAAAA ........AA
Hid_D.mel    CGAACAAAAA .GTTAATGAA AAAC.GAAGC AAATGGAAAA ........AA
Hid_D.yak    CGAACAAAAA .GTTAAAGAA AAAC.GAAGC AAATGGAAAA ........AA
Hid_D.pse    GGAACAAAAA .GTTAAAGGA AAGCAGAAGC AGAAGCAGAA GCAGTAGCAG
Hid_D.ana    CGAACAAAAA AGTTAGAGAA AAAC.GAAGC AAAAGGAACA A......GTA
Hid_D.vir    GAAACAAGGC AGAAA..... AGCAAGAAAC AAAA.....A TAAA...ATG
Hid_D.moj    GAAGCAAGGC AGAAAGAACA AGCAAGAAAC AAAATATATA TCAA...ATG Hid_D.sim    A.TCAGAAT. .GAAACACAA GAAATTTATA TTTTTGACCC AATGCTACTT
Hid_D.ere    A.TCAGAAT. .GAAACACAA GAAATTTATA TTTTTGACCC AATGCTACTT
Hid_D.mel    AATCAGAAT. .GAAACACAA GAAATTTATA TTTTTGACCC AATGCTACTT
Hid_D.yak    A.TCAGAAT. .GAAACACAA GAAATTTATA TTTTTGACCC AATGCTACTT
Hid_D.pse    AAGCAGAATC AGAAGCAAAA GCAAACTATA TTTTTGACCC GATGCGACTT
Hid_D.ana    AATCAGAAT. ACATGAAATT TATATACATA CGTTTCACCC AATGCGACTT
Hid_D.vir    AATCACATA. .GCGAAAA.. ..TTTGTTTA TTTT..ATTC CATGCGA...
Hid_D.moj    AATCACATA. .GCGACAAAT TTTTTGTTTA TTTTCTATTC CATGCGACGT Hid_D.sim    AATCCGTTTT T......... ....TAATTT AAGTATCTT. TACTCGACCT
Hid_D.ere    AATCCGTTTT T......... ....TAATTT AAGTATCTT. TACTCGACCT
Hid_D.mel    AATCCGTTTT TG........ ....TAATTT AAGTATCTT. TACTCGACCT
Hid_D.yak    AATCCGTTTT T......... ....TAATTT AAGTATCTT. TACTCGACCT
Hid_D.pse    GATCCGTTTG TT........ ....AAATTT AAGTATCTT. TACTCGACCC
Hid_D.ana    AATCCGTTTT TGTTTTTTAT TTGTAAATTT AAGTATCTC. TACTCGACCT
Hid_D.vir    ACTTCCGACA T......... ....TAAATT AAGTAATTCG TAA.......
Hid_D.moj    ACTTCCGACC T......... ....AAAATT AAGTAATTCG TAAATTCGTA Hid_D.sim    ...TGTATAT AGCGC..AGT TCGAATCACA GAA.TC.AAA TGCCATTTTT
Hid_D.ere    ...TGTATAT AGCGC..AGT TCGAATCACA GAA.TC.AAA TGCCATTTTT
Hid_D.mel    ...TGTATAT AGCGC..AGT TCGAATCACA GAA.TC.AAA TGCCATTTTT
Hid_D.yak    ...TGTATAT AGCGC..AGT TCGAATCACA GAA.TC.AAA TGCCATTTTT
Hid_D.pse    ...TGTACAT AGCGCGCAGT TCGAATCATA GAA.TC.AAA TGCCATTTTT
Hid_D.ana    ACTTGTATAT AGTGC..AGT TCGAATCATA GAA.TC.AAA TGCCATTTTT
Hid_D.vir    .......... .....TTTGT ATATAGCGCA AAAATC.AAA TGCCATTTT.
Hid_D.moj    ACTCGTAATT TGTAATTTGT ATATATCGCA AAAATCGAAA TGCCATTTTT
```

FIG. 6 Cont.

```
Hid_D.sim    ....GTATAG AATTTCGTTT GGTGCCAAAA CAGTGACAGA TAATT.....
Hid_D.ere    ....GTATAG AATTTTGTTT GGTGCCAAAA CAGTGACAGA TAATT.....
Hid_D.mel    ....GTATAG AATTTTATTT GGTGCCAAAA CAGTGACAGA TAATTA....
Hid_D.yak    ....GTATAG AATTTTGTTT GGTGCCAAAA CAGTGACAGA TAATT.....
Hid_D.pse    ....GTATAG AATTTTGTTT GGTGCCAAAA CAGTGACAGA TAATTGTCTG
Hid_D.ana    TTGTGTATAG AATTTTGTTT GGTGCCAAAA TATGAAGAGA TAT.......
Hid_D.vir    ....GTATAG A....TTGTT GGTGCCAAAA CAGTGA.AAA TGTGTGTTAA
Hid_D.moj    T...GTATAG A....TCGTT GGTGCCAAAA CAGTTG.AAT TGTGTGTTAA Hid_D.sim    ....GTCTAT GAA.CCCGTG TATTT.CGCA TAT.TATACA T.TTATACAT
Hid_D.ere    ....GTCTAT GAA.CCCGTG TATTT.CGCA TAT.TATACA T.TTATACAT
Hid_D.mel    .AATGTCTAT GAA.CCCGTG TATTT.CGCA TAT.TATACA T.TTATACAT
Hid_D.yak    ....GTCTAT GAA.CCCGTG TATTT.CGCA TAT.TATACA T.TTATACAT
Hid_D.pse    CGACACACAC ACA.CACACA CACACACACA CACGCATACA CATTATACAT
Hid_D.ana    ....GAGCGC GTA.TATTTG AATAC...TA TACCAGTACA TATAATACAT
Hid_D.vir    ATATGTGCTG CCAATTTTTC TTATTGAAAG CTGCGATGAA C.ACATATTC
Hid_D.moj    ACA.GTGTAG GA......TG GAGCTGCCAG CAACGG.GAG T.TCGCATTG Hid_D.sim    A......... ...TATCGTA ACTTCAATGA ..TAAGTTTG A....TTCTG
Hid_D.ere    A......... ...TATTGTA ACTTCAATGC ..TAAGTTTG A....TTCTG
Hid_D.mel    A......... ...TATCGTA ACTTCAATGA ..TAAGTTTG A....TTCTG
Hid_D.yak    A......... ...TATCGTA ACTTCAATGA ..TAAGTTTG A....TTCTG
Hid_D.pse    AATAGAATTT ATTTATCCTA AGCTCGATCC ..TAAGTTCA ACA.ATTCAG
Hid_D.ana    A......... ...TATCGTA ACTTCAATCA ..TA...TAG G....TTTCT
Hid_D.vir    AAAC.....T TAC.ATAACT TCAATTACGT .TTAGACTTA AG..TCCCCA
Hid_D.moj    AGAG.....C TGCCATCGTA ACACTTACGC ATTCGATTCA AAACTCCCAA Hid_D.sim    AAATTTTT.. .GTCAACTCA ATTTAAGAAA CA.TTTCTGT TGTAGTTTAG
Hid_D.ere    AAATTTT... .GTCGACTCA GTTTAAGAAA CA.TTTCTGT TGTAGTTTAG
Hid_D.mel    AAATTTT... .GTCAACTCA ATTTAAGAAA CA.TTTCTGT TGTAGTTTAG
Hid_D.yak    AAATTTT... .GTCAACTCA ATTTAAGAAA CA.TTTCTGT TGTAGTTTAG
Hid_D.pse    CAATTTGTCA ATTCAATTCA ACTTAGGAAA TA.ATCCTCT TTTTTTTTGT
Hid_D.ana    TGATTCG... ..TCAATCCA ATTTAAGAAT TAATTTCTGT TTATGTTTTG
Hid_D.vir    TTATTTTCAA TATGTATTCT TAAATAAAAA TG.CATATAT CAATATGTGT
Hid_D.moj    TTATAAATAG AGTTAAGCTC CCCCTTAAAA TA.T...TTT CAATATGTAT Hid_D.sim    TGATC..... GCCGGCAGAA AGC.....AC TTTGTTTAA. TTGTACATTT
Hid_D.ere    TGATT..... GCTAGCAGAA AGC.....AC TTTGTTTAA. TTGTACATTT
Hid_D.mel    TGATT..... GCTAGCAGAA AGC.....AC TTTGTTTAA. TTGTACATTT
Hid_D.yak    TGATTT.... GCTAGCAGAA AGC.....AC TTTGTTTAA. TTGTACATTT
Hid_D.pse    TGTTTTTCGT GTTCGGAAGA AGCGCAAGAC TTCGTTTAA. TTGTACATTT
Hid_D.ana    TGTTC..... .TTCGGAAGC AGG..AAAAT ATTGTTTAAC TTGTACATTT
```

FIG. 6 Cont.

```
Hid_D.vir    TATTCTTTGT GTAAAGCTCA AGC..GAACG CACATATATC TTGTACATTT
Hid_D.moj    TTTTCTGTGT GTGGG....A ACA..CAACA TTTATACAAC TTGTACATTT Bantam                           ...CCA                    A.GT...
Hid_D.sim    TATAT..TATGCTG..A.................ATT.TA.T.TA...
Hid_D.ere    TATAT..TATGCTG..................ATT.TA.T.TA...
Hid_D.mel    TATAT..TATGCTG..................ATT.TA.T.TA...
Hid_D.yak    TATAT..TATGCTG..................ATT.TA.T.TATA.
Hid_D.pse    TATATATTATGCTG..................ATT.TA.T.TGCA.
Hid_D.ana    TATAT..TATGTGG..................ATT.TA.T.TA...
Hid_D.vir    TATCT..TATGCTG...AATTTA.ATATATATAAAGATATA.GT.T.TATA.
Hid_D.moj    TATCT..TATGCTG..TTAATATATATATATATATATATA.AT.T.TAAAA
                             *  *      (2 large spacers:26 & 33bp)

Bantam
Hid_D.sim    ............CATA.AATATCATTAT........GAATATGTTCATAAGAC
Hid_D.ere    ............CATA.AATATTATTAC........GAATATGTTCATAAGAC
Hid_D.mel    ............CATA.AATATCATTAT........GAATATGTTCATAAGAC
Hid_D.yak    ............CATA.AATATCATTAC........GAATATGTTCATAAGAC
Hid_D.pse    ............TAAATAATATCATTAT........GAATATGTTCATAAGAC
Hid_D.ana    ............CATA.AATATCATTAC........GAATATGTTCATAAGAC
Hid_D.vir    ..........TATATCTTATATCACTA.........GAATATGTTCATAAGAC
Hid_D.moj    GAATATATAAATATATAAAATATCACTA.........GAATATGTTCATAAGAC
                                                *
                              Site V Hid_D.sim    AACAAAAATT ATATATAT.G AATACATCTA TGTGTATGTG
Hid_D.ere    AACAAAAATT ATATATAT.G AATACATCTA TGTGTATGTG
Hid_D.mel    AACAAAAATT ATATATAT.G AATACATCTA TGTGTATGTG
Hid_D.yak    AACAAAAATT ATATATAT.G AATACATCTA TGTGT.....
Hid_D.pse    AAAATAAGCA GCAACAA... ..........
Hid_D.ana    AACAACAATT ATAAATAT.A TATAAATATG AATAAATCT.
Hid_D.vir    AAAAGTATAT ATGTAAATGA AAAACA.ATA CA.AAACGCA
Hid_D.moj    GAAAGTATAT ATGTAAATTA AATAAATACG CATAAATATA
```

FIG. 6 Cont.

```
miR-196b                         G                                    
HOXB8_HS    UUCUGCUAAGUUCUC                                    UUCACGCC
HOXB8_MM    UUCUGCUAAGUUUUC                                    UUCACGCC
HOXB8_RN    UUCUGCUAAGUUUUC                                    UUCACGCC
HOXB8_XL    AAAACAAAAGACAAA                                    AUUGAGAU
HOXB8_DR    AAAUUACUGA--CUU                                    UUUAUGCC
HOXB8_TR    CAAUUAAUGAAAUUU                                    UUUAUGCC
                                                *
```

FIG. 6 Cont.

```
myotrophin_MM    AAGTATCCTAGTTCATGTACATCC...GAAT.GCTAACTAATACTGTGTT
myotrophin_RN    AAGTATCCTAGTTCATGTACATCC...GAAT.GCTAACTAATACTGTGTT
myotrophin_GG    ...TATCATGGTTCATAGACATCA...GAAT.GCAAAATGATACTGTATT
myotrophin_BT    ...TATCCTAGTTCATGTACATCA...GAAT.GCTAAATAATACTGTGTT
myotrophin_HS    AAGTATCCTAGTTCATGTACATCC...GAAT.GCTAAATAATACTGTGTT
myotrophin_PT    AAGTATCCTAGTTCATGTACATCC...GAAT.GCTAAATAATACTGTGTT
myotrophin_XL    TAATATTTT.GTTAATAGGCTTCCTATAATC.GCCAGTAGCTCCTCCGGC
myotrophin_DR    GAATTTCCC.TTCACTCCGCTTCCCTCCTCCAGCGCTCCGACATTCCCGT miR-375                  AGUCCGCUCGGCUUGC
myotrophin_MM    TA.AGTTTCGTG..TTGCAAG          .....TGGAAT....AAACTTGA
myotrophin_RN    TA.AGTTTCGTG..TTGCAAG          .....TGGAAT....AAACTTGA
myotrophin_GG    TTTAAGTTTGTG..TTGCAAG          .....TGGAAT....AAACTTGA
myotrophin_BT    TA.AGTTTCGTG..TTGCAAG          .....TGGAAT....AAACTTGA
myotrophin_HS    TTAAGTTTTGTG..TTGCAAG          .....TGGAAT....AAACTTGA
myotrophin_PT    TTAAGTTTTGTG..TTGCAAG          .....TGGAAT....AAACTTGA
myotrophin_XL    CACACTCGCATTCATGTCAAT          AAGGCTGAATT....AAATCTGA
myotrophin_DR    CACA.TTGAAGATGCTCAAAG          TA..TTAGACTTCAGACGCTCGA
                          *               ** *
                                   Site I
```

FIG. 6 Cont.

Supp. Fig. 3

```
miR-1      AUGUAUGAAGAAA               U
DR:  GACAUUGGAUAUUUGAGG..........AAAAAC      UUU
GG:  AAAUGUGGAUAUUUGAAGGAGAGGGGAAAAAAG.      UAG
SS:  AAAAGUGGAUAUUUGAAG..........AAAAG.      UAU
MM:  AAAGGUGGAUAUUUGAAG..........AAAAG.      UAU
RN:  AAA.GUGGAUAUUUGAAG..........AAAAG.      UAU
PT:  AAA.GUGGAUAUUUGAAG..........AAAAG.      UAU
HS:  AAA.GUGGAUAUUUGAAG..........AAAAG.      UAU
          *   *
         miR-1 complementary to Hand2 3'UTR miR-1       AUGUAUGAAGAA
CL:  GCGCCGCCAAUAUGCA.CUG       CAAGCAUUGC
XL:  AUCACCCCAAUAUGCA.CUG       CAAGCAUUGC
GG:  CCUUCCAAAUUAUGCA.CUG       CAAGCAUUGC
ME:  GCCCUGCCAAUAUGCA.CUG       CAAGCAUUGC
BT:  GCGCCGCCAGUAUGCA.CUG       CAAGCAUUGC
MM:  GCGCCGCCAAUAUGCA.CUG       CGAGCAUUGC
RN:  GCGCCGCCAAUAUGCA.CUG       CGAGCAUUGC
PT:  GCGCCGCCAAUAUGCA.CUG       CAAGCAUUGC
HS:  GCGCCGCCAAUAUGCA.CUG       CAAGCAUUGC
          *   *
         miR-1 complementary to TB4 3'UTR miR-1            AUGUAUGAAGAAA
MM:  GGGCAUUCCCCCAAUGAAAUAUACAAGUAA       ACA
EC:  GGGCAUUCCCCCAAUGAAAUACACAAGUAA       ACA
PT:  GGGCGUUCCCCCAAUGAAAUACAUAAGUAA       ACA
HS:  GGGCGUUCCCCCAAUGAAAUACACAAGUAA       ACA
SS:  GGGCAUUCCCCCAGUGAAAUAUACAAGUAA       ...
CH:  GGGCAUUCCCCCAAUGAAAU....AAGUAA       ACA
BT:  GGGCAUUCCCCCAAUGAAAU....AAGUAA       ACA
OA:  GGGCAUUCCCCCAAUGAAAU....AAGUAA       ACA
SC:  GGGCAUU.CUCCCAGUGAACAAUGCAACUAA      AUA
GG:  GGGCAUU.CUCCCACUGAACAAUGCAACUAA      AUA
XL:  GGGCAUU.CUCCCUCUAAACAAUUCAAAUAC      AUG miR-1 complementary to IGF1 3'UTR
```

FIG. 7

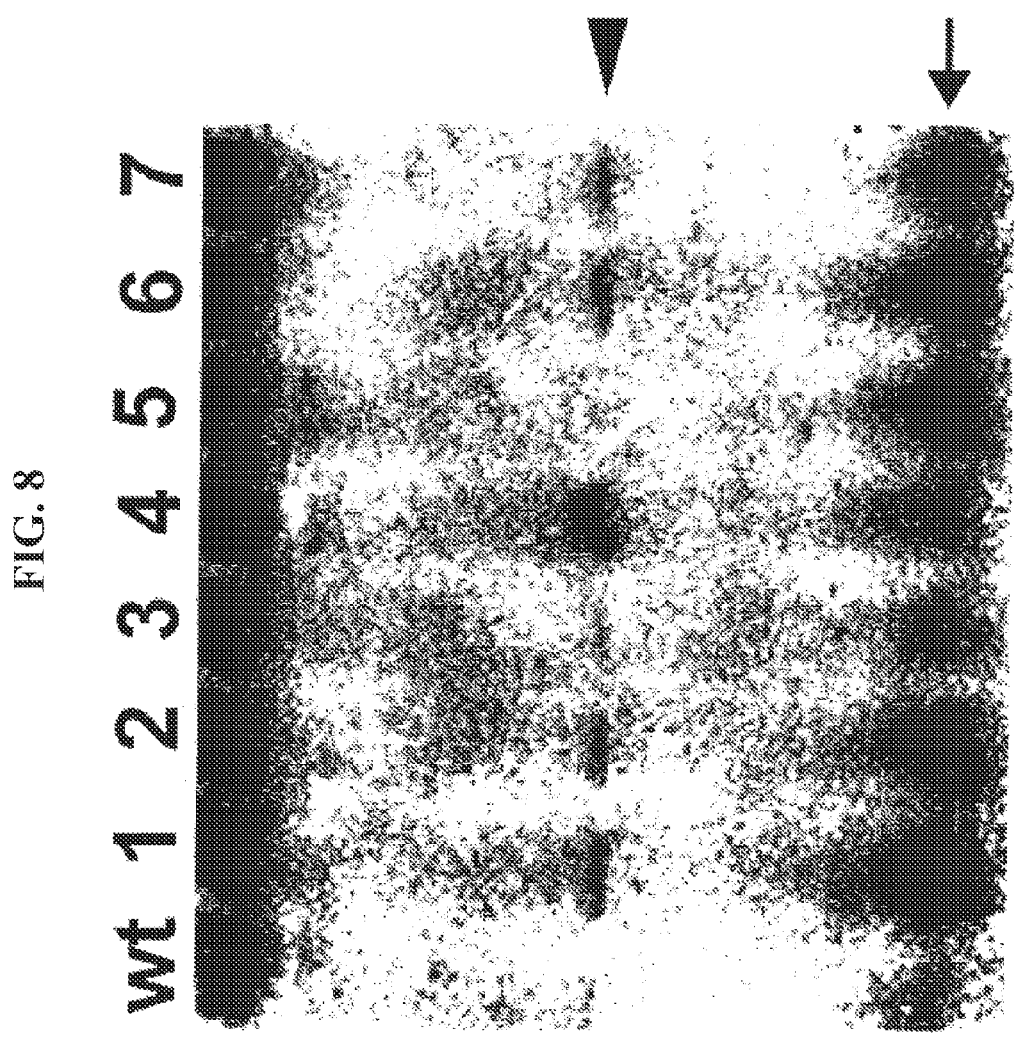

MICRO-RNA'S THAT REGULATE MUSCLE CELLS

This application is a division of U.S. application Ser. No. 11/397,961, filed Apr. 4, 2006, which issued as U.S. Pat. No. 8,592,384 and claims benefit of priority to U.S. Provisional Application Ser. No. 60/668,187, filed Apr. 4, 2005, each of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_018_02US_SeqList_ST25.txt, date recorded: Jan. 13, 2014, file size 70 kilobytes).

BACKGROUND OF THE INVENTION

1. Field of the Invention

The present invention relates to fields of molecular and developmental biology. More particularly, the present invention relates to microRNAs that regulate differentiation, proliferation and death of cardican and skeletal muscle cells.

2. Description of Related Art

Cellular differentiation and organogenesis involve restricted zones of transcriptional regulation that govern gene expression patterns during specific temporal windows. One mechanism for regulating the target genes activated by transcriptional regulators involves the dose-sensitive response of cis elements to gradients of DNA-binding proteins. In this scenario, variances in the levels of transcription factors result in the activation or repression of diverse target genes allowing finer control of the spatial and temporal events of organogenesis.

MicroRNAs (miRNAs) mediate a recently recognized form of translational inhibition that alters dosages of critical regulators and thereby provides a mechanism for temporospatial control of developmental and homeostatic events in a wide range of plant and animal life (He and Hannon, 2004; Ambros, 2004; Meister and Tuschl, 20040. Genetic studies in *Caenorhabditis elegans* and *Drosophila melanogaster* suggest important functions for specific miRNAs in cell death and proliferation decisions through direct interaction of miRNAs with target sequences in messenger RNAs (Lee et al., 1993; Wightman and Ruvkun, 1993; Moss et al., 1997; Brennecke et al., 2003; Abrahante et al., 2003; Johnston and Hobert, 2003; Vella et al., 2004; Chang et al., 2004). However, an understanding of the specific roles and regulatory pathways controlled by mammalian miRNAs has been limited by the lack of reliable and specific methods to identify miRNA targets.

The transcriptional regulation of cardiomyocyte differentiation and cardiogenesis is highly conserved and requires sequential activation or repression of genetic programs (Chien and Olson, 2002; Srivastava and Olson, 2000). Early during heart formation cardiomyocytes proliferate even as they begin to differentiate, however they soon exit the cell cycle as differentiation progresses. Serum response factor (SRF) binds to CArG boxes in the regulatory region of numerous muscle-specific and growth-regulated genes and thus has a dual role in regulating the balance between proliferation and differentiation during cardiogenesis, in part through interaction with tissue-specific co-factors (Norman et al., 1988; Miralles et al., 2003; Shin et al., 2002; Chen et al 2002). Failure to maintain an adequate pool of undifferentiated myocyte precursors could result in organ hypoplasia as is observed in zebrafish that lack the transcription factor, Hand2 (Yelon et al., 2000). In this case, the ventricular pool of cardiomyocytes is greatly diminished, similar to the defect in ventricular expansion observed in mice lacking Hand2 along with its relative, Hand1 (Srivastava et al., 1995; Srivastava et al., 1997; Firulli et al., 1998; Yamagishi et al., 2001; McFadden et al., 2005). While dynamic temporal and spatial expression of regulatory pathways is important in cardiogenesis, whether microRNAs are involved in refining cardiac transcriptional activity is unknown.

SUMMARY OF THE INVENTION

Thus, in accordance with the present invention, there is provided a nucleic acid comprising a sequence selected from the group consisting of SEQ ID NOS:1-18. Also provided is a nucleic acid consisting of a sequence selected from the group consisting of SEQ ID NOS:1-18, and may further be selected from the group consisting of SEQ ID NOS: 4, 5, 7, 9, 10, 14, 15, 17 and 18. The nucleic acid may be a DNA or an RNA.

In another embodiment, there is provided an expression cassette comprising an enhancer region selected from the group consisting of SEQ ID NOS:14, 15, 17 and 18. The expression cassette may comprise a nucleic acid segment comprising a sequence selected from the group consisting of SEQ ID NO:4, 5, 7, 9, and 10. A host cell comprising these expression cassettes also is contemplated. The expression cassette may be integrated into the host cell genome or episomal to the host cell genome. The expression cassette may comprise an origin of replication, and may be a viral or non-viral expression construct. The viral expression construct may be an adenovirus, a retrovirus, a pox virus, an adeno-associated virus, a polyoma virus or a herpesvirus. The host cell may be a muscle cell, for example, a skeletal muscle cell, a cardiac cell, or muscle progenitor cell, such as a stem cell.

In yet another embodiment, there is provided a method of modulating the proliferation, differentiation or death of a muscle cell comprising contacting said cell with a miR-1-1, miR-1-2, or miR-133 nucleic acid. Contacting may comprise providing an miRNA to said cell, or providing an expression construct encoding miR-1-1, miR-1-2, or miR-133a2 to said cell. The muscle cell may be a skeletal muscle cell, a cardiac muscle cell, or muscle progenitor cell, such as a stem cell. The cell may be located in an animal subject, such as a human, or the cell may be contacted in vitro, wherein the method may comprise further culturing of said cell.

In still yet another embodiment, there is provided a method of modulating the proliferation, differentiation or death of a muscle cell comprising contacting said cell with an agent an antagonist of miR-1-1, miR-1-2, or miR-133a2 function or expression. The muscle cell is may be muscle progenitor cell, such as a stem cell, a skeletal muscle cell or a cardiac muscle cell. The cell may be contacted in vitro, wherein the method may comprise further culturing of said cell. The agent may be a peptide, protein, DNA, RNA, antisense DNA, antisense RNA or small molecule.

In a further embodiment, there is provided a method of inhibiting differentiation of a muscle cell progenitor comprising inhibiting the function of one or more of miR-1-1, miR-1-2, or miR-133a2. Inhibiting the function may comprises contacting the cell with one or more modified or unmodified antisense constructs directed to one or more of miR-1-1, miR-1-2, or miR-133a2

In still a further embodiment, there is provided a method of inducing differentiation of a muscle cell progenitor comprising providing to said cell an agonist of miR-1-1, miR-1-2, or miR-133a2. The agonist may be miR-1-1, miR-1-2, or miR-133a2. The agonist may also be an expression cassette encoding miR-1-1, miR-1-2, or miR-133a2. The agonist may be a peptide, protein or nucleic acid that stimulates the expression of miR-1-1, miR-1-2, or miR-133a2. The agonist may be a serum response factor, myocardin, or an expression cassette encoding therefor. The cell may be located in an animal subject, such as a human, or the cell may be contacted in vitro, followed by culturing said cell in vitro. The method may further comprising, prior to contacting in vitro, obtaining said cell from an animal subject.

In still yet a further embodiment, there is provided a method of screening a candidate substance for an effect on muscle cell proliferation, differentiation or death comprising (a) providing a cell that expresses miR-1-1, miR-1-2, or miR-133a2; (b) contacting said cell with said candidate substance; and (c) assessing the effect of said candidate substance on the expression or stability of miR-1-1, miR-1-2, or miR-133a2, wherein a candidate substance that modulates the expression or stability of miR-1-1, miR-1-2, or miR-133a2 is a modulator of muscle cell proliferation, differentiation or death. The cell may be a muscle cell progenitor, such as a stem cell, a cardiac muscle cell or a skeletal muscle cell. Assessing may comprise measuring the cellular level or turnover of a miR-1-1, miR-1-2, or miR-133a2.

In another embodiment, there is provided a method of screening a candidate substance for an effect on muscle cell proliferation, differentiation or death comprising (a) providing a cell that carries an expression cassette under the control of a enhancer region selected from the group consisting of SEQ ID NOS:14, 15, 17 and 18; (b) contacting said cell with said candidate substance; and (c) assessing the effect of said candidate substance on the expression of a product under the operational control of said enhancer, wherein a candidate substance that modulates the expression of said product is a modulator of muscle cell proliferation, differentiation or death. The product may be a screenable marker gene, such as an enzyme, a chemilluminescent protein or a fluorescent protein. The cell may be a muscle cell progenitor, such as a stem cell, or muscle cell, such as a cardiac muscle cell or a skeletal muscle cell.

A yet another embodiment, there is provided a method for identifying an inhibitory RNA sequence comprising (a) searching databases for mRNAs having a complete match at the 5' eight base pairs; (b) further searching for additional mRNAs with a G/U wobble at the eighth position; (c) identifying mRNAs with corresponding homologues in at least two of the following genomes: chick, human, mouse and rat; (d) analyzing local mRNA second structure and selecting those mRNA with instability in the adjacent flanking regions; and (e) assessing stabilizing and destabilizing elements in said matched sequence, whereby an mRNA identified according to steps (a)-(e) is an inhibitory RNA. Step (c) may comprise identifying mRNA with corresponding homologues in all of chick, human, mouse and rat. Step (d) may comprise assessing local mRNA secondary structure 50 to 100 base pairs 5' and/or 3' to said matched sequence, or assessing local mRNA secondary structure about 70 base pairs 5' and/or 3' to said matched sequence.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-E—miR-1s are highly conserved and cardiac- and skeletal muscle-specific. (FIG. 1A) Sequence alignment of predicted miR-1s from species indicated. The eight 5' nucleotides are highlighted in red; non-conserved residues indicated in green (Worm miR-1, SEQ ID NO. 19; Fly miR-1, SEQ ID NO. 20; Frog miR-1, SEQ ID NO. 21; Zebrafish miR-1, SEQ ID NO. 22; Chick miR-1-1, SEQ ID NO. 23; Chick miR-1-2, SEQ ID NO. 24; Mouse miR-1-1, SEQ ID NO. 25; Mouse miR-1-2, SEQ ID NO. 26; Rat miR-1, SEQ ID NO. 27; Chimp miR-1-1, SEQ ID NO. 28; Chimp miR-1-2, SEQ ID NO. 29; Human miR-1-1, SEQ ID NO. 30; Human miR-1-2, SEQ ID NO. 31. (FIG. 1B) Multiple tissue Northern blot hybridized with miR-1-specific probe. Arrowhead indicates 70 bp unprocessed form and arrow indicates 21 bp miR-1. (FIG. 1C) Promoter region comparison between mouse and human. Percent conservation of a 4.6 kb or 10.7 kb genomic region around miR-1-1 or miR-1-2, respectively, between human and mouse using rVISTA. Embryonic expression of miR-1-1 (FIG. 1D) or miR-1-2 (FIG. 1E) marked by β-gal activity driven by genomic fragments indicated in (FIG. 1C) on whole-mount and sections. Note early inner curvature expression of miR-1-1 (arrowheads) and ventricular-specific expression of miR-1-2. v, ventricle; a, atrium; ot, outflow tract; s, somites; h, head; ht, heart; rv, right ventricle; lv, left ventricle.

FIGS. 2A-F—SRF, Mef2 and MyoD directly regulate miR-1 embryonic expression. Deletion and mutation analysis of upstream enhancers of miR-1-1 (FIG. 2A) or miR-1-2 (FIG. 2B). Summary of effects of mutations (*) on cardiac or somitic expression is indicated. Representative images are shown with construct numbers indicated. (FIGS. 2C-D) Electromobility shift assay using radiolabeled probes for each respective binding site (arrowhead). Asterisk indicates supershift with antibody. Cross-species conservation of binding sites also shown with distance upstream of miR-1 indicated. FIG. 2C. SRF Assay: (Human miR-1-1 enhancer, SEQ ID NO. 32; Mouse miR-1-1 enhancer, SEQ ID NO. 33; Chick miR-1-1 enhancer, SEQ ID NO. 34; Fish miR-1-1 enhancer, SEQ ID NO. 35; Mef2 Assay: (Human miR-1-1 enhancer, SEQ ID NO. 36; Mouse miR-1-1 enhancer, SEQ ID NO. 37; Chick miR-1-1 enhancer, SEQ ID NO. 38. FIG. 2D. SRF Assay: (Human miR-1-1 enhancer, SEQ ID NO. 39; Mouse miR-1-1 enhancer, SEQ ID NO. 40; Chick miR-1-1 enhancer, SEQ ID NO. 41; MyoD Assay: (Human miR-1-1 enhancer, SEQ ID NO. 42; Mouse miR-1-1 enhancer, SEQ ID NO. 43; Chick miR-1-1 enhancer, SEQ ID NO. 44. (FIG. 2E) "-fold" activation of luciferase downstream of miR-1-1 enhancer in Cos1 cells by SRF and myocardin with or without point mutation in SRF site. (FIG. 2F) RT-PCR of miR-1-2 expression in hearts from mice heterozygous or homozygous null for SRF showing in vivo dependency on SRF for miR-1 transcription.

FIGS. 3A-G—miR-1 regulates pool of proliferating ventricular cardiomyocytes and ventricular expansion. (FIG. 3A) and (FIG. 3D) represent transverse sections of wild-type (wt) or β-MHC-miR-1 transgenic (tg) hearts, respectively, at E13.5. Boxed area shown in close-up in (FIG. 3B) and (FIG. 3E) with bar indicating narrowed width of compact layer in transgenic hearts. (FIG. 3C) and (FIG. 3F) represent immunohistochemistry with antibody specific to phosphohistone H3 to mark proliferating cells. Arrows indicate cells that are cycling. (FIG. 3F) Quantification of cycling cells demonstrated statistically significant decrease (*) in number of proliferating cells in miR-1 transgenic hearts. ra, right atrium; la, left atrium; rv, right ventricle; lv, left ventricle;

FIGS. 4A-E—Prediction and validation of miR-1 targets. (FIG. 4A) Algorithm for in silico prediction of microRNA candidates. (FIG. 4B) Putative targets of miR-1 based on sequence matching and crossspecies comparison. Predicted ΔG of 70 bp 5' and 3' flanking regions neighboring potential target sites is shown. Presence of stabilizing element (SE) or destabilizing element (DSE) in target sequence is also summarized. (FIG. 4C) Approach for testing transferability of miR-1 target sequence to luciferase reporter using multimerized copies of wild-type (SEQ ID NO. 45) or mutant (*) sequence (SEQ ID NO. 46). Successful expression of mutant form of miR-1 is shown. (FIG. 4D) Fold activity of luciferase under various conditions is shown using the 3' UTR target sequence of Hand2 from multiple species. Specific activity of the target was observed for all Hand2 UTR's and also for thymosin β4's target sequence. (FIG. 4E) Western blot of protein from ten-day old hearts overexpressing miR-1 with α-MHC promoter. Hand2 protein was decreased but thymosin β4 and IGF1 were unchanged, consistent with accessibility predictions. RNA transcripts of all were equal as seen by RT-PCR.

FIG. 6—Alignment of known microRNA targets from different species. MicroRNAs are aligned with their target sequences in 3' UTRs. Lin-4, SEQ ID NO. 47; Lin-14 CB, SEQ ID NO. 48; Lin-14 CE, SEQ ID NO. 49; Lin-14 CR, SEQ ID NO. 50; Lin-28 CE, SEQ ID NO. 51; Lin-28 CR, SEQ ID NO. 52; Lin-28 CV, SEQ ID NO. 53; Let-7, SEQ ID NO. 54; Lin-41 CE, SEQ ID NO. 55; Lin-41 CR, SEQ ID NO. 56; Lin-41 CB, SEQ ID NO. 57; daf-12 CB, SEQ ID NO. 58; daf-12 CR, SEQ ID NO. 59; daf-12 CE, SEQ ID NO. 60; Lin57 CR, SEQ ID NO. 61; Lin57 CB, SEQ ID NO. 62; Lin57 CE, SEQ ID NO. 63; Lsy-6 CE, SEQ ID NO. 64; Cog-1 CE, SEQ ID NO. 65; Cog-1 CB, SEQ ID NO. 66; Lsy-6 CB, SEQ ID NO. 67; miR-273, SEQ ID NO. 68; die-1 CE, SEQ ID NO. 69; die-1 CB, SEQ ID NO. 70; Bantam, SEQ ID NO. 71; Hid D.sim, SEQ ID NO. 72; Hid D.ere, SEQ ID NO. 73; Hid D.mel, SEQ ID NO. 74; Hid D.yak, SEQ ID NO. 75; Hid D.pse, SEQ ID NO. 76; Hid D.ana, SEQ ID NO. 77; Hid D.vir, SEQ ID NO. 78; Hid D.moj, SEQ ID NO. 79; miR-196b, SEQ ID NO. 80; HOXB8 HS, SEQ ID NO. 81; HOXB8 MM, SEQ ID NO. 82; HOXB8 RN, SEQ ID NO. 83; HOXB8 XL, SEQ ID NO. 84; HOXB8 DR, SEQ ID NO. 85; HOXB8 TR, SEQ ID NO. 86; miR-375, SEQ ID NO. 87; myotrophin MM, SEQ ID NO. 88; myotrophin RN, SEQ ID NO. 89; myotrophin GG, SEQ ID NO. 90; myotrophin BT, SEQ ID NO. 91; myotrophin HS, SEQ ID NO. 92; myotrophin PT, SEQ ID NO. 93; myotrophin XL, SEQ ID NO. 94; myotrophin DR, SEQ ID NO. 95; Conserved residues matching 5' (green) or 3' (grey) end of miRNA sequence are indicated in red lettering. G/U matching is indicated by asterisk (*).

FIG. 7—Conserved miR-1 target sites in Hand2, TB4 and IGF1 3' UTRs. Conserved residues matching 5' (green) or 3' (grey) end of miRNA sequence are indicated in red lettering. miR-1 complementary to Hand2 3'UTR: miR-1, SEQ ID NO. 6; DR, SEQ ID NO. 96; GG, SEQ ID NO. 97; SS, SEQ ID NO. 98; MM, SEQ ID NO. 99; RN, SEQ ID NO. 100; PT, SEQ ID NO. 101; HS, SEQ ID NO. 102. miR-1 complementary to TB4 3'UTR: miR-1, SEQ ID NO. 6; CL, SEQ ID NO. 103; XL, SEQ ID NO. 104; GG, SEQ ID NO. 105; ME, SEQ ID NO. 106; BT, SEQ ID NO. 107; MM, SEQ ID NO. 108; RN, SEQ ID NO. 109; PT, SEQ ID NO. 110; HS, SEQ ID NO. 111. miR-1 complementary to IGF1 3'UTR: miR-1, SEQ ID NO. 6; MM, SEQ ID NO. 112; EC, SEQ ID NO. 113; PT, SEQ ID NO. 114; HS, SEQ ID NO. 115; SS, SEQ ID NO. 116; CH, SEQ ID NO. 117; BT, SEQ ID NO. 118; OA, SEQ ID NO. 119; SC, SEQ ID NO. 120; GG, SEQ ID NO. 121; XL, SEQ ID NO. 122.

FIG. 8—Transgenic overexpression of (MHC-miR-1. Northern analysis of wild-type (wt) and several lines of αMHC-miR1 transgenic mice. Arrowhead indicates pre-miRNA1 while arrow points to 21 bp processed form. Highly expressing lines were used for subsequent analysis.

DESCRIPTION OF ILLUSTRATIVE EMBODIMENTS

Figure 5:
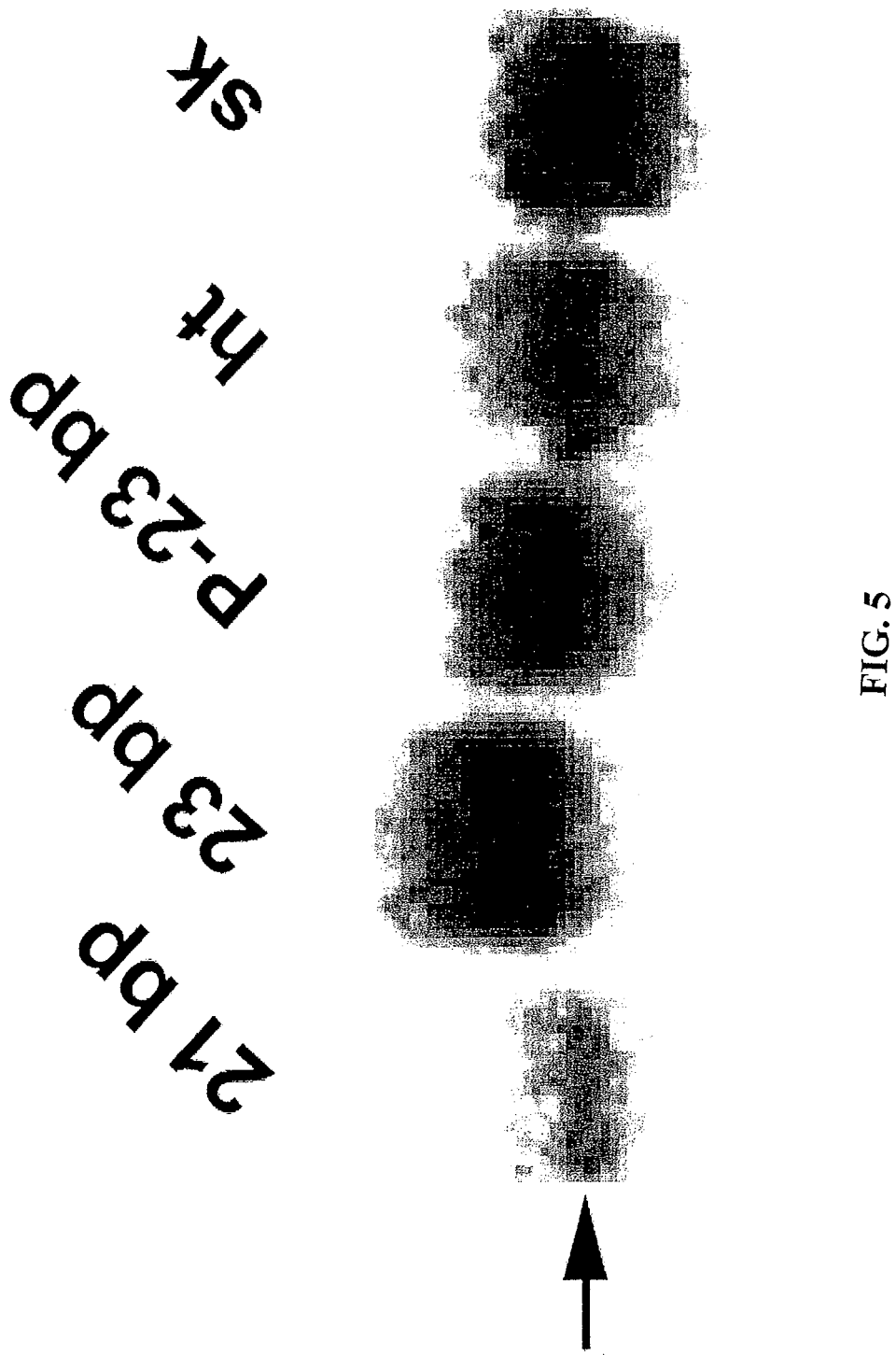
FIG. 5—Processed miR-1 is 21 bp in length. Northern analysis of synthesized miR-1 RNA of 21 bp, 23 bp, or phosphorylated 23 bp lengths, or RNA extracted from adult mouse heart (ht) or skeletal muscle (sk) hybridized to a miR-1 RNA probe. Endogenous miR-1 transcript migrates at same position as synthesized 21 bp form (arrow).

The present inventor has now shown that the cardiac and skeletal muscle-specific miRNAs, miR-1-1 and miR-1-2 are expressed in a chamber-specific fashion during cardiogenesis and are activated after initial cardiac specification and during the period of differentiation. He found that both genes were direct targets of SRF and its potent co-activator myocardin in the heart and were involved in negatively regulating ventricular cardiomyocyte proliferation (Wang et al., 2001). Further, the inventor provides evidence that RNA accessibility is a major feature of miRNA target recognition and incorporated this observation with cross-species sequence matching to identify Hand2 as an evolutionarily conserved target of miR-1. This work reveals a novel mechanism for regulation of the balance between muscle differentiation and proliferation during organogenesis and may provide a reliable and specific method for identification of microRNA targets.

The description of a conserved cardiac and skeletal muscle-specific regulatory pathway involving an miRNA that regulates translation of the central cardiac transcription factor, Hand2, represents the first identification of cis- and trans-regulatory components of an miRNA in vertebrates, and only the third vertebrate miRNA target validated by determination of effects on endogenous protein. The early exit of cardiomyocytes from the cell cycle upon overexpression of miR-1 may reflect its role downstream of SRF and myocardin to more finely regulate the balance between cell proliferation and differentiation. The potential role of miR-1s in mediating MyoD's role in skeletal muscle differentiation may be equally important and awaits future studies.

The highest levels of Hand2 mRNA transcripts are present at the earliest stages of cardiogenesis (E7.75), prior to heart tube formation, with transcript levels declining soon after cardiac looping (Srivastava et al., 1995; Srivastava et al., 1997). This observation, combined with loss-of-function effects in mice and fish, has suggested that Hand2 may be necessary for early expansion of the cardiomyocyte pool but may need to be downregulated as differentiation proceeds. The observation that miR-1 expression begins after cardiac looping and becomes robust only later is consistent with a model in which temporal regulation of Hand2 activity is necessary for cardiac differentiation. It is also interesting that miR-1-1 is initially only expressed in the inner curvature of the heart, but not the outer curvature where cellular expansion is necessary. Thus, miR-1s appear to both temporally and spatially regulate their targets, which likely contribute to multiple aspects of cardiogenesis.

This type of regulation may be a common method during embryogenesis to titrate the effects of critical signaling and transcriptional pathways to allow appropriate decisions of cell fate, proliferation and differentiation. The algorithm the inventor used to predict miRNA targets is based on observations from previously validated targets and an attempt to begin to develop certain "principles" that appear to be followed by known miRNAs and their targets (Lee et al., 1993; Wightman and Ruvkun, 1993; Moss et al., 1997; Brennecke et al., 2003; Abrahante et al., 2003; Johnston and Hobert, 2003; Vella et al., 2004; Chang et al., 2004; Yekta et al., 2004; Poy et al., 2004; Grosshans et al., 2005). The major difference between this approach and others is the additional evaluation of energy states of sequences flanking the miRNA target ($\Delta G$) and the presence or absence of SE/DSE in target RNA. Thus, the RNA secondary structure and resulting accessibility of the target sequence appears to be a major predictor of miRNA recognition. Consistent with this, ATP-assisted unwinding of RNA secondary structure does not seem to be involved in siRNA target recognition (Haley and Zamore, 2004; Doench et al., 2003). The inventor proposes a model in which miR-NAs preferentially target 3'UTR regions with less complex secondary structure.

1. MIR-1-1, MIR-1-2 AND MI-R-133A2 MICRORNA1

In accordance with the present invention, there is provided a series of related micro RNAs that constitute a family of conserved, muscle-specific RNAs that regulate the proliferation and differentiation of muscle cells, particularly skeletal and cardiac muscle cells.

In particular embodiments, the invention concerns isolated RNA and DNA segments and recombinant vectors incorporating DNA sequences that encode miR-1-1, miR-1-2, miR-133a2 (SEQ ID NOS:1, 4-12). These molecules may be provided as an isolated RNA, or a DNA or recombinant vector encoding such a non-coding RNA according to the present invention. As used herein, the term "nucleic acid" refers to a polymer of DNA, RNA or a derivative or mimic thereof, of sufficient length to encode a non-coding RNA or a portion thereof.

A. Oligonucleotides

The term "oligonucleotide" generally refers to a polymer of DNA, RNA or a derivative or mimic thereof, of between about 5 and about 100 bases in length. The term "polynucleotide" generally refers to a polymer of DNA, RNA or a derivative or mimic thereof, of greater than about 100 bases in length. Thus, it will be understood that the term "nucleic acid" encompasses both the terms "oligonucleotide" and "poly-nucleotide." These definitions may refer to single-stranded molecules, but also encompass double-stranded molecules, for example, when comprised within DNA vectors.

As used herein, the term "isolated RNA segment" refers to a RNA molecule that has been isolated free or substantially free of total RNA. Similarly, an isolated DNA segment encoding an ncRNA segment of the present invention refers to a DNA segment that has been isolated away from, or substantially purified free of, total genomic DNA. Included within the term "segment," are smaller fragments of such segments, and much larger molecules such as vectors, including, for example, plasmids; cosmids, phage, viruses, and the like. It will also be understood that nucleic acid sequences may include additional bases such as at the 5' and/or 3' sequences, so long as the sequence meets the criteria set forth above, including the maintenance of biological activity.

In addition to the "standard" DNA and/or RNA nucleotide bases, modified bases are also contemplated for use in particular applications of the present invention. A table of exemplary, but not limiting, modified bases is provided herein below.

TABLE 1

Modified Bases

| Abbr. | Modified base description |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl-2-thioridine |
| Cmnm5u | 5-carboxymethylaminomethyluridine |
| D | Dihydrouridine |
| Fm | 2'-O-methylpseudouridine |
| gal q | beta,D-galactosylqueosine |
| gm | 2'-O-methylguanosine |
| i | Inosine |
| i6a | N6-isopentenyladenosine |
| m1a | 1-methyladenosine |
| m1f | 1-methylpseudouridine |
| m1g | 1-methylguanosine |
| m1i | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| man q | beta,D-mannosylqueosine |
| mcm5s2u | 5-methoxycarbonylmethyl-2-thiouridine |
| mcm5u | 5-methoxycarbonyl-methyluridine |
| mo5u | 5-methoxyuridine |
| ms2i6a | 2-methylthio-N6-isopentenyladenosine |
| ms2t6a | N-((9-beta-D-ribofuranosyl-2-methyl-thiopurine-6-yl)carbamoyl)threonine |
| mt6a | N-((9-beta-D-ribofuranosylpurine-6-yl)N-methyl-carbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-beta-D-ribofuranosylpurine-6-yl)carbamoyl)threonine |
| tm | 2'-O-methyl-5-methyluridine |
| um | 2'-O-methyluridine |
| yw | wybutosine |

TABLE 1-continued

Modified Bases

| Abbr. | Modified base description |
|---|---|
| x | 3-(3-amino-3-carboxypropyl)uridine, (acp3)u |

It is contemplated that a nucleic acid fragment of the present invention may be almost any length. A general size range for the miRNAs themselves will be 20 to 90-100 bases. It will be readily understood that intermediate lengths, such as 21, 22, 23, 24, 25, 26, 27, 28, 29, 30, 31, 32, 33, 34, 35, 36, 37 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99, are contemplated as well.

Accordingly, the RNA sequences of the disclosure are used for their ability to selectively form duplex molecules with complementary stretches of target genes and/or mRNAs. In screening for related RNA molecules with inhibitory activity, the hybridization conditions will generally be selected to mimic those in in cyto environments. By way of reference, "stringent conditions" are those that allow hybridization between two homologous nucleic acid sequences, but preclude hybridization of random sequences. Hybridization at high temperature and/or low ionic strength is termed high stringency. In contrast, hybridization at low temperature and/ or high ionic strength is termed "low stringency," which permits hyridization of less related sequences. Low stringency is generally performed at 0.15 M to 0.9 M NaCl at a temperature range of 20° C. to 50° C. High stringency is generally performed at 0.02 M to 0.15 M NaCl at a temperature range of 50° C. to 70° C. Other factors that can affect stringency are the presence of formamide, tetramethylammonium chloride and/ or other solvents in the hybridization mixture.

B. Nucleic Acid Synthesis De Novo

In one embodiment, the RNA molecules of the present invention may be synthesized de novo, i.e., chemically. Nonlimiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266 032, incorporated herein by reference, or via deoxynucleoside H-phosphonate intermediates as described by Froehler et al. (1986) and U.S. Pat. No. 5,705, 629, each incorporated herein by reference. Various different mechanisms of nucleic acid synthesis have been disclosed in for example, U.S. Pat. Nos. 4,659,774, 4,704,362, 4,816,571, 5,141,813, 5,264,566, 4,959,463, 5,221,619, 5,428,148, 5,554,744, 5,574,146, 5,602,244, and 5,583,013 each of which is incorporated herein by reference. A general discussion of chemical synthesis of nucleic acid methods follows below.

Diester Method.

The diester method was the first to be developed to a usable state, primarily by Khorana and co-workers (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method.

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligodeoxynucleotides (Gillam et al., 1978; Gillam et al., 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

2. SCREENING FOR INHIBITORY RNAS

The present inventor now describes a new approach to identifying putative microRNA using the assumptions and criteria set forth in FIG. 4A. First, one will search for mRNAs having a complete match to the first 8 nucleotides of miR-1. Second, consistent with recent reports of free energy of binding (Doench and Sharp, 2004), an A to G switch at the 8th nucleotide is predicted to give the strongest $\Delta G$, suggesting that a G-U wobble at this position would be allowed or preferred for microRNA binding to its mRNA targets. Third, one assumes that true 3' UTR targets share conservation between chick, mouse, rat and human, and thus cross-species searches are performed. One will then analyze the local mRNA secondary structure (e.g., 70 bp 5' and 3' of the putative miRNA binding site; using mFold is exemplified), selecting for instability within the flanking region, and finally assessing the secondary structure of the target sequence for stabilizing or destabilizing elements. The same approach may be used to identify siRNAs as well.

3. EXPRESSION CONSTRUCTS

A. Vectors

In accordance with the present invention, it may be desirable to express the miRNAs of the present invention. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., BACs, YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

i. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. (2001), incorporated herein by reference). The promoters employed may be constitutive, tissue-specific, inducible, and/or useful under the appropriate conditions to direct high level expression of the introduced DNA segment. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Of particular interest in the present invention are the enhancer sequences identified as SEQ ID NOS:14, 15, 17, and 18.

ii. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

v. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

vi. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

vii. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows' for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

viii. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

ix. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

Adenoviral Vectors.

A particular method for delivery of nucleic acids involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors.

The nucleic acid may be introduced into a cell using adenovirus-assisted transfection. Increased transfection efficiencies have been reported in cell systems using adenovirus coupled systems (Kelleher and Vos, 1994; Cotteri et al., 1992; Curiel, 1994). Adeno-associated virus (AAV) is an attractive vector system as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 19.84; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors.

Retroviruses have promise as delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors.

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Delivery Using Modified Viruses.

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

x. Non-Viral Vector Delivery

Suitable methods for nucleic acid delivery to cells for use with the current invention are believed to include virtually any method by which a nucleic acid (e.g., DNA), as known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome-mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985), and any combination of such methods.

xi. Ex Vivo Transformation

Methods for tranfecting vascular cells and tissues removed from an organism in an ex vivo setting are known to those of skill in the art. For example, cannine endothelial cells have been genetically altered by retrovial gene transfer in vitro and transplanted into a canine (Wilson et al., 1989). In another example, yucatan minipig endothelial cells were tranfected by retrovirus in vitro and transplated into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplated cells or tissues.

Injection.

In certain embodiments, a nucleic acid may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985). The amount of nucleic acid used may vary upon the nature of the antigen as well as the organelle, cell, tissue or organism used Electroporation.

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

Calcium Phosphate.

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran.

In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading.

Additional embodiments of the present invention include the introduction of a nucleic acid by direct sonic loading. LTK$^-$ fibroblasts have been transfected with the thymidine kinase gene by sonication loading (Fechheimer et al., 1987).

Liposome-Mediated Transfection.

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection.

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

xii. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally-occurring cells which do not contain a recombinantly introduced nucleic acid. Of particular interest in the present invention are muscle cells, such as cardiac and skeletal muscles, and muscle cell progenitors.

4. SCREENING ASSAYS

The present invention also contemplates the screening of compounds, e.g., peptides, polypeptides, nucleic acids or small molecules, for various abilities to mimic, or interfere with the function of the miRNAs described herein. In the screening assays of the present invention, the candidate substance may first be screened for basic biochemical activity—e.g., binding to a target RNA sequence, inhibition of miRNA binding thereto, alteration in gene expression—and then further tested for function in at the cellular or whole animal level.

A. Modulators

The present invention provides methods of screening for agents that alter the activity or expression of miRNAs. As used herein, the term "candidate substance" refers to any molecule that may potentially modulate the function of miR-1-1, miR-1-2 or miR-133a2. The candidate substance may be a peptide, or a small molecule inhibitor, or even a nucleic acid molecule.

One may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be a polypeptide, polynucleotide, small molecule inhibitor or any other compounds that may be developed through rational drug design starting from known compounds that affect these miRNAs, such as myoD, myocardin and SRF.

It will, of course, be understood that all the screening methods of the present invention are useful in themselves notwithstanding the fact that effective candidates may not be found. The invention provides methods for screening for such candidates, not solely methods of finding them.

B. In Cyto Assays

Various cells naturally express miR-1-1, miR-1-2 or miR-133a2 and can be utilized for screening of candidate substances. Of particular interest are muscle cells, such as cardiac and skeletal muscle cells, and progenitors therefor. Other cells may be engineered to express miR-1-1, miR-1-2 or miR-133a2, or may contain the control regions for the corresponding genes linked to screenable marker genes, permitting one to assess the effects of a candidate substance on the expression of miR-1-1, miR-1-2 or miR-133a2. Alternatively, one may look at the expression of Hand2 or thymosin β4, both of which have their expression modulated by miR-1-1, miR-1-2 or miR-133a2.

Assays may be employed within the scope of the instant invention for determination of the relative efficiency of gene expression. Gene expression may be determined by measuring the production of miRNA in question. The product may be isolated and/or detected by methods well known in the art. Following detection, one may compare the results seen in a given cell line or individual with a statistically significant reference group of non-transformed control cells.

Northern analysis is a method used to identify RNA sequences that hybridize to a known probe such as all oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

The technique of "polymerase chain reaction," or PCR, as used generally herein, refers to a procedure wherein minute amounts of a specific piece of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally, Mullis et al., (1987); Erlich (1989). As used herein, PCR will be coupled with reverse transcription (RT) to convert RNA into DNA prior to amplification. Methods for coupled RT-PCR are well known in the art and are described in U.S. Pat. No. 5,310,652, incorporated herein by reference.

Significantly, RT-PCR (reverse transcription-polymerase chain reaction) is the most sensitive technique for mRNA quantitation currently available. Compared to the two other commonly used techniques for quantifying mRNA levels, Northern blot analysis and Rnase protection assay, RT-PCR can be used to quantify mRNA levels from much smaller samples. In fact, this technique is sensitive enough to enable quantitation of RNA from a single cell.

Over the last several years, the development of novel chemistries and instrumentation platforms enabling detection of PCR products on a real-time basis has led to widespread adoption of real-time RT-PCR as the method of choice for quantitating changes in gene expression. At the start of any PCR reaction, the amplification proceeds at a constant, exponential rate, due to the excess of reagents. The reaction rate ceases to be exponential and enters a linear phase of amplification, after which the amplification rate drops to near zero (plateaus), and little more product is made. In order to accurately assess nucleic acid quantiteis, it is necessary to collect data at a point in which every sample is in the exponential phase of amplification, since it is only in this phase that amplification is extremely reproducible. Unfortunately, the point at which this transition takes place is highly variable. Real-time PCR automates this otherwise laborious process by quantitating reaction products for each sample in every cycle. The result is an amazingly broad $10^7$-fold dynamic range, with no user intervention or replicates required.

Currently, four different technologies—TaqMan® (Applied Biosystems, Foster City, Calif., USA), Molecular Beacons, Scorpions® and SYBR® Green (Molecular Probes)— are available for real-time PCR. Each approach allows detection of PCR products through the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moeity to the same or different oligonucleotide substrates. SYBR Green is a fluorogenic dye that exhibits little fluorescence when in solution, but emits a strong fluorescent signal upon binding to double-stranded DNA. The TaqMan probes, Molecular Beacons and Scorpions also allow multiple DNA species to be measured in the same sample (multiplex PCR), since fluorescent dyes with different emission spectra may be attached to the different probes.

Another option for quantitating RNA species is relative quantitative RT-PCR, which uses primers for an internal control that are multiplexed in the same RT-PCR reaction with the gene specific primers. Internal control and gene-specific primers must be compatible, i.e., they must not produce additional bands or hybridize to each other. Common internal controls include β-actin and GAPDH mRNAs and 18S rRNA. Unlike Northerns and nuclease protection assays, the selection and implementation of controls in relative quantitative RT-PCR requires substantial optimization.

For relative quantitative RT-PCR data to be useful, the PCR reaction must be terminated when the products from both the internal control and the gene of interest are detectable and are being amplified within exponential phase. Because control RNA targets are often high abundance genes, their amplification surpasses exponential phase after only a few PCR cycles. It is therefore difficult to identify compatible exponential phase conditions where the PCR product from a rare message is detectable. However, for more common species, this approach works well.

5. METHODS OF INDUCING OR INHIBITING MUSCLE CELL DIFFERENTIATION

In accordance with the present invention, there are provided methods for both inducing and inhibiting muscle cell differentiation. With regard to the former, agonists of miR-1-1, miR-1-2, and/or miR-133a2 include these molecules and expression constructs coding therefore (described above). Also envisioned are small molecules, proteins and nucleic acids identified in accordance with the screening methods set forth herein.

In inhibiting muscle cell differentiation, one may envision that populations of muscle cell progenitors, including stem cells, may be treated with an antagonist of miR-1-1, miR-1-2, and/or miR-133a2, thereby permitting their maintenance, modification (e.g., transformation) or expansion in culture. In addition, it may be possible to reprogram adult muscle (skeletal, cardiac) cells in vivo to address the treatment of pathologic conditions such as myocardial infarcts. Antagonists can be of any kind, but particularly contemplated antagonists included antisense (modified and unmodified) constructs.

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Bioinformatics.

Multiple sequence alignment was constructed by ClustalX 1.83 with appropriate settings, and promoter analysis was performed with rVISTA. PatScan program was used for targets search, and energy and RNA folding were determined by mFold. Average ΔG in each species was determined by randomly selecting 60 3' UTR fragments of 70 bp in length. The inventor determined the RNA secondary structure of each miRNA binding site plus 30 bp flanking sequence on each side. The inventor set the following values as a cut-off to define DSE and SE based on our observation. Average stem length was calculated for each species from at least 60 randomly selected sequences and cutoff for a SE stem was defined as: ≥8 bp (worm); ≥9 bp (flies); ≥10 bp (mice). Loops or unstructured single strands were defined as DSE with the following length cutoffs: hairpin loop, ≥11 bp; interior loop, ≥9 bp; bulge loop, ≥7 bp; multiple-branching loop, ≥11 bp; joint sequence and free end, ≥11 bp.

Plasmid Construction.

Target sequences and their mutant forms were synthesized as DNA oligos. After annealing and concatamerization, 4 copies of the target sequence were excised using a sized gel, blunt ended and sub-cloned into pGL-TK vector. To express miR-1s in COS1, the genomic sequence containing pre-miR-1s plus about 50 bp flanking each side were inserted into pcDNA3. Site-directed PCR-mediated mutagenesis was performed using pfu DNA polymerase. RT-PCR was performed using Superscript III first-strand synthesis system (Invitrogen);

Cell Transfection, EMSA, Luciferase Assay, Northern Blot and Western Blot.

Plasmid transfection was performed in 12-well plates using FuGENE 6 (Roche). RSVlacZ expression construct was cotransfected to normalize for transfection efficiency. Luciferase and β-gal activities in the cell extract were assayed 36 h after transfection using the Luciferase Assay System (Promega). All experiments were repeated at least three times, and representative results are shown. Northern blot was performed as described[25]. Western blot was performed on heart lysates by standard methods using specific antibodies. EMSA was performed as previously described (Yamagishi et al., 2003).

Generation of Transgenic Mice.

Transgenic mice were generated and β-gal staining and histological analyses were performed as previously described (Yamagishi et al., 2003). For promoter analysis, different fragments were sub-cloned into pHsp68lacZ reporter vector. For over-expression, miR-1 was sub-cloned into α-MHC-clone26 or β-MHCclone32 vectors.

Example 2

Results

MiR-1-1 and miR-1-2 are Expressed in Developing Cardiac and Skeletal Muscle.

To determine whether miRNAs play a role in cardiac development or homeostasis, the inventor searched for miRNAs that were expressed in the cardiovascular system and were conserved across species ranging from flies to humans. Among these, miRNA1 (miR-1) appeared cardiacenriched based on our in silico data and previous reports (Lee and Ambros, 2001; Lagos-Quintana et al., 2001). The miR-1 subfamily consists of two closely related miRNAs, encoded by distinct genes, which share near complete identity and are designated miR-1-1 and miR-1-2. The inventor found that the putative miR-1-1 and miR-1-2 sequences, based on genomic sequence from different species, were highly conserved (FIG. 1A). Northern blot revealed that miR-1s were 21 base pairs in length and were expressed specifically in the heart and skeletal muscle of adult mice (FIG. 1B and FIG. 5).

Due to the similarity in miR-1-1 and miR-1-2 sequence and the small size of microRNAs, the relative expression of each miR-1 could not be determined, nor could mRNA in situ hybridization be used to delineate the embryonic expression domains of miR-1s. The inventor therefore searched for enhancers that might regulate transcription of miR-1-1 or miR-1-2 in vivo in order to define the tissue-specific expression and regulation of miR-1s during embryogenesis. Comparison of genomic sequence across species using rVISTA revealed that a 4.6 kb or 10.7 kb genomic region around miR-1-1 or miR-1-2, respectively, was conserved between human and mouse (FIG. 1C). The inventor found that the 4.6 kb miR-1-1 fragment was sufficient to direct lacZ expression in the hearts of transgenic mice after embryonic day (E) 8.5 (FIG. 1D) with expression strongest in the inner curvature of the looping heart tube at this stage. The inner curvature is less proliferative than the outer curvature, which is expanding and ballooning ventrally to form the cardiac chambers. In addition, expression of miR-1-1 was more robust in the developing atria compared to ventricles at early stages. Cardiac expression became more robust and uniform as cardiomyocyte differentiation proceeded and expression in the myotome of somites also became apparent as skeletal muscle differentiation began (FIG. 1D). Similarly, the 10.7 kb miR-1-2 fragment contained all the regulatory elements necessary to drive lacZ expression in the embryonic ventricles and somites at similar stages as that described for miR-1-1 (FIG. 1E). In contrast to miR-1-1, miR-1-2-lacZ was only expressed in the ventricles, but not atria, suggesting chamber-specificity of miR-1 activity (FIG. 1E). Both miR-1 enhancers directed expression in the outflow tract of the heart, which arises from a secondary heart field[27], distinct from the primary heart field that contributes to atrial and left ventricular myocardium (FIGS. 1D,E).

miR-1-1 and miR-1-2 are Direct Targets of SRF in the Heart.

To help elucidate the cellular pathways in which miR-1-1 and miR-1-2 function the inventor searched for the precise cis elements and transcription factors that were responsible for the lacZ expression described above. Deletion analyses suggested that 2.6 kb or 0.35 kb regions were sufficient for full miR-1-1 or miR-1-2 expression, respectively (FIGS. 2A,B). Within these regions the inventor noted several cis elements conserved between human and mouse that represented potential binding sites for the essential cardiac transcription factors, Mef2, SRF, Nkx2.5 and Gata4. SRF sites in the miR-1-1 and miR-1-2 enhancers were nearly identical and highly conserved in human, mouse and chick, as were Mef2 and MyoD sites in miR-1-1 or in miR-1-2, respectively (FIGS. 2C,D). In transgenic mice, the Mef2 site in the miR-1-1 enhancer was dispensable for cardiac expression but was necessary for full somite regulation. Mutation of the miR-1-1 SRF site abolished expression in the heart, while disruption of both sites abolished all activity of the enhancer (FIG. 2A). Consistent with a cardiac requirement for SRF, mutation of the SRF site in the miR-1-2 regulatory region disrupted cardiac expression of miR-1-2 while mutation of the MyoD site only partially affected somitic expression (FIG. 2B).

SRF, Mef2 or MyoD could each bind their respective site in gel electromobility shift assays and specificity of interaction was determined by use of competition with wild-type or mutant oligonucleotides and/or antibody-mediated supershifts (FIGS. 2C,D). SRF is a weak activator of numerous muscle-specific genes and is thought to mediate muscle differentiation by regulating decisions of cellular proliferation and differentiation (Norman et al., 1988; Miralles et al., 2003; Miano et al., 2004; Wang et al., 2004). During cardiac and smooth muscle development, the SAP domain protein myocardin serves as a potent co-activator for SRF and promotes muscle differentiation (Wang et al., 2001; Wang and Olson, 2004). Consistent with this, the inventor found that SRF was a weak activator of luciferase under control of the miR-1-1 or miR-1-2 enhancers, but synergized with myocardin to activate the miR-1 enhancers (FIG. 2E, and data not shown). Mutation of the SRF binding site disrupted activity, suggesting that the transcriptional activity of SRF and myocardin on the miR-1 enhancers was through the highly conserved SRF-binding cis element (FIG. 2E). To determine if SRF was required for miR-1 expression in vivo, the inventor examined RNA from hearts lacking SRF through tissue-specific disruption of the SRF gene$_{28}$. The inventor found that miR-1 transcripts were decreased in SRF heterozygous hearts and were undetectable by RT-PCR in SRF homozygous mutant hearts (FIG. 2F). These data provide the first detailed embryonic description of miRNA expression and transcriptional regulation in mammals and suggest that miR-1-1 and miR-1-2 function in SRF-myocardin dependent pathways in cardiac progenitors and are MyoD/Mef2 responsive in skeletal precursors.

MIR-1 Regulates Ventricular Cardiomyocyte Proliferation and Expansion.

To determine if the dosage of miR-1 target genes might be important in the SRF-dependent balance of proliferation and differentiation, the inventor over-expressed miR-1 specifically in the developing heart under control of the β-MHC promoter, which directs high levels of expression by E9.0. Excessive miR-1 expression resulted in developmental arrest at E13.5 secondary to thin-walled ventricles and heart failure (FIGS. 3A-G). The more proliferative compact zone in miR-1 transgenic embryos was only 3-5 cell layers in thickness in contrast to nontransgenic littermates, which contained layers of 8-10 cells. Analysis of mitogenic activity using the phophohistone H3 antibody revealed a significant decrease in the number of cycling myocardial cells in miR-1 transgenic mice at E13.5 (FIGS. 3A-G), while no increase in apoptotic cells was observed (data not shown). Thus, a decrease in the protein levels of miR-1 targets during cardiogenesis resulted in a proliferation defect and failure of ventricular cardiomyocyte expansion. Given that miR-1 is regulated by SRF and myocardin, the phenotype is consistent with premature differentiation and early cell cycle withdrawal of myocytes (Shin et al., 2002).

MiR-1 Targets Hand2 mRNA for Post-Transcriptional Regulation.

Genetic studies in flies and worms have revealed several validated miRNA targets (Table 2). Recently several groups have developed computational methods to predict miRNAs targets based on the fundamental assumption that the 5' nucleotides of miRNA are most critical for target recognition (Lai, 2002; Stark et al., 2003; Lewis et al., 2003; Kiriakidou et al., 2004; John et al., 2004; Lewis et al., 2005). While sequence-based predictions have been successful in plants, the algorithms employed to date for non-plant miRNAs often result in few overlapping targets and large-scale predictions have not yet been validated by demonstration of activity on endogenous targets in vivo (Lewis et al., 2003; Kiriakidou et al., 2004; John et al., 2004; Lewis et al., 2005; Rhoades et al., 2002). The two vertebrate exceptions are the demonstration of Hoxb8 as a target of miR-196, which was facilitated by a nearly perfect sequence match in the 3' UTR of Hoxb8, and the miR-375 target Myotrophin involved in insulin secretion (Yekta et al., 2004; Poy et al., 2004).

Target accessibility has long been established as an important factor for effectiveness of antisense oligonucleotides and siRNA-mediated silencing (Lee et al., 2002) and the inventor therefore postulated that it may also be involved in miRNA target repression. To test this idea, the inventor used the program mFold to analyze all miRNA repression targets identified to date, and found that virtually all miRNA binding sites in 3' UTRs were located in "unstable" regions based on free energy predictions ($\Delta G$) and RNA structure. Table 2 lists the free energy of the flanking 70 nucleotides 3' and 5' of the one or more predicted miRNA target sequences in the 3' UTR of validated target genes. The $\Delta G$ of the 5' or 3' flanking region around at least one of the predicted miRNA binding sites within the 3' UTR of each target gene was significantly lower than the average $\Delta G$ within that species (Table 2), suggesting a locally linear RNA structure around the target mRNA binding site that could not form tight stems.

TABLE 2

| miRNA | Target | Site | 5'70 bp ($\Delta G$) | 3'70 bp ($\Delta G$) | DSE | SE |
|---|---|---|---|---|---|---|
| Lin-4 | Lin-14 | I | 7.7 | 3.4 | — | — |
| | | II | 7.8 | 1.5 | IL | — |
| | | III | 2.6 | 4.2 | HL | — |
| | | IV | 5.0 | 8.3 | — | — |
| | | V | 4.2 | 10.6 | — | — |
| | | VI | 9.3 | 8.7 | — | Stem |
| | | VII | 3.2 | 3.0 | Joint | — |
| | Lin-28 | I | 0.6 | 10.1 | Free end | — |
| | Lin-57 | I | 10.2 | 8.2 | Joint | — |
| | | II | 3.1 | 4.8 | HL | — |
| Let-7 | Lin-41 | I | 0.6 | 7.6 | Joint | — |
| | | II | 9.4 | 7.2 | MBL | — |
| | | III | 6.2 | 7.2 | IL | — |
| | | IV | 8.1 | 6.3 | IL | — |
| | | V | 5.1 | 9.4 | HL, Free end | Stem |
| | | VI | 12.4 | 5.9 | HL | Stem |
| | Lin-41(mt) | I | 0.6 | 4.4 | — | — |
| | | II | 6.6 | 7.2 | — | — |
| | daf-12 | I | 1.6 | 10.2 | IL | — |
| | | II | 8.9 | 1.1 | HL, Free end | — |
| | Lin-57 | I | 1.5 | 3.9 | MBL | — |
| | | II | 8.1 | 8.8 | — | — |
| | | ILL | 5.9 | 4.7 | Free end | — |
| | | IV | 2.3 | 0.7 | MBL | — |

TABLE 2-continued

| miRNA | Target | Site | 5'70 bp (ΔG) | 3'70 bp (ΔG) | DSE | SE |
|---|---|---|---|---|---|---|
| | | V | 0.3 | 0.1 | HL | — |
| | | VI | 0.2 | 0.3 | HL, Free end | — |
| | | VII | 0.7 | 3.8 | Free end | — |
| | | VIII | 0.3 | 9.0 | Free end | — |
| Lsy-6 | Cog-1 | I | 1.1 | 1.7 | Free end | — |
| miR-273 | Die-1 | I | 3.8 | 0.3 | Free end | — |
| | | II | 4.1 | 5.5 | MBL | — |
| Bantam | Hid | I | 3.4 | 8.6 | HL | — |
| | | II | 9.5 | 9.2 | HL | — |
| | | III | 1.3 | 4.1 | Free end | — |
| | | IV | 24.7 | 19.2 | — | — |
| | | V | 8.6 | 7.2 | Joint | — |
| miR-196 | Hoxb8 | I | 12.8 | 1.6 | HL | — |
| miR-375 | Myotrophin | I | 9.2 | 7.2 | — | — |

In silico analysis of previously described miRNA targets. Free-energy (ΔG) analysis of sequence flanking each putative target binding site and description of destabilizing elements (DSE) or stabilizing elements (SE) within binding sites. IL, interior loop; HL, hairpin loop; MBL, multi-branching loop. Top portion (*C. elegans*; Avg ΔG-7.2); middle portion (*D. melanogaster*; Avg ΔG - 8.5); bottom portion (*M. musculus*; Avg ΔC - 13.4).

However, genes that had multiple putative binding sites typically had several sites that were in regions of high ΔGs. To resolve this, the inventor compared the conservation of high ΔG versus low ΔG sites in closely related worm (Meister and Tuschl, 2004) or fly (Abrahante et al., 2003) species in an attempt to better predict validity of true target sites. The inventor found that virtually all high ΔG sites had variances in the sequence matching the critical 5' region of the miRNA, several of which would clearly disrupt interaction as seen in lin-14 (Site VI for lin-4) and lin-57 (Site II for let-7), making it unlikely that such sites are true targets (FIG. 6). In contrast every low ΔG site was completely conserved in all species, consistent with the idea that they may represent actual target sites (FIG. 6). Consistent with the cross-species data, previous deletion of high ΔG sites in lin-41 (sites III-VI for let-7) suggested that they were dispensable. Together, the conservation of target sites within *Caenorhabditis* and *Drosphila* species and mutational analyses support the predictive value of the free energy of sequences flanking true miRNA target sites.

In addition to the flanking sequence, the inventor analyzed the stability of the predicted miRNA target sequence itself to determine if RNA structural features could be found that might affect accessibility and enhance specificity of target prediction. In a simplified view, secondary structure of RNA can be composed of stems, loops or unstructured single strands. Long stems are stabilizing elements (SE) and might render the RNA less accessible to miRNAs, while all long loops, including hairpin, interior, bulge and multi-branching loops could be considered as destabilizing elements (DSE). Unstructured single strands, including joint sequences and free ends are also destabilizing and together with other DSE may represent structures that permit miRNA and target sequence interaction. The inventor found that no validated target sites contained SE, while most target sequences did have DSE; several putative sites that had high ΔG's or had been experimentally dispensable also had SE. Consistent with this idea, reported mutations in the spacer region between sites I and II in Lin-41 (10), which abolished repression, altered the secondary structure resulting in the loss of DSE, possibly explaining the effect of these mutations (Table 2 and FIG. 6). There were almost no exceptions to the association of SE or DSE with targets, suggesting that the presence or absence of SE and DSE might have predictive value in an in silico screen for putative miRNA targets.

Based on the observations above, the inventor searched for putative miR-1 targets with several assumptions and criteria (FIG. 4A). First, the inventor searched for mRNAs that had a complete match to the first 8 nucleotides of miR-1. Second, consistent with recent reports of free energy of binding (Doench and Sharp, 2004), an A to G switch at the 8$^{th}$ nucleotide gave the strongest ΔG, suggesting that a G-U wobble at this position would be allowed (or maybe preferred) for miR-1 binding to its mRNA targets. Third, the inventor assumed that true 3' UTR targets would share conservation between chick, mouse, rat and human. Finally, the inventor analyzed the local mRNA secondary structure 70 bp 5' and 3' of the putative miRNA binding site using mFold, selecting for instability within the predicted region, and assessed the secondary structure of the target sequence for SE or DSE.

Using these criteria, the inventor scanned all known mRNA 3'UTRs for potential miR-1 targets. Approximately 13 mRNAs matched miR-1 and the putative target sequences were conserved across species (FIG. 4B). However, most 5' and 3' flanking regions had ΔG's that were close to the species average and did not suggest local. instability (FIG. 4B). To validate putative targets and to test whether the ΔG/(D)SE would add further specificity to the in silico screen, the inventor elected for further study a few predicted targets that were co-expressed with miR-1s in the heart or skeletal muscle. One of these, the transcription factor Hand2, had a particularly unstable 5' region with a ΔG of 4.6 and animals lacking Hand2 are well-characterized to have a failure of ventricular cardiomyocyte expansion ((Yelon et al., 2000; Srivastava et al., 1997; Yamagishi et al., 2001; McFadden et al., 2005). The inventor also chose to test thymosin β4, a G-actin sequestering protein expressed during cardiogenesis$_{43}$, which did not have a predicted ΔG lower than the average but showed high sequence complementarity with miR-1 (FIG. 7).

Previous studies suggest that miRNA binding sites are transferable and sufficient to confer miRNA-dependent translational repression (Yekta et al., 2004; Doench and Sharp, 2004), so the inventor placed multimers of about 80 bp containing the predicted miR-1 target site from Hand2 or thymosin β4 3'UTRs into the 3' UTR of a luciferase reporter plasmid (FIG. 4C). The inventor introduced the luciferase expression vector under a constitutively active promoter with or without miR-1 into Cos1 cells and measured the level of luciferase enzyme activity to determine the effects of miR-1 on luciferase translation in the presence of its target sequence. Transfection of the Hand2 chimeric luciferase reporters into Cos1 cells, which do not express any endogenous miR-1 (FIG. 1B), consistently resulted in a decrease in luciferase activity upon introduction of wild-type miR-1 (FIG. 4D). This was uniformly true for the putative miR-1 target region from the 3' UTR of mouse, chick, frog or fish, suggesting evolutionary conservation of Hand2 as a miR-1 target. In this assay, the 3' UTR of thymosin β4 also resulted in decreased luciferase activity. The mutant target sequence for Hand2 or thymosin β4 fused to the 3' UTR of luciferase was not responsive to wild-type miR-1, suggesting specificity of the repression effect. Furthermore, mutant miR-1s (FIG. 4C) had no effect on the wild-type target sequences, but could partially repress translation of luciferase transcripts containing the corresponding mutant 3' UTRs (FIG. 4D).

While the ability of miRNAs to repress translation of chimeric luciferase reporters is a useful screening tool, it remains a surrogate for testing the effect of miRNAs on their putative targets and can result in misleading assessment of targets. To more directly test the validity of our putative targets, the inventor asked if miR-1 could repress endogenous protein expression in vivo in transgenic mice (FIG. 8). Western blot of transgenic hearts overexpressing miR-1 demonstrated a significant decrease in Hand2 protein compared to non-transgenic littermates, confirming Hand2 as a miR-1 target in vivo (FIG. 4E). No change in mRNA of Hand2 was noted (FIG. 4E). Together, the in silico, in vitro and in vivo data provided compelling evidence that Hand2 is a true target of miR-1 during cardiogenesis. In contrast, the inventor could not detect any discernable difference of thymosin β4 protein in the miR-1 overexpressing transgenic hearts compared to wild-type, though the putative miR-1 binding site in thymosin β4 showed perfect sequence complementarity and conservation across at least 9 species (FIG. 7). This was consistent with the high ΔG regions around the target sequence. Similarly, despite the low ΔG for another putative target, IGF1, the inventor did not detect any change in IGF1 protein level in transgenic hearts, consistent with the presence of a SE in the target sequence (FIG. 4B). These findings suggest that local RNA secondary structure may indeed be critical in miRNA-mediated repression and highlights the complexity of target prediction and risk of reliance on surrogate reporters for target specificity.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

7. REFERENCES

The following references, to the extent that they provide exemplary procedural or other details supplementary to those set forth herein, are specifically incorporated herein by reference.

U.S. Pat. No. 4,659,774
U.S. Pat. No. 4,683,195
U.S. Pat. No. 4,683,202
U.S. Pat. No. 4,704,362
U.S. Pat. No. 4,797,368
U.S. Pat. No. 4,816,571
U.S. Pat. No. 4,959,463
U.S. Pat. No. 5,139,941
U.S. Pat. No. 5,141,813
U.S. Pat. No. 5,221,619
U.S. Pat. No. 5,264,566
U.S. Pat. No. 5,302,523
U.S. Pat. No. 5,310,652
U.S. Pat. No. 5,322,783
U.S. Pat. No. 5,384,253
U.S. Pat. No. 5,384,253
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,583,013
U.S. Pat. No. 5,589,466
U.S. Pat. No. 5,602,244
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
Abrahante et al., et al., *Dev. Cell*, 4:625-37, 2003.
Ambros, *Nature*, 431:350-5, 2004.
Ausubel et al., In: *Current Protocols in Molecular Biology*, John, Wiley & Sons, Inc, New York, 1996.
Baichwal and Sugden, In: *Gene Transfer*, Kucherlapati (Ed.), NY, Plenum Press, 117-148, 1986.
Beaucage, and Lyer, *Tetrahedron*, 48:2223-2311, 1992.
Blomer et al., *J. Virol.*, 71 (9):6641-6649, 1997.
Bock-Marquette et al., *Nature*, 432:466-72, 2004.
Brennecke et al., *Cell*, 113:25-36, 2003.
Carbonelli et al., *FEMS Microbiol. Lett.*, 177 (1):75-82, 1999.
Chang et al., *Nature*, 430:785-9, 2004.
Chen and Okayama, *Mol. Cell. Biol.*, 7 (8):2745-2752, 1987.
Chen et al., *Cell*, 110:713-23, 2002.
Chien and Olson, *Cell*, 110:153-62, 2002.
Christou et al., *Proc. Natl. Acad. Sci. USA*, 84 (12):3962-3966, 1987.
Cocea, *Biotechniques*, 23 (5):814-816, 1997.
Cotten et al., *Proc. Natl. Acad. Sci. USA*, 89 (13):6094-6098, 1992.
Coupar et al., *Gene*, 68:1-10, 1988.
Curiel, *Nat. Immun.*, 13 (2-3):141-164, 1994.
D'Halluin et al., *Plant Cell*, 4 (12):1495-1505, 1992.
Doench and Sharp, *Genes Dev.*, 18:504-11, 2004.
Doench et al., *Genes Dev.*, 17:438-42, 2003.
Erlich, In: *PCR Technology*, Stockton Press, N.Y., 1989.
European Appln. 0273085
European Appln. 266 032
Fechheimer, et al., *Proc Natl. Acad. Sci. USA*, 84:8463-8467, 1987.
Firulli et al., *Nat. Genet.*, 18:266-70, 1998.
Fraley et al., *Proc. Natl. Acad. Sci. USA*, 76:3348-3352, 1979.
Friedmann, *Science*, 244:1275-1281, 1989.
Froehler et al., *Nucleic Acids Res.*, 14 (13):5399-5407, 1986.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gillam et al., *J. Biol. Chem.*, 253:2532-2539, 1978.
Gillam et al., *Nucleic Acids Res.*, 6:2973, 1979.
Goodbourn and Maniatis, *Proc. Natl. Acad. Sci. USA*, 85:1447, 1988.
Gopal, *Mol. Cell. Biol.*, 5:1188-1190, 1985.
Graham and Van Der Eb, *Virology*, 52:456-467, 1973.
Grosshans et al., *Dev. Cell.*, 8:321-330, 2005.
Grunhaus and Horwitz, *Seminar in Virology*, 3:237-252, 1992.
Haley and Zamore, *Nat. Struct. Mol. Biol.*, 11:599-606, 2004.
Harland and Weintraub, *J. Cell Biol.*, 101 (3):1094-1099, 1985.
He and Hannon, *Nat. Rev. Genet.* 5:522-31, 2004.

Horwich et al., *J. Virol.*, 64:642-650, 1990.
Hou and Lin, *Plant Physiology*, 111:166, 1996.
Inouye and Inouye, *Nucleic Acids Res.*, 13: 3101-3109, 1985.
Itakura et al., *J. Biol. Chem.*, 250:4592 1975.
John et al., *PLoS Biol.*, 2:e363, 2004.
Johnston and Hobert, *Nature*, 426:845-9, 2003.
Kaeppler et al., *Plant Cell Reports*, 9:415-418, 1990.
Kaneda et al., *Science*, 243:375-378, 1989.
Kato et al., *J. Biol. Chem.*, 266:3361-3364, 1991.
Kelleher and Vos, *Biotechniques*, 17 (6):1110-7, 1994.
Kelly and Buckingham, *Trends Genet.*, 18:210-6, 2002.
Khorana, *Science*, 203 (4381):614-625, 1979.
Kiriakidou et al., *Genes Dev.*, 18:1165-78, 2004.
Lagos-Quintana et al., *Science*, 294:853-8, 2001.
Lai, *Nat. Genet.*, 30:363-4, 2002.
Laughlin et al., *J. Virol.*, 60 (2):515-524, 1986.
Lebkowski et al., *Mol. Cell. Biol.*, 8 (10):3988-3996, 1988.
Lee and Ambros, *Science*, 294:862-4, 2001.
Lee et al., *Cell*, 75:843-54, 1993.
Lee et al., *Korean J. Genet.*, 11 (2):65-72, 1989.
Lee et al., *Nat. Biotechnol.*, 20:500-5, 2002.
Levenson et al., *Hum. Gene Ther.*, 9 (8):1233-1236, 1998.
Lewis et al., *Cell*, 115:787-98, 2003.
Lewis et al., *Cell*, 120:5-20, 2005.
Macejak and Sarnow, *Nature*, 353:90-94, 1991.
Mann et al., *Cell*, 33:153-159, 1983.
McFadden et al., *Development*, 132:189-201, 2005.
McLaughlin et al., *J. Virol.*, 62 (6):1963-1973, 1988.
Meister and Tuschl, *Nature*, 431:343-9, 2004.
Miano et al., *Proc. Natl. Acad. Sci. USA*, 101:17132-7, 2004.
Miller et al., *Am. J. Clin. Oncol.*, 15(3):216-221, 1992.
Miralles et al., *Cell*, 113:329-42, 2003.
Moss et al., *Cell*, 88:637-46, 1997.
Mullis et al., In: *Syrup. Quant. Biol.*, Cold Spring Harbor, 51:263, 1987.
Muzyczka, *Curr. Topics Microbiol. Immunol.*, 158:97-129, 1992.
Nabel et al., *Science*, 244 (4910):1342-1344, 1989.
Nabel et al., *Science;* 244 (4910):1342-1344, 1989.
Naldini et al., *Science*, 272 (5259):263-267, 1996.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Norman et al., *Cell*, 55:989-1003, 1988.
Paskind et al., *Virology*, 67:242-248, 1975.
PCT Appln. WO 84/03564
PCT Appln. WO 94/09699
PCT Appln. WO 95/06128
Pelletier and Sonenberg, *Nature*, 334 (6180):320-325, 1988.
Perales et al., *Proc. Natl. Acad. Sci. USA*, 91:4086-4090, 1994.
Potrykus et al., *Mol. Gen. Genet.*, 199 (2):169-177, 1985.
Potter et al., *Proc. Natl. Acad. Sci. USA*, 81:7161-7165, 1984.
Poy et al., *Nature*, 432:226-30, 2004.
Rhoades et al., *Cell*, 110:513-20, 2002.
Rhodes et al., *Methods Mol. Biol.*, 55:121-131, 1995.
Ridgeway, In: *Vectors: A Survey of Molecular Cloning Vectors and Their Uses*, Rodriguez et al. (Eds.), Stoneham: Butterworth, 467-492, 1988.
Rippe et al., *Mol. Cell. Biol.*, 10:689-695, 1990.
Roux et al., *Proc. Natl. Acad. Sci. USA*, 86:9079-9083, 1989.
Sambrook et al., In: *Molecular cloning*, Cold Spring Harbor Laboratory Press, Cold Spring Harbor, N.Y., 2001.
Shin et al., *Cell*, 110:725-35, 2002.
Srivastava and Olson, *Nature*, 407:221-6, 2000.
Srivastava et al., *Nat. Genet.*, 16:154-60, 1997.
Srivastava et al., *Science*, 270:1995-9, 1995.
Stark et al., *PLoS Biol.*, 1:E60, 2003.
Temin, In: *Gene Transfer*, Kucherlapati (Ed.), NY, Plenum Press, 149-188, 1986.
Tratschin et al., *Mol. Cell. Biol.*, 4:2072-2081, 1984.
Tur-Kaspa et al., *Mol. Cell. Biol.*, 6:716-718, 1986.
Vella et al., *Genes Dev.*, 18:132-7, 2004.
Wagner et al., *Proc. Natl. Acad. Sci. USA* 87 (9):3410-3414, 1990.
Wang and Olson, *Curr. Opin. Genet. Dev.*, 14:558-66, 2004.
Wang et al., *Cell*, 105:851-62, 2001.
Wang et al., *Nature*, 428:185-9, 2004.
Wightman et al., *Cell*, 75:855-62, 1993.
Wilson et al., *Science*, 244:1344-1346, 1989.
Wilson et al., *Science*, 244:1344-1346, 1989.
Wong et al., *Gene*, 10:87-94, 1980.
Wong et al., *Gene*, 10:87-94, 1980.
Wu and Wu, *Adv. Drug Delivery Rev.*, 12:159-167, 1993.
Wu and Wu, Biochemistry, 27: 887-892, 1988.
Wu and Wu, *J. Biol. Chem.*, 262:4429-4432, 1987.
Yamagishi et al., *Dev. Biol.*, 239:190-203, 2001.
Yamagishi et al., *Genes Dev.*, 7:269-81, 2003.
Yekta et al., *Science*, 304:594-6, 2004.
Yelon et al., *Development*, 127:2573-82, 2000.
Zhou et al., *Exp. Hematol*, 21:928-933, 1993.
Zufferey et al., *Nat. Biotechnol.*, 15 (9):871-875, 1997.

What is claimed is:

1. A method of stimulating the proliferation and inhibiting the differentiation or death of a muscle cell in vivo comprising contacting said cell with a nucleic acid antagonist of miR-1-1 or miR-1-2 function or expression.

2. The method of claim 1, wherein said muscle cell is a muscle progenitor cell.

3. The method of claim 1, wherein said antagonist is an RNA.

4. The method of claim 1, wherein said cell is a human cell.

5. The method of claim 1, wherein said cell is a cardiac muscle cell.

6. The method of claim 1, wherein said cell is a skeletal muscle cell.

7. The method of claim 1, wherein said cell is a stem cell.

8. The method of claim 1, wherein said nucleic acid antagonist is an antisense oligonucleotide.

9. A method of inhibiting differentiation of a muscle cell progenitor in vivo comprising inhibiting the function or expression of one or more of miR-1-1 or miR-1-2 with a nucleic acid antagonist.

10. The method of claim 9, comprising inhibiting the function of miR-1-1.

11. The method of claim 9, comprising inhibiting the function of miR-1-2.

12. The method of claim 9, wherein said cell is a human cell.

13. The method of claim 9, wherein said cell is a cardiac muscle cell.

14. The method of claim 9, wherein said cell is a skeletal muscle cell.

15. The method of claim 9, wherein said cell is a stem cell.

16. The method of claim 9, wherein said antagonist is an RNA.

17. The method of claim 9, wherein said nucleic acid antagonist is an antisense oligonucleotide.

* * * * *

SEQUENCE LISTING

```
<160> NUMBER OF SEQ ID NOS: 122

<210> SEQ ID NO 1
<211> LENGTH: 9434
<212> TYPE: DNA
<213> ORGANISM: Artificial Sequence
<220> FEATURE:
<223> OTHER INFORMATION: Synthetic Primer

<400> SEQUENCE: 1
gcttgggaca catacttctt tatatgccca tatgaacctg ctaagctatg gaatgtaaag      60
aagtatgtat ttcaggctag gaactctctc gccagactga ggggtggccc atgccctgtg     120
ggtggctgct cgggaaaggc aatggaccga tggaccggca gggcctcggg aggccgactg     180
taagggtacc ggctgtgtcc ctgtccctgt tggcattgtt ctgccacttt gcctgtgtca     240
```

-continued

```
gcaggtggaa gtgctcgtca gacattaaat attcagtgtg ctgactgcgg cagagggagg      300
aggccctctg gcaggcctgg ggtcccgagc ggggccagca gggttgggggg tctggaagct     360 tggcttggga atggagttgt actgatcctt gctgtgctct gaaggaggcc tctccagcag      420
aaagggtgtg gggaccgggc agggactgct cagaccactg ggagaggcag caagttctaa      480
aaggtggtgc ttggtggtgg tggtggtggt ggtggtggtg gtggtggtgg tggggcatga      540
agggagggga gagactttgg tagtcacgtg gtaaaggctt tgagggatg agtcctgc        600 tggcctctgg ctcacagggc tggtgggga ggggaggtgg agagccctgc gcagacactg      660
ctgcccactg tgtgctgatt gtatctgctc actgacaatc tcagtgtcag ctctactcat     720
ggctatcctg gccacccatg gtgattcaga taaagggagc ccagggtctg aagctgtccc     780
agtctggatg gaggagttgg ctctggggac ctgggtacag cagctcatcc agggaccccg     840 ggggggggt ggggggaata ggttatttcg ttcggccgac cctgggccca ttccttccct      900
ggctgccccc atcagagcct cagcatcatt ccttcacact ctctcaccaa attcaacctg     960
aagccacctt cttcctggga aggctagcca agtttctgct gagcagtcca ctagcgacct    1020
aggacccctg ttctgcctgc tttgctgaca gctggtctgg ccgggagaag gggccggttg    1080
acaacctttg ggtcccagga aaggagggca gggtcttcca agcccttccc acagagcttg    1140
tcctgcccag gtagatgcag ggtaaagggc tctgggtcca gcagaaagct gtctatctgt    1200
gactaacatc tgcctggctt cagttctggg tcttagagta gcggctgcct gtgatctagc    1260
tgcagtcagc cccctccccc cccaaagcat ctcctccaca ggcctggggg ctctttgtca    1320
catgcatgtg agagtgtaag tgtgggtata gctgtcagtt gtccccgtcg gctgtgtgtg    1380
gcaggtaccc ccttgtgttc ggcaccatga ccttttggtag gaacaggatt gggagcaggg    1440
caggacccct ctgtcagctt taaatgttgg ggcttgagca gtcagatgat ccaagcagct    1500
aggttgagga acctcagacc aaatgccatg gaggaatctg agcccacagg tggcttccat    1560
cctgagtttt cttgaggtga ctccatagtc aagggtttgt cctgaatgtt tcagtcttcc    1620
ttctggaagt cgaattctct cctgatctca gtctccaggc acagagggtg cgacaggcac    1680
cgagaaagca gccttgccct tggtactacc tccctcttgg tcactggtcc cagagctgtc    1740
agtgctccat gaccccggaa ggtcatctat gccctactca attccagctc cggccacagg    1800
gaggtaaaca gccggtgtgc ggccactgaa gctgccagcg ccacgggca cgccactgtc     1860 ttccgctaga tatgtctgtc atacattaaa gctttattgc aggatgtggt gtttaaataa    1920
aagccttagt gttttggaat taggtttgac ggagcagtaa aactggagag tttgcaggga    1980
gcgagcctca gcctccttgg ttataaatca ccttggtgct ctctgcccgc tgagttaaaa    2040
cgagtacccc tggacacccc tcccctcctc ttctcccctt ccgtacatgt ctactcccat    2100
ccccaaggtg tgtgaggacc tgtttctggt gatacctgag aaggtgtgtg gttgtgatgt    2160
ctgctgtatg ggttttcaca ggactccaaa ccattatgct atgtggttgg ccaagtcagt    2220
cttctatggt gtcttagaat tttcacatga aggagaggtg aggcaggctg ggttgggaca    2280
gggatcccca cataggcttt cctagtctgg gtaccaccca gacatgtagc caaaggattc    2340
taagaggtaa aggagcccag ataaggcccc tgggagcaa agaggacatg tcaccacctg      2400
gaacaggttg gggactcaga agccgtgaga aggcatgtgc tccctttatt gagttcactg    2460 gaataggag gcactgattg gtgctcttcg acttccagat gtgcatgtac aggagtcaca      2520
ggtcctgcag tctggcgggg gagcaatagg gtcaagcatc atggtagcaa gcttattgtt    2580
```

```
ccatactatg gtttatacct gatacttagg actgggcagt ctgcagattg gattaagcca    2640
catgagtgtc taagtgagag attatgtgtg catgtgtagt tatcaattat cttcttcctc    2700
cttgtcctcc ttgtcctcct cctcctcctc ttctcctcca cctcctcctc ttcttttctt    2760
cttcttcttt tcttcttctt tcttctttta ttcttcttct tcttttcctt cctcttcctc    2820
ttcctcctcc tcttcctcct cctcttcctc ctcctcttcc tcctcctctt cctcctcctc    2880
ctcttccact tcttcttctt cttcttcttc ttcttcttct tcttcttctt cttcttcttc    2940
ttcttcttct tcttcttctt cttcttcttc ttcttctttg gccaagtgaa ttgtgccagc    3000
ctctttaaag aggggttctg acattgactc cagctaaata aataatgtcg tacctcgagg    3060
gcgataaagc atttttatggc ataggttctt cagactgtgt gctgggctcc tcagcaatct    3120
catttagaac tgttgacttc atgtgaagag aagcatcgaa gaataaacta ttaggtgtgg    3180
ttaggttggc tgcaggatgg ctattttgtc tgccataatc caagtcacag ttaacattgt    3240
tagagctgca tcttacccca acaccaaaat gttgtaactt tataaaagga aggaacctga    3300
gtgatattca gggccagggc aaccgggcac aatgacgaag atgctatcga ggaggaggga    3360
gggatgtgcg tacaattgcg ttaatcgctg ccaccttagc agaatgggta gccagccttc    3420
tgtgaggctt tgtgctgact cagcagccat gcactttgga ttgcaggtct cactctgcag    3480
tacagtgctg ttccctgctc catggccagg tccagggcac cctccttgag gttgggctga    3540
ggttgacttg agtgtggtgt ggaccaatag aggtaggtg tagggtgagg ctggctttat    3600
aaagaacccc agttttgttc actgtcctta cctggccacc aacctcagcc ccagtgtcct    3660
gggtgaatca cacttggaaa gggggcaggc atggctatta ggcagctagg gaagcaaagg    3720
ggcagtacag acagttctca gatgttcttc ttcctgggct cagaacctgg ccagctacag    3780
ttggatttgg aaggttcttt aaggaggttg cttggtgtcc ggggagggaa gtgttctttg    3840
cacttccagt tctcccgggc cggctgtgac cctgggaaga ttggagctgc tgagcgtgtg    3900
ggaggggag cagctacagc agctggagtg gtgcaggctg ctgcagagct gctgcagaat    3960
agccgcagct gcaggcacat gcagggctgc gtgtctcaag ggcagagatc tccggatctg    4020
caggccgggt gggaagggac gaaggcgtg gcacatgggc ctcccaggcc ttctctgtcc    4080
acctgcaggg agggcactga agaagcttta gagtcaaagt gatgggtttg aggttgtggg    4140
ctcttccctg gccaagagtg tcccctacaa agtgatttaa agtctagggt ctctttccct    4200
gaggtcaaac caggggctgg gctaagaata gtgcttcctc actggtgctg ggcagatgac    4260
gtgtgggcag gtgcatgtgc acagggagga tagattcagg ataaaccgga cattgaacca    4320
gagtattttt aactgcaaga aggggagagg gcagctgtcc tggaacctgt catgggggtt    4380
ctatggggac actgtgaagt tgaaggacac cggggacaga tgtgccacct ggaccctatc    4440
ctcctggcag ccccatgagc cctcaatcat gcccagatat ggccacaggg ccgtgtgtgt    4500
ctccccactc ttgcccatgt catggctggt ataaataacc tgcattctca gctgtcctgt    4560
tggagacggc tggacttggg tgacttgggg ctgcagaggc ccaggagtgc tccccacctc    4620
ccatcagcag ctgtgacccg agtgtggctc agagctctgt tttctatgtt tctcctcctt    4680
gtgggcccct cctaggctgt tgagtccagg tgagatctgg ctgcttcctc tcagcccttc    4740
tcaagggcac agtgcggttt tcgctcactg aagaagggca gaagagaaag agtcccagat    4800
cttggagctg gtgtagggga cgccctggtc ttatcactgc aggctgagta ctgtggcagg    4860
cttaagtcgc tgtaagggtg tcctgcacac tctgttttga gatccgccaa gacctcacgt    4920
ttgaggttcc cttttctgat cttgtcattg ctcacttttg tcttagcaaa taaatttcta    4980
```

```
agagtagggt tcacatcaca agacatcctt gtgtaaggga taaaatgttc atctggtacc    5040
ctcaaaggca ggttatactc tcatgtctga agacagtacc ctgtcctgcc atgcctctgc    5100
atcctgggag acctccccca agccataggg agacgaagaa tgggatagag gtgagaggaa    5160
tagcacacac tgtcatgcat tacccaggcc ttccatggtg tcacatggaa cacctctgct    5220
gcttcgtcca acagcatatc tgaactccag gttctaagct ctggtagctc agggtctatt    5280
ttttcaggag atgaggtaca gtatgtgtat ggggcccacc ttccctatcc actgcaggac    5340
ctttaaccag actctgtgtt gacaagccac ttttttttctt gtctctggac acatcagtcc    5400
ctcagaacag aaattctgcc tgctgacctc catggagttc ttatctgcaa cttttccctt    5460
aaaatagaat cagcgattag tagggtccta actttgagat aacacacaca cacacacaca    5520
cacacacaca cacacacaca cacacacaca aacacacact cccacatact acacatgcac    5580
accacacaca cacacacaca cacacacaca cacacacaca cacacacaca ccatctgtgt    5640
tttaattttt gcaacgaaca gcaacacaat cgtgtgtccc gtccctcccc tgcctcctct    5700
gcttgccccc tgttccatgg gtctatttca ggtggaattt atctccagga agggcctcat    5760
caatttgcca tgctcctttg ttgacaagtt tattaaaaac tcaggcaact ctggtattaa    5820
acttttatca gtgttgagaa aagataaatt ttttttgaaca gacagaaacg ttatggatttt   5880
gggctgaatg aggctcggtg gtgctttggc tgagtcagca ctgcagatac aaagaaatgg    5940
tgctgtttgg gggtgaatgc tccctttggct ttttctggag attgtcccat gggacttgat    6000
actctcaaac agaacttcca gaaagttcct gagcagcagc cctggccagg gccgctagta   6060
cccactgggc ttcctgcaat tctttgctct ctattttaat aatgagccac tatgtgaagc    6120
tagatattaa ttttgtggcg aatctgcttg ctagtgggca atgtcactat gtagagaaat    6180
actaggttat tggtgcttac attttacatg ccccacagaa agaaaacaga aacatcaag    6240
tgggagttgg tgtagcggct agctacacat gtgactaggt tcaggttgtc tttgagcagg    6300
agtatttagt attatgacct ctgtgtccct ggaggtggct gtgtattttc agctgctgtt    6360
cctgacgtcc tgagatgagg ctgagagaaa ccctcccact gtccttgttg gccatatagc    6420
caggggtcac ctgtggagct atgacaggca tggaataaca ggacacatag ggctggccat    6480
cagacaaaag gtccagtact tactgccttc aacactttc atgttgggaa acggatcccc    6540
caagaggccc aggaacccca cagtttcctc tagtgtgtag tgttttactc cagagtctga    6600
ggtcattctg agtctcaaag gtcaggcccg gggacagaca gctgggagag cttgctatag    6660
cgtctgacat cctggactgc tctgccatct ccaagcaggg cccagcaggg gtcttggacc    6720
cctggcagat gcaggatgat gcaaatgctt cctggtgagg cagcatcttt gcacagcatc    6780
acgagttcat ggaacttcaa ggggtgagag cgaggtgagc catgtgccag ggactgccgg    6840
catcgactgt gtgtctgaga gtgttccctg ctctgtcctt atctccatca ctctatgctc    6900
caattataac taattgagtg tgtactgcat tttcacggcg tctaattttt ccattgattt    6960
tcaccagggc tgctggtgct ttcagcatcg aatgctcatg tctagtatcc atcgctgctt    7020
gaaaatgctg agtgtacctc tccctcgaag gatggctcca tcagcagatg tttttaaaaca    7080
ttttaaaaac tgttttgtct gtaaaatgca aacaaaaca agcccccaac aacaacaaca    7140
gcaaaacaaa caagcaaaca aaacccaccc caacaacagt agtacccaca gtcccattct    7200
gttcactttg aaaatctggt aaagacagga ttcccaaaga agccatgccc acaggctcca    7260
gaccaaccct cagcagatac tgtgtgtgcc agccacattg ggtatctctc tgctaggcct    7320
```

```
ggcaccatgg ctctaagttg gcccttcagg gctaccatga ccccacaggt tggtttgcct    7380
tctagcatgg tcaggggcac actgtggtag agttgttctt tgctacaatg aagtcagcct    7440
ctcatgtctt gtgtccgagg gagcagggtg gctgaacaaa gatgaccgtg aagaagaggg    7500
cagaacagcc tggatataaa cagttttag gtgaagtaag tacccatgcc gaggaggagg     7560
tgggtcttat ggagaagtca tgggcccttg aggttttgga gctgtgtgta atgtgagcat    7620 cttttttgttg ttcagaaagg aaataaaaca cacccacag ggagttcagg gaggtccgta    7680
tgggggaaat tcctccaatc tggtgacata tggacagaaa taagaacctt cacagggacc    7740
caaggggagt gccagctcta tcatcctgtg acccctctcc ttggcagaat gaaattgtgc    7800
ccaaggcttc ggcaaatgaa gttgcactgg agcaggactt gggcttgaca cattggggca    7860
aaggtagctg cagtcctctt cctcggtccc caacatggta gctaagggcc caggaccaag    7920
actcagggct aattctacct cttgtcaaat cttccactcc agtaactata ttgacagcat    7980
agacaaaggg ttggatgcag ccagcatcaa gaatcatttt cattaagggc cggtgaggca    8040
ggctgggagc ctggtgcctg ccctgtgtag gagcaaggag aggagagcca tgtgctgagc    8100
cagaggctgg tggctgggag atcctctgtg tctgtgtggg ttggaaggca gagccttttcc   8160 tgcaactcca gggggacatc aagacatcct taggaggatc tttctgcatc agggctgctt    8220
ggaaagacca ctgtgaacac aggctgcagt gggccctgtg ggggctgagg atgtggggtt    8280
acccaatggt tctcagaggg gtggtattca ctgaggtag acacacacac acacacacac     8340
acacacacac acacacacac gcacacgcac acgcgcacac acacacacac acacacacac    8400
acacgcacac acacacacac acagagagag acagacagac agacagacac agagacacac    8460
agagacagag acatacacag acagacacac aaacacagag actgagagac agacacagag    8520
agaaaaagag agacagagag agacagagac agagagagac agagagaggg attggagacc    8580
atgtccctgt gcggctgagg acactttcac ctcacaccct tgctccagtt ttctgaaggg    8640
aacgtggacc ttctgaatca tcaagagctg tgaagtgaga ggcttaggga ggccagagaa    8700
tgggggtatg gacactgggc cttttctgtc ccatgtcact tcttatgcta cataaaccag    8760
tccatactgg aatattccat cttctgcctt cccagagcca tgtgtggtgt ctgatatacc    8820
cttgccccca aggtcactac aagccagagc tgtttgccca gtcacagggc ccacggctcg    8880
ctaagagaaa cagccgtacc tcggcacagt gagataagag aacatctgga tgatgcaggc    8940
agagtcaggg tgtaaagtgt gaagtcttca agcctcgatg tgagtccatg ggtcagaggc    9000
tcaatggtct tggatatatt cctgaaagga gtgaccagac aggactctgg acaacgctgg    9060
tgtatatgtg gtatatatgt atatagcaag taagaggtgg aggttcgggg cgtaaggacc    9120
aagaactgct tttccccttc ccagtaatgt cctgggggtg ccatttttggg gcacatagag   9180 tgtctgaatg tacatgtgac ccctcacaca caccctgaag acctccaaag cccttgggtt    9240
tgcatgggtt ctcagagcag ggagagcctg ggacaggaca gcagcctgac agaaccatct    9300
tcttcctgga gtctctcctc ccagtggatc agaagccaaa tgctttgctg aagctggtaa    9360
aatggaacca aatcagctgt tggatggatt tggtcccctt caaccagctg tagctgcgca    9420
ttgatcacgc cgca                                                      9434
```

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer -continued

<400> SEQUENCE: 2
tggaatgtaa agaagtatgt att                                              23

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ttggtcccct tcaaccagct gt                                               22

<210> SEQ ID NO 4
<211> LENGTH: 77
<212> TYPE: RNA
<213> ORGANISM: Artificial Sequence
<220> FEATURE:
<223> OTHER INFORMATION: Synthetic Primer

<400> SEQUENCE: 4
gcuugggaca cauacuucuu uauaugccca uaugaaccug cuaagcuaug gaauguaaag      60
aaguauguau uucaggc                                                    77

<210> SEQ ID NO 5
<211> LENGTH: 104
<212> TYPE: RNA
<213> ORGANISM: Artificial Sequence
<220> FEATURE:
<223> OTHER INFORMATION: Synthetic Primer

<400> SEQUENCE: 5
agaagccaaa ugcuuugcug aagcugguaa aauggaacca aaucagcugu uggauggauu      60 uggucccuu caaccagcug uagcugcgca uugaucacgc cgca                       104

<210> SEQ ID NO 6
<211> LENGTH: 21
<212> TYPE: RNA
<213> ORGANISM: Artificial Sequence
<220> FEATURE:
<223> OTHER INFORMATION: Synthetic Primer

<400> SEQUENCE: 6
uggaauguaa agaaguaugu a                                                21

<210> SEQ ID NO 7
<211> LENGTH: 22
<212> TYPE: RNA
<213> ORGANISM: Artificial Sequence
<220> FEATURE:
<223> OTHER INFORMATION: Synthetic Primer

<400> SEQUENCE: 7 uuggucccu ucaaccagcu gu                                                22

<210> SEQ ID NO 8
<211> LENGTH: 2644
<212> TYPE: DNA
<213> ORGANISM: Artificial Sequence
<220> FEATURE:
<223> OTHER INFORMATION: Synthetic Primer

<400> SEQUENCE: 8

-continued

```
tcagagcaca tacttcttta tgtacccata tgaacattca gtgctatgga atgtaaagaa      60
gtatgtattt tgggtaggta atgtccgcca agaagaagct aaaggaaact ttccaggagg     120
atgacttcca tactctgaat tcacctgtaa tactaacagc cccattccaa aaggaccagc     180
cattcactgg gaaaactaac atcccttata ctgtactgaa gagataagtc ccgtggaagt     240
ggattttaat tttcacatta aatcatacta cactctacac tgaatactca cgtgattaaa     300
atgtgactac tacagaggaa atagtattgc tagcgcaaaa cagtgagaca caggatcaac     360
cattatctgt cttcacaatt ggatatttta gtgtctcaca tctatcaaat caggaccaac     420
aaatctaata agaaaaataa agcaacaaaa agctgatttt actcatataa tagctattct     480
tcacatgtgg caaaatgtat aacctattaa aatcagagga tctcgtaagc caaaaatttt     540
ggtttcatta ttttctttc tgacagctat tgaaactata atgtttaaag actatctttt     600
aagtaaaatt atactgcaca catgaaaact ggcttttgtc cttttccagc ttgtcagttc     660
ttaacccaat ctgtacttta agtgcagtta atacttacag catgaaaaag aatgataaaa     720
atggcaaaac cctaggccac aactaaaatg taaacaggat atattggcaa caaactgtca     780
aaaacctgag tctgtattgt ccttgcttat atcaaatgac attgtttttc tcacaatgag     840
ttatgaacag ctacattagt tattccacag gtctgaaagg ttttcataat tctttaagaa     900
acattttcac aactaataat ttgttacaat ccttagagaa tattagctat tcatttataa     960
aataaaactg aaaactgatt tgttgcttc caagttcagc ttttgtctag gagtgttttg    1020
aatcacttga aatgtcacat ccagcactta gatcagctgt ccctttttgaa gtgagtacat    1080
gttaaactct gggcatctgc tgacactgct attactcaaa cacttcaact gtcaccctga    1140
cagggataac agatgctgac actatcagat gctggactat ttttccccat ggcctctcct    1200
tgtcctgata tggccagtac acgaaactca atgatccaaa agcacacttg agcaactgca    1260
cttgctgact ggctgccagg gacctactaa aatagaacca ggcaagtgct atcttcagca    1320
cttaagttta agcaaccaaa tacctgtttc actatttgga aaaaatgatg caaagaatta    1380
aaattacatt aatttcacca gaagcacaat aattaacaac agatgtagaa tagaatatta    1440
aactatttgc atactgtctg agattgtgtt gtccttctac catattagtt taaaaaaata    1500
aaattatatg gtatttccct cagcattcta attttacaga caagctataa tatatcaaac    1560
ttttattgta tgagtatgtg tcagaagaca ttctcttcag gcaggaaatc tccaacagaa    1620
tcacatcaaa tgcttaagta ctggttttaa agtatcacat ggtaggtttt aatattcaaa    1680
attcagggat tatagccaac taccatacat caatgtatca ctaaccttat aataagaaca    1740
atctatactc aaaacagcat agaatttagt caagaaaata gattttaaa ttttatttta    1800
tttttaatct attttttaca ctccacattc cattccccac ccccacccc ctctaccctc    1860
caactgttcc acatcccaca tctcctcccc accccacctc aataaaatag attttttaaga    1920
aggttaattt ctgaacttag ggttagtatg ccaacataaa caaaagcaaa gaatgacact    1980
gaagatatgt gtgatgtatt aataaattaa aggacagagt tactttctta aggccattct    2040
tatccttcca ctccgtatca gaacttgtta agtcctcagc taaaatagaa gcagtacaaa    2100
aatatgtagc taacatgacc cttttcaac atctagttta attacttaaa aacctggttt    2160
gcaggcatgg tggcagactg ctttaattcc agcacttggg aggcagaggc aggcagatct    2220
ctgtttgagg ctagcctggt ctacagagtg agttccagga cagccaggac tacacagaga    2280
cctgaatgaa caaaccaaca tggtgataat ttagaagcat tactctgaaa cacatgatga    2340
tttatctgtt ctttcaaatg ttggttttga aaggctactg tgtgcattta agaactaagt    2400
```

```
aaagatgcac tgatgtgagc tgcaagaaca gcagtgtagg acatatgcct aaacacgtga      2460
attttctgtt taacaactgg tacactagtg tgggaacctc taatacctgt catgctatat      2520
ttctacaaaa gagcatttaa cctgtttgga tcctacacca gcagcggcaa tgctttgcta      2580
aagctggtaa atggaaccaa atcgcctctc tcaatggatt tggtccccct caaccagctg      2640
tagc                                                                   2644

<210> SEQ ID NO 9
<211> LENGTH: 72
<212> TYPE: RNA
<213> ORGANISM: Artificial Sequence
<220> FEATURE:
<223> OTHER INFORMATION: Synthetic Primer

<400> SEQUENCE: 9
ucagagcaca uacuucuuua uguacccaua ugaacauuca gugcuaugga auguaaagaa      60
guauguauuu ug                                                          72

<210> SEQ ID NO 10
<211> LENGTH: 68
<212> TYPE: RNA
<213> ORGANISM: Artificial Sequence
<220> FEATURE:
<223> OTHER INFORMATION: Synthetic Primer

<400> SEQUENCE: 10
gcuaaagcug guaaaaugga accaaaucgc cucuucaaug gauuuggucc ccuucaacca      60
gcuguagc                                                               68

<210> SEQ ID NO 11
<211> LENGTH: 21
<212> TYPE: RNA
<213> ORGANISM: Artificial Sequence
<220> FEATURE:
<223> OTHER INFORMATION: Synthetic Primer

<400> SEQUENCE: 11
uggaauguaa agaaguaugu a                                                21

<210> SEQ ID NO 12
<211> LENGTH: 22
<212> TYPE: RNA
<213> ORGANISM: Artificial Sequence
<220> FEATURE:
<223> OTHER INFORMATION: Synthetic Primer

<400> SEQUENCE: 12
uugguccccu ucaaccagcu gu                                               22

<210> SEQ ID NO 13
<211> LENGTH: 4337
<212> TYPE: DNA
<213> ORGANISM: Artificial Sequence
<220> FEATURE:
<223> OTHER INFORMATION: Synthetic Primer

<400> SEQUENCE: 13
agcttgaagc ttccacccat agtcccagag tcgtctcaat ggcctgtact tgacagtagc      60
agggtggtag agactcgctc aatgtcactt tgctcaaagg ggatagttgg ccaatcccag     120
gctgctggac tcaggaatcc cagcccagtg gggccatgtt cccaagccgt gtttcttata    180
```

-continued

```
caacccaggt gggaacaaaa tggagccatc gccaagtgta cttgtggata tgggggtctc    240
caagccacac acccttgatg ccaaggttct ggaggagaca ggacaactga gttggccttc    300
tctgttgccc aaggtgacct gcaattctca tgacctgggg ttggcttagg atccccagga    360
aaaccagtgg ctctgttgcc acctgaccca accccacttc tgagcaaaaa ggtatcactc    420
tggagacact gaggccctgg cccacatggg cctttagggg actaaggcca gggagccacc    480
catctccctc cctgggccct gttccctgga gtaactccag tctccccagg cactcagga    540 atgagttggt gtcgcctcag agagaggcca gtgcccactg ggtaggaggc acctctgtac    600
tgggccttgc taaaaatagc aggggggattc ggacagggac agccggtagc aggctcgtaa    660
gggaggggct gggaggggga cggggcaacc caggaccgct gtcaatggtg ccggggctcc    720
caccctgttc cctgctgcct ggccagcctc ggcccagctg acatgctatt ttttcccctg    780
cttgactaaa tatggtcagg gcgcacagcc cgaggggggc cacttggccg ggccgcgtgt    840
ttgggatgtt tggcggggta tataagaact accaaggtga ggtcgctcct gatccaaggg    900 cccccttgccc caccagcgtt gggtcaggcc atcccgtctc tgccctcccc tcccctgca    960 tgcatgaatc ttggtctgtg gggctgcgtg cgtgtgtgag cgtgcatacc cgcggggcct   1020
ttctcttttt ccctttgtt ctgctctgac ctctacctgg taccgacagg gctgagggtg   1080
caggagcttc ctgcagcttc ggccgggcaa ggtgtgcagc tgggctctgt ctccttaact   1140
ctgcatcagc gctctctctc tctctctctc tctctctctc tctctctctc tctctctctc   1200
tctctctctc tctctctctc ttaccctccc ctcccctttc tctccccccc ttcctccttc   1260
tctctcaaga tttccctgct gctaagtctg cgctgctgca ggagggctgg gggaagggca   1320
ggggtgcgga gtcggggtgt cttctttctc tctctctctc tgccccccc tccccaccaa   1380 gtgcggacgc aatgggagct ccggcccgcc cccaccctg catttgcgat ggctccggg    1440 aggaggtggc taccgctgct gccgctgctg cagcatctcc cggggagccg cgaccctgcg   1500
cccgccgcca cggctgccgc ggtcaccagc ccagcccgag gggcgcccag ggctccctgg   1560
tgagtccctc tcagctggct gcttcagctg cccaccagct aggaaagccc ctgaaaactt   1620
atcggcagtg gtggggtgt gccctccggt gaggtgggtg ctgtgggtgc tggtgccgcg   1680
tggcttcaag ggggcgcctg gagtttctcc cagcatcatc tacatttgga aaactgcaga   1740
gccagcagcc agcagggctg ggagggttgg gagggcgcgt ccaaccggga tgcagaactt   1800
tgacatacgg cttttttgcaa gaaagcagcg cccctggatg cttggtggag ggcagggtgg   1860
atggcgtccg ctgttctagg gggttggcac gggagctgag gaaatagatt aaccagttga   1920 ggcaacacc agagattgtg gctaaactta ccttggaact tgccacaaag cctttgagtg    1980
cttgcgggtg ggggatttct gaggagcgct gacaaggccg tccatgggct gggactctgg   2040
atttctgaag ctctcccagc cctgccagga tcagaagtgt gctgtgtcag gcatccaggg   2100
gctggagctg ggctggggc tagggctgaa ctagtgttca tagtgtgtgt gtgtgagggg   2160
ggggggggct caggataagg ccccacccca gatgccagag gggtctactt ggaggtgact   2220
gacaccactt tcctgtcaag gtgggaaact ttttgagaag tgactctcat tcattcctga   2280
atgagcagct cctgaagatg tgggctcaga ctgaatcaat ctctgctctt caggtccccc   2340
caactttctg tttgacatac agacgctatc atgaacacct gggagttggg acagagggca   2400
gagaggcatt tgttcttaga gttctcaggg agcctaagtg ggagctcagt cacaccaggg   2460
gtacctccag aagctggaag ctgaggctga tggactggct gcccttttta tccttggcta   2520
tgtggaaatg aaattttaac agcaaccaca tgggaaatgg gcacagtttc tgtccctcgc   2580
```

```
tcattcctgc tgcacaagct tctctcagta tcctaatcct ctttccaccc tgcctagcta    2640
cagctgccac aaccagggga cctctacatg ctgcaggctc tgcagagaca gggccctccc    2700
aggaatggga gagtctggat gctctctggg gtgtttccac acagggacag ggctggtcag    2760
gtcatgccag agacagacat tgtcctgctg acacggaaga actgaatgtt ctttcaggag    2820
ctgggactgc cctgcagccc cacaccaggt ccaagcccag ccagaccctc tgtgcctgca    2880
ccacctctcc tgcagtgggt gtctccagct ctttctgtag gtagccgcct gcagggacac    2940
ctgttccagg gttccagcac tttacctgca ggctcacctt gggtgatggt gagtccccag    3000
gcatgtgagt ctcttcctcc ttttctccct cctcctcttc ctcccccccc ctccagacca    3060
ctgctttctt cttccccttc tttctctcag tctgaggata gcctcccttt tgctgctgag    3120
gctctgacct ggaagtcctg cccatctttc tgttttccac attcctttct tcctcactct    3180
gggtgtagaa gttggtaggg cagaagggag cctccacttc acttgcggcg agatctcaaa    3240
aatcaagagg agagacaaaa tataactaag tttcccaagc atttcccttg aacttttttt    3300
ttttcaaatt agcctatagt ttttttttt tgttgttttt ttttttcag aagttggtac      3360 agcaaacagg cggacagccc ctttgtgtag ctacaaacta ctattgatca gggactgatg    3420
gatcaggaac taggtgaggg acagggccct tcagaaatag cctccagatt ccatgggag    3480 cggttcctta cgaccatctt acatggttat gctgcatagc aggggatggc gttggagact    3540
gtaggtcacc aggaggacag agggtacaga agcgagaaga gggaagggga ccaaagaagg    3600
aggtagctgg aatagaaact ccctcattgg cttggcatca actctcaggc cagactgagc    3660
cccaaagagc tggccaagga gtaggtcacc tcttagtagc ccctagacac tgtgaattca    3720
agatcactat cttcttcttc cacttcaaag aaagaggcac tgagaccttc tctcggggac    3780
tctcattttg ggaaacaatt catcagggtc ctgccagggg agccatcgcc tgtccaggta    3840 agcccttga ttcatttctg gagactcaca aaactgcttg ttttcatctg tcctcaggga    3900
gctgggctgt tcaagtcccc aggaaaagga tgtgactggt tcttagtctg gggtacgggt    3960
ccctgatggc tcgtgggtgg agctgctcct gaattctgtc tccttacccc accctcactg    4020
tccttggtgg tgacaaggtg ggcaggaagg agagagaaga tgttagtaga gttggatgct    4080
atttcttaga gtctgggatg tgacttccct ctgttgggaa gaatgggaaa gaactcattc    4140
cgttgaggga ggtgtaagca acggtgggga tgaaaagggt tttgagactt ttcagcacgc    4200
cctgtctgct tccagtcttt accaagtgtg catgtgtgag agagactgag acacaggcga    4260
caccaaaagg gggccagctt gtggagggcc acttcctcgg agtcctgttc ttgtgcacac    4320
tgaacctacc tgcttgg                                                   4337
```

<210> SEQ ID NO 14
<211> LENGTH: 10
<212> TYPE: DNA
<213> ORGANISM: Artificial Sequence
<220> FEATURE:
<223> OTHER INFORMATION: Synthetic Primer

<400> SEQUENCE: 14
ctaaaaatag                                                           10

<210> SEQ ID NO 15
<211> LENGTH: 10
<212> TYPE: DNA
<213> ORGANISM: Artificial Sequence
<220> FEATURE:

<223> OTHER INFORMATION: Synthetic Primer

<400> SEQUENCE: 15
ctaaatatgg                                                              10

<210> SEQ ID NO 16
<211> LENGTH: 336
<212> TYPE: DNA
<213> ORGANISM: Artificial Sequence
<220> FEATURE:
<223> OTHER INFORMATION: Synthetic Primer

<400> SEQUENCE: 16
tttcctagtc tcagcacaag ctcggggaga atctgggaaa tgtaagtgga aacatgagac        60
acggctctat ttagcagtac ttaaaaaaaa aatagcagga caaatggcaa agcagtgttg       120
ggaccacagg aagaacaatc aataggcaga aagcaagata gaatcctcct cagcttttag       180
atcgacaatc gacagctgag agactatttt ttgctatggc tgactaaata tggtcaggga       240
agagagaggc acaagagagt ctgtttgcct gggagtgcat gtttcaaatg cttagctgcc       300
tataaagctc gagcagccta ggctgtggcc actgag                                 336

<210> SEQ ID NO 17
<211> LENGTH: 6
<212> TYPE: DNA
<213> ORGANISM: Artificial Sequence
<220> FEATURE:
<223> OTHER INFORMATION: Synthetic Primer

<400> SEQUENCE: 17 cagctg                                                                   6

<210> SEQ ID NO 18
<211> LENGTH: 10
<212> TYPE: DNA
<213> ORGANISM: Artificial Sequence
<220> FEATURE:
<223> OTHER INFORMATION: Synthetic Primer

<400> SEQUENCE: 18
ctaaatatgg                                                              10

<210> SEQ ID NO 19
<211> LENGTH: 21
<212> TYPE: RNA
<213> ORGANISM: Caenorhabditis sp.

<400> SEQUENCE: 19
uggaauguaa agaaguaugu a                                                 21

<210> SEQ ID NO 20
<211> LENGTH: 21
<212> TYPE: RNA
<213> ORGANISM: Drosophila sp.

<400> SEQUENCE: 20
uggaauguaa agaaguaugg a                                                 21

<210> SEQ ID NO 21
<211> LENGTH: 21
<212> TYPE: RNA
<213> ORGANISM: Xenopus sp.

<400> SEQUENCE: 21
uggaauguua agaaguaugu a                                         21

<210> SEQ ID NO 22
<211> LENGTH: 21
<212> TYPE: RNA
<213> ORGANISM: Danio rerio

<400> SEQUENCE: 22
uggaauguaa agaaguaugu a                                         21

<210> SEQ ID NO 23
<211> LENGTH: 21
<212> TYPE: RNA
<213> ORGANISM: Gallus sp.

<400> SEQUENCE: 23
uggaauguaa agaaguaugu a                                         21

<210> SEQ ID NO 24
<211> LENGTH: 21
<212> TYPE: RNA
<213> ORGANISM: Gallus sp.

<400> SEQUENCE: 24
uggaauguaa agaaguaugu a                                         21

<210> SEQ ID NO 25
<211> LENGTH: 21
<212> TYPE: RNA
<213> ORGANISM: Mus sp.

<400> SEQUENCE: 25
uggaauguaa agaaguaugu a                                         21

<210> SEQ ID NO 26
<211> LENGTH: 21
<212> TYPE: RNA
<213> ORGANISM: Mus sp.

<400> SEQUENCE: 26
uggaauguaa agaaguaugu a                                         21

<210> SEQ ID NO 27
<211> LENGTH: 21
<212> TYPE: RNA
<213> ORGANISM: Rattus sp.

<400> SEQUENCE: 27
uggaauguaa agaagugugu a                                         21

<210> SEQ ID NO 28
<211> LENGTH: 21
<212> TYPE: RNA
<213> ORGANISM: Pan sp.

<400> SEQUENCE: 28
uggaauguaa agaaguaugu a                                         21

<210> SEQ ID NO 29
<211> LENGTH: 21
<212> TYPE: RNA
<213> ORGANISM: Pan sp.

```
<400> SEQUENCE: 29
uggaauguaa agaaguaugu a                                        21

<210> SEQ ID NO 30
<211> LENGTH: 21
<212> TYPE: RNA
<213> ORGANISM: Homo sapiens

<400> SEQUENCE: 30
uggaauguaa agaaguaugu a                                        21

<210> SEQ ID NO 31
<211> LENGTH: 21
<212> TYPE: RNA
<213> ORGANISM: Homo sapiens

<400> SEQUENCE: 31
uggaauguaa agaaguaugu a                                        21

<210> SEQ ID NO 32
<211> LENGTH: 27
<212> TYPE: DNA
<213> ORGANISM: Homo sapiens

<400> SEQUENCE: 32
tgcttgacta aatatggtca gggagcg                                  27

<210> SEQ ID NO 33
<211> LENGTH: 27
<212> TYPE: DNA
<213> ORGANISM: Mus sp.

<400> SEQUENCE: 33
tgcttgacta aatatggtca gggcgca                                  27

<210> SEQ ID NO 34
<211> LENGTH: 27
<212> TYPE: DNA
<213> ORGANISM: Gallus sp.

<400> SEQUENCE: 34
tggttgacta aatatggtca gggagga                                  27

<210> SEQ ID NO 35
<211> LENGTH: 24
<212> TYPE: DNA
<213> ORGANISM: Danio rerio

<400> SEQUENCE: 35
tggttgacta aatatggtca catg                                     24

<210> SEQ ID NO 36
<211> LENGTH: 18
<212> TYPE: DNA
<213> ORGANISM: Homo sapiens

<400> SEQUENCE: 36
tgggctaaaa atagcggg                                            18

<210> SEQ ID NO 37
<211> LENGTH: 18
<212> TYPE: DNA
<213> ORGANISM: Mus sp.
```

```
<400> SEQUENCE: 37
cttgctaaaa atagcagg                                                    18

<210> SEQ ID NO 38
<211> LENGTH: 18
<212> TYPE: DNA
<213> ORGANISM: Gallus sp.

<400> SEQUENCE: 38
ctcgctaaaa atagcaga                                                    18

<210> SEQ ID NO 39
<211> LENGTH: 27
<212> TYPE: DNA
<213> ORGANISM: Homo sapiens

<400> SEQUENCE: 39
tggttgacta aatatggtca gggaaga                                          27

<210> SEQ ID NO 40
<211> LENGTH: 27
<212> TYPE: DNA
<213> ORGANISM: Mus sp.

<400> SEQUENCE: 40
tggctgacta aatatggtca gggaaga                                          27

<210> SEQ ID NO 41
<211> LENGTH: 27
<212> TYPE: DNA
<213> ORGANISM: Gallus sp.

<400> SEQUENCE: 41
gggttgacta aatatggtca gggaaga                                          27

<210> SEQ ID NO 42
<211> LENGTH: 14
<212> TYPE: DNA
<213> ORGANISM: Homo sapiens

<400> SEQUENCE: 42
tcgacagctg agag                                                        14

<210> SEQ ID NO 43
<211> LENGTH: 14
<212> TYPE: DNA
<213> ORGANISM: Mus sp.

<400> SEQUENCE: 43
tcgacagctg agag                                                        14

<210> SEQ ID NO 44
<211> LENGTH: 14
<212> TYPE: DNA
<213> ORGANISM: Gallus sp.

<400> SEQUENCE: 44
tcggcagctg ggag                                                        14

<210> SEQ ID NO 45
<211> LENGTH: 75
<212> TYPE: RNA
```

<213> ORGANISM: Unknown
<220> FEATURE:
<223> OTHER INFORMATION: miR-1 wild-type sequence

<400> SEQUENCE: 45
cuugggacac auacuucuuu auaugcccau augaaccugc uaagcuaugg aauguaaaga    60
aguauguauu ucagg    75

<210> SEQ ID NO 46
<211> LENGTH: 77
<212> TYPE: RNA
<213> ORGANISM: Unknown
<220> FEATURE:
<223> OTHER INFORMATION: miR-1 mutant sequence

<400> SEQUENCE: 46
gcuugggaca cauacuucuu uaguagccca uaugaaccug cuaagcuaug gauacuaaag    60
aaguauguau uucaggc    77

<210> SEQ ID NO 47
<211> LENGTH: 44
<212> TYPE: RNA
<213> ORGANISM: Caenorhabditis sp.

<400> SEQUENCE: 47
ucccugagac cucaagugug aguucccuga gaccucaagu guga    44

<210> SEQ ID NO 48
<211> LENGTH: 544
<212> TYPE: DNA
<213> ORGANISM: Caenorhabditis sp.

<400> SEQUENCE: 48
atttcctcat tcgctctcag gcaacattca aaaaaaccc tcaggcaatt tgtcaaaact    60
ttggtctctc atcatatatc ttacctcctc ttgtcacaca accccgtcc caaatttaga    120 tcccaactca agtgttttc tttttttttc ctttcctcta tattttgttt tctattcaca    180
attgtgtctt ttttcttacc tttccgacta gtgccccaaa tttctcgtca tttcgattac    240
tccaaaccaa ctcagggaac ttttttcattg aactcaggat tcattttcta cctcagggaa    300
ccacttttac tccaactttc taatatcaaa accaattagt cacgaattta gtattttat    360 atatttctat ccgccctatt tttagctttt attgtaaaaa ccaatcagga acatttgaaa    420
atgatctcat ttgaaaaacg aaataggcac cagaatgatt ttcaaatgat tctgattatc    480
atctacactc aatgctgtca aaaaactcaa attccgctca gggacctctt tttctcattc    540
ttct    544

<210> SEQ ID NO 49
<211> LENGTH: 492
<212> TYPE: DNA
<213> ORGANISM: Caenorhabditis sp.

<400> SEQUENCE: 49
tttgtctcac ctcaaaaatt gctctcaggc aacattcaaa actcaggcaa tttgtcacct    60
tggtctctca tcatatatct tacctcttgt cacaccccc atccccagtc tcaagttcat    120
ttcttacttt gtaactccgt ttagtgcgc caattctcgt cattttgatt acactctctt    180
ttaatccaac tcagggaacc aatttttttt ctcattgaac tcaggattct tctacctcag    240
ggaaccatta cctcatccac ttttcagttg tttggggcca aatatctata tccaaagtag    300

```
tagtctacaa tttagtattt tattattacc tcccgccgtt ttagcttta atgttaaaat        360 caggaacttt tgaaaatgat cttcacctca ttcagaagca aaaatcaggc attttccaaa        420
gattttgaaa acacataaac ctccttccaa gtcaaaactc acaaccaact cagggacctt        480
tttcttactt ct                                                           492
```

```
<210> SEQ ID NO 50
<211> LENGTH: 504
<212> TYPE: DNA
<213> ORGANISM: Caenorhabditis sp.

<400> SEQUENCE: 50
tcagtctcac ctcaaatttt gctctcaggc aacattcaaa actcaggcaa tttgtcacct         60
tggtctctca tctatatctt acctcttgtc acacccctct cgtcctcaag tgttttttct        120
ttttattgtt ttatattcca aattgtcttt taaattccga ttagtgtgcc caattctcgt        180
catttcgatt actctatcca actcagggaa cttttcattt tttctcattt gaactcagga        240
ttcttctacc tcagggaact acttttacct catccacttt tcagttgttt ggggccaaat        300
ttatatatcc aaaagtgcta gtgcacactt ctagtatttt attattaccc aaccttctag        360
cttttattgt caattcagaa acatttgaaa atgatttcct cctttcacca gacggtgcaa        420
ttcagatgac atcttcaaac gattctgaat acaaacactt ctgtcaaaac tcacatccaa        480
ctcagggacc ttctttttc ttct                                               504
```

```
<210> SEQ ID NO 51
<211> LENGTH: 40
<212> TYPE: DNA
<213> ORGANISM: Caenorhabditis sp.

<400> SEQUENCE: 51
cctacctcct caaattgcac tctcagggat tcttttttt                                40
```

```
<210> SEQ ID NO 52
<211> LENGTH: 40
<212> TYPE: DNA
<213> ORGANISM: Caenorhabditis sp.

<400> SEQUENCE: 52
tctacctcct caaattgcac tctcagggat tccaattttg                               40
```

```
<210> SEQ ID NO 53
<211> LENGTH: 40
<212> TYPE: DNA
<213> ORGANISM: Caenorhabditis sp.

<400> SEQUENCE: 53
tctacctcct caaattgcac tctcagggat tttttaaatg                               40
```

```
<210> SEQ ID NO 54
<211> LENGTH: 21
<212> TYPE: RNA
<213> ORGANISM: Caenorhabditis sp.

<400> SEQUENCE: 54
ugagguagua gguuguauag u                                                  21
```

```
<210> SEQ ID NO 55
<211> LENGTH: 602
<212> TYPE: DNA
```

<213> ORGANISM: Caenorhabditis sp.

<400> SEQUENCE: 55

| | |
|---|---|
| gccacggttg gcgaacgggt aaaaaggaag agccgatcgc ctcgttactc aaggaaaagg | 60 |
| ctcgacgtcg ttttatctga aaattctttg atatttagag aaatttgaga atatttcgat | 120 |
| gagattcatg taggtttttc caaaaaatcg aacgaatttt gtcggaatat ttgaaatctc | 180 |
| aggaaaagtc taaagaatta aaacacccac aatagcacct cttttcctca aattgcacca | 240 |
| actcaagtat acctttata caaccgttct acactcaacg cgatgtaaat atcgcaatcc | 300 |
| ctttttatac aaccattctg cctctgaacc attgaaacct ctcccgtac tcccaccaat | 360 |
| agattattgc acttttctga gagttttttct gtgttggaat cataatttc taaactgatt | 420 |
| cgcataattt ccaacactga aaactttct caacacctct ggtgactatt ttcttttccg | 480 |
| gtgttaattg tcccaattgc ctaatgtccc cagtgttcat ttaagctccc catttatttt | 540 |
| tatttcactg tcttggtttt tgtgccctag cgctaaatat tgttttatt taatgcatgc | 600 |
| tt | 602 |

<210> SEQ ID NO 56
<211> LENGTH: 647
<212> TYPE: DNA
<213> ORGANISM: Caenorhabditis sp.

<400> SEQUENCE: 56

| | |
|---|---|
| ctgaatcccg gatttatatg agccctgttt tttttaaatg ttgtattcct caaagtattt | 60 |
| cggaggagga gattatcagt agttttcgg aggaatctaa ttttatcaaa cttttggtgt | 120 |
| cgactttcta gatattttc taaaacataa tctagaaatg gacttcattc gtccaaaaat | 180 |
| tactgtaatc ttctatctcc aggatcccca ttcactgtaa ttacagtacc ctatagcttg | 240 |
| tttaaaatca actatcacct ctctgcaccc acctcaagta ccctttatac aaccgttcta | 300 |
| cactcaaagt cattttatg gcgacccctt tttatacaac cattctgcct cagaatttcc | 360 |
| ccaaatacaa aaacgtcctg tttgtgacaa attgcacttt tccgttgttt ttcaattttg | 420 |
| gaaatgactg aaaatgtgga tttcattcct agaaaggtta ataatcccca ttttcagcc | 480 |
| actttcagat ttgaaaaatg actaatattg tctagttaca tggtgactat gtccggtgtc | 540 |
| aattgtcccc cactttcccc cttatatgca ccttttatg gtcttttctc ttttgaccc | 600 |
| cgctatttct ccgaaaattg cgccaaata ttgttttaat gcatgct | 647 |

<210> SEQ ID NO 57
<211> LENGTH: 675
<212> TYPE: DNA
<213> ORGANISM: Caenorhabditis sp.

<400> SEQUENCE: 57

| | |
|---|---|
| gaaaagggcg caaaaactat atatgtattc tcccccgaat cccggctct tgttttatct | 60 |
| ttttggctcc gccccctttt aattattctt gttcgtcata cagttatgca gttttctcg | 120 |
| tcaccatttt aatggttttt ccctttcgcc ccgcccccat gccttttttc tatgagcccc | 180 |
| attttctct aggatcaaat ttccattttg aaaagagctt tttctaaaaa agctcttttt | 240 |
| ttcgggattt tttgactccg cccactttt gtcccgccc ccctcatcac actcctctca | 300 |
| agtacccctt tatacaaccg ttctacactc aaaaacaccc cttttataca accattctgc | 360 |
| ctcttcccgc ctcctctttt ttggaaaagt tatatatatt gcacttttttt tgaaaaaaaa | 420 |
| accaattttt gggtctaaaa aaattatcga caaaaaactt ttttgactc taaaaattgt | 480 |

```
tttttttcaaa aacaaatttt ttgaaaattt tccggtgtca attgttgtct ccacacactg    540
caccctcctg ttttttttctg gctccatttt gtgtaagccc cgccccctcc ctaaaaatag    600
ccccgcccct ttcctctcg gaaaagaaa tagagccaaa tttaatatat aaaaatattg      660
ttttaattgc atgct                                                      675
```

<210> SEQ ID NO 58
<211> LENGTH: 1100
<212> TYPE: DNA
<213> ORGANISM: Caenorhabditis sp.

<400> SEQUENCE: 58

```
tagtcctacc ctacctttat atacctcgcc tcccccttcc gaatcaacgt tgcctacccc     60
aaaacgattc tagccacatt tcccctctta cctcatcccc ctatactcac acaatcttat    120
ttaaacgtta gcaaatttat catatcattg cttatatcct cttttttctt caaatattct    180
atcagttatg tcttatgtct taaggccaga aatttattg gcaaagagaa atcaagagg     240 ttctcttccc caataaaatt agctggctat atacggttac agttttctt ttcttttctc    300 tcctgcgagt tgatgttcgg tctccggtt tctctgttct acttctcctc ctaactagaa    360 accattttt atcccagcat ccggtcgtgt taacttctct aaaatctctc aaaatccttc    420
atcccagtag ccctttgttt tcaaattccc agttatattg ccgtctattg tattatgtga    480
ttcatacaac ctaaccccta cctctatata ctcaaccact caaatatctc agattttcat    540
tcgaagaact ggtctggcac tgttgaattc ttcatttgaa ttttgtaatt ttttttcaaag   600 tttcgttgtt gagtttcttt cattttttccg tctctttctc catcccaaat tctccctggc   660
attttgttca tcttctaaga tttctttcgt attttttgtgg tcctgtagtt taccgattttt  720 tgtgcgcacc cgaaaattct tcagtcctaa aaaaaagtca attcttgctt aataacttaa   780
tgttttattg tgatttgtca ctatttcatt gtgattttgt gattgagaaa ccccctatct    840
tcttcttttt ttgtttcaag tacaattttt cccgatttct atctttcccc ttcccactac    900
cactgcactt ttttttcctac acacccttttc tttttctgcac actggtcttg taaagctacg   960
gtgatactaa tggactgtac tgtagcctat gtaactgttt ttccctgct agctcttctt    1020 cttcttcttt tcctctttcg taattataca acaccacacc tctatttttc ttttgcacta   1080
cctcgatcac accatttctc                                               1100
```

<210> SEQ ID NO 59
<211> LENGTH: 1120
<212> TYPE: DNA
<213> ORGANISM: Caenorhabditis sp.

<400> SEQUENCE: 59

```
tagtaccact tcaaacctcg tcaactgatg ccatgccata tcactatacc tcacaatcaa     60
cgttgcctcc atcattaaaa ttctagccac atttcccacc ccttacctcg aaacttcccc    120
ccagcatccc ttctgacttg tcttatacct ctcctgtttt cttgaatagg aactagtcac    180
tatcatatca ttgcttatat cttttttcgt ctcttattct ttttgttcat tcattttttct   240 tgaaaccagc accgaacaat attgttgaag aagaagggct gaatagtaca acaaaaaacc    300
aaaaaaaaat tcaaaaaaca aaaaaatttc caatcactaa aaatccttct tctccaacaa    360
aatttcctgg caatacggtt attctttttct tttgcgagtt gatgttcggt ctccggtttt   420
catgttctac ttctgactag aaaccttttt ctatccaaca tccggtcgtt tttctcttgc    480
```

| | |
|---|---|
| taatctcttc aattcagccc agtagttttc acatccccgt ttattgccgt tcattgtatt | 540 |
| attttagtca tacaaccgta cccctacctc taattttctt atctaactat ctcattgaag | 600 |
| aactggtctg gtactgttga atcttcatgt agatcgctca tcttattccc gttcctagtt | 660 |
| gtcgccctat ctgttttccc ccttgttccc ctctcctcac cttctcaaag ttttcctcc | 720 |
| acagccggca ttttttcag atttctttcg tttttgtggt ctgtagttta ccgattcctg | 780 |
| ctcgcgccca aaagttttca aaaagtcaa ttcttgctta ataacttaag tttctattgt | 840 |
| gatgtgtcac tatcttattg tgatttgtg attgagaatc taatcatccc tttatctgtc | 900 |
| ttttttaaag tacaatttgt tcgatttcta tcttttccc catcccgcac catctttct | 960 |
| tcacactctt tcttttcaac actgcactgg ttctgtacag ctacggtagt taactgactg | 1020 |
| tagccctatg taactgtttt ttcttcttt tctcttttt aatatgcaac accacacctc | 1080 |
| ttccttttcc tcgtctacct cgttccctct ccaatttctc | 1120 |

<210> SEQ ID NO 60
<211> LENGTH: 1053
<212> TYPE: DNA
<213> ORGANISM: Caenorhabditis sp.

<400> SEQUENCE: 60

| | |
|---|---|
| tagaaatcat ctaccaaacg atgccatgcc tcaataccte acaacttgat tctatattgc | 60 |
| ctccatccaa caaactcaat ctagccacat ttcttctttt tcacgtacct caaccaccct | 120 |
| ttccatccta caaatcgtat aatattcctc tacctctta accaattcat catcttttta | 180 |
| tattgttttt atttgcattc aacttggaaa tagccactat tcatatcact attgcgtatt | 240 |
| tcctttcatt ttcttgtctt attttcttga gaccagcacc agaagatttt ttcgatggag | 300 |
| aactaagcat gataatttga agttttccat ttaaaaatg caggtaatac ggttaattca | 360 |
| atctgcgagt tgatgttcgg tctccggttt tcatgttcta cttctaatga ctagaaaccc | 420 |
| ttttatctaa catccggtcc tcctatccct aatgtaccca gtagatattt ttccccgaa | 480 |
| tgattaaacc tcccagtcaa atattgtatt tgtgattca tgcagcctag cccctacctc | 540 |
| ttaattccgt caatactatc tcagattttc attgaagaac tggtccggaa ttattgaatc | 600 |
| atcagctaga aaatggtttt cctcagtcat tttaaactt ttttctattt aagactttca | 660 |
| actcccaacg cctggcattt ttttgtttca gatttctttc ttttgtggc ctgtagttta | 720 |
| ccgattcatg cgcgcaccca aaaattca acaagtcaat ttcccgctaa cgttatattg | 780 |
| tgatgtgtca ctatttatt gtgattatgt gattgagaat ttactgcttc tacatctatc | 840 |
| ctctatccct gttcagtaca attttgactt tctatccttc cttcttcagc accacctatt | 900 |
| tcttttcaac actgcactgg ttcatgttta gctacggtga atttatcttg acagtagctt | 960 |
| atgtaacttt ttctgtctgt cttttctctt ttttaatatg caacaccaca cctctatttt | 1020 |
| ccttgcacta cctcgatcac acctccattt ctc | 1053 |

<210> SEQ ID NO 61
<211> LENGTH: 1150
<212> TYPE: DNA
<213> ORGANISM: Caenorhabditis sp.

<400> SEQUENCE: 61

| | |
|---|---|
| attttctca gccttcatcc ctacctcaaa acatattccc atacttgtat taaatgccaa | 60 |
| aacgaagata ttcaattcaa cccccactc tcatcttgta ttctcagaac gtgtcactac | 120 |
| ttagaagtaa ttgtatactg ttgtcagtac atgtagtacc cccaagaata cttgtttcag | 180 |

```
ttactatgta ccctttcaat tattcgggat aggtattctt tttgtgtgct ccatttctc      240 cagatgtcat tttcttgttc atttctaatt ctaagctcct cctcctctaa taagctttaa      300
ttgcatgtct ttcacactta tttattttct atttgccaat tgtttaatat gtgcaacact      360
tgttttgatg ttacagttct ctatgatcta gcatttgtg tatttttcct tctcattgca       420
accaaacccc tacctctcac acctcgaaat cattgcgaac tctcatgtcc atccaaatcg      480
tgttgttctt tattcttacg gttttgatgt ttcctccacg gaatcaggga ttgtagcgca      540
gttttaaccg ttttgaacta gaatatgcca aagattcgtt attttcatct agttgtcatt      600
aatttttata gccgaagtga ccatccatcc ccgcttttct caattgtttc cattttctc      660 tactaataac cgttttcta ttttccctat atttatcttt ttatgtacct ctttcacgct       720
cccatgtcct cacgtgatca atgatttcac agaactcgta actatctcgc accatcattc      780
tacctcaata catcccagct tttgccatac attctccgat tcgaattctt gtgtgctttt      840
ctcaaataat catttccttt actcgtatta atcgttttc ttacctcctt gctcccatct       900
atctcaggaa taatccagcg tttctttttct cttgaatgct cgctccaact ctatgaatta    960
cttgtccgat tacagtttct tctctatgta cctcattgat tcttttgcca tccgatttat     1020
acctcaattc caatactggc tatgactgta taatgccttc tacctcccaa ttttccacaa     1080
ttctagttaa tttaccattt tctacctcag cccatgtttt cttatacaac cgtttccacc     1140
tcaagccttc                                                            1150
```

<210> SEQ ID NO 62
<211> LENGTH: 1220
<212> TYPE: DNA
<213> ORGANISM: Caenorhabditis sp.

<400> SEQUENCE: 62

```
tttttctgtt tatcatccct acctcaaaac atattcccgt acttgtttca atgacgccaa       60
aacgaaaata cctaaaagag ccttactctc tgtaccccca atctattaaa cgtgtcactc      120
ttagaagcaa ttgtatactg tttgccaaag tacatgtagt accccttctc ctccagaata     180
cttgtttctg ttactatgta ccttctcaat atttcgggat atggaaattt ttcttttgcgt    240 gctccaaaaa aaccttcaaa tgatttcatt ctcatttttt ctcaatttct aaggcccctt     300
ctccactaat aagctttatt ctcttttgca tgtctttcaa acaacttatt tattttctat     360
tcacccaatt ttttaatatg tgcatgattc ttctttcttg ttatagcatt ttgtgtattt     420 tcccctaat tatagccccc tacaaccgtc cccctacctc tctccccaaa atcatacga      480 actcgtctct tgtccatccc ataccaactc gtgtctcctt tctttttttc ctacggttat     540
cgtggttccc aacattttgg gaatcagaga ttgtattgca gttttaaccg tttcgaacta     600
gaattcatgc caatgattcg tttttcatct agtttgtcat actttttttt cataaccgaa     660 gtgactttc cccaaacccg cttacaactt ttctaccccca tcaagcaatt taataataac     720 cgttttttt tgttcatgct acctcaattt gcttatgtac ctctttcaaa aactcccatg     780
tcctcccaaa aattctgatt tcagtctccc ccttaccttc atacatccca agcctttgc     840 catacattct ccgtttcaac ctaattgcgt gcttattatt catcctttgt atagcctttt     900
cagcttcatc aaaatttatt ggcccacctc atctcccaga actcatctca ggaattact     960 atgctccatt ttcagtaaaa acctcctcct ctctatgaac tacttgtctc ttgattactg    1020
ttatccaata ttatgtacct cattgaattt gccatcccca atccttttt ctttacctca     1080
```

```
aactcatttt ttctctccat actggcctat gactgtataa tgcgttctac ctccccaact    1140
gtccccaatt ctagttatgt accgttttc tacctcaaaa aattaaaccc cattatacaa    1200
ccgttccacc tcaaactccc                                                1220
```

<210> SEQ ID NO 63
<211> LENGTH: 1052
<212> TYPE: DNA
<213> ORGANISM: Caenorhabditis sp.

<400> SEQUENCE: 63

```
attttctctc tgtctcactt tctacctcca aacatatttt actacttgta ttgaatgcca     60
aaaaatacca tatttattaa ggagcattgt tcatttacag ttttgtactc tcagagcgtg    120
ttattatcta gaagcaattg tatactgttc tcagtacatg tagtacctcc cccagaatac    180
ttgtttctgt tactatgtac ccctcttatt aacttcggga tatgaaactt tttatgtttc    240
attttctatt gatttcattt gtttgtcatt ttcaagctcc tctttccaca taagctttaa    300
ctgcatgtct ttcatttta tttatttcta tttgccaatt gtttaactat gcacacattt    360
gtttcatgtt tctccagaga taactttccc aaattcaagt ttgcgccaac tcgtgctgct    420
cttttattgt acggttttat aacgtttccg tcttgaaatc agagattgta gccgtttttt    480
gaaaaggata tgccaaagaa tcgtccccca ccctctagtt gtcatttgtt aaatagccga    540
agtgacccaa caacccgctt ttgtcccctc tactaataac cgttttatta ttattatcac    600
tcaatattta tcttttatg tacttctttc actgctccca tgtcgtgatt tctgatttca    660
cattttccag actatctcgc actttcattc tacctcaata catcccagct ttttgccat    720 acattctccg attcgaattc atgtgtgctc gtttaactat tattacctgt atccaccgat    780
tacttttttg tttattcgct cccttttttc tatctcagga atgatttata gttttcaatt    840
tgtcttctca caactcatct aaactacttg tccgctacct tatgtacctc attgactcat    900
tttgccatca cccaatacaa tttataccct aatactgtct cttacctgta taatgccttc    960
tacctccaat ttttaccatc tattctagtt aattaccatt ttctacctca acccattttc   1020
tattatacaa ccgttccacc tcaaacttca gt                                  1052
```

<210> SEQ ID NO 64
<211> LENGTH: 23
<212> TYPE: RNA
<213> ORGANISM: Caenorhabditis sp.

<400> SEQUENCE: 64

```
gauuuuguau gagacgcauu ucg                                              23
```

<210> SEQ ID NO 65
<211> LENGTH: 72
<212> TYPE: DNA
<213> ORGANISM: Caenorhabditis sp.

<400> SEQUENCE: 65

```
tttcttttt tttccaaatc atcgtcactt atacaaaaac caaactccct tttaccgtta     60
aaccatgccc aa                                                          72
```

<210> SEQ ID NO 66
<211> LENGTH: 69
<212> TYPE: DNA
<213> ORGANISM: Caenorhabditis sp.

<400> SEQUENCE: 66

```
tttttctcta cttaaaaatc gtcacttata caaatccccc ccaaaacttc acccgttttc    60
tttattaaa                                                            69

<210> SEQ ID NO 67
<211> LENGTH: 23
<212> TYPE: RNA
<213> ORGANISM: Caenorhabditis sp.

<400> SEQUENCE: 67
gauuuuguau gagacgcauu ccg                                            23

<210> SEQ ID NO 68
<211> LENGTH: 21
<212> TYPE: RNA
<213> ORGANISM: Caenorhabditis sp.

<400> SEQUENCE: 68
gugcccguac ugugucggcu g                                              21

<210> SEQ ID NO 69
<211> LENGTH: 256
<212> TYPE: DNA
<213> ORGANISM: Caenorhabditis sp.

<400> SEQUENCE: 69
ctaccttttt tcttctcaat ctgttgtatg ggtaccaaat gttccggaac caaatgaaaa    60
tccccgcctt tctcgtcttt tgaagtccgt atcctccttg taatcttcca ccaccactcg   120
ccccagttct tgatctccgt taccgaatgt taaaacacgt gaatatgtaa ttgttttttg   180
tctcatcttc cgctcccccga aacctctttc atcacagccc cccaaattct cccagttagc   240
aacgggccca aacata                                                   256

<210> SEQ ID NO 70
<211> LENGTH: 293
<212> TYPE: DNA
<213> ORGANISM: Caenorhabditis sp.

<400> SEQUENCE: 70
ctaagtctta tttctctcaa ctttatgtat gggtacccct tttactggac acgaagaca    60 cattttcata catttttaa acttcgaatt ctgtggtcca tcttcccaa atcctcgccc    120 cgtttccgat ctctcttccg attatgtctc ctcgattttt aattttctt ccgatgtaaa   180 aaaaacccat caccacccag caaacctctt tcattcaaaa atttcatcaa ttttatcgtt   240 ttttttctctaa aatgtcactc tgtctctccc agttagcaac gggcaatttc att        293

<210> SEQ ID NO 71
<211> LENGTH: 21
<212> TYPE: DNA
<213> ORGANISM: Unknown
<220> FEATURE:
<223> OTHER INFORMATION: Bantam miR sequence

<400> SEQUENCE: 71
gtgagatcat tttgaaagct g                                              21

<210> SEQ ID NO 72
<211> LENGTH: 1441
<212> TYPE: DNA
<213> ORGANISM: Drosophila simulans
```

<400> SEQUENCE: 72

```
atgattatg tttatttgta atattttttg tcattgtttg ttcatcatca tattcaaatt     60
ggtctcacaa tataatagtt ttaagctcca cgcccaggag gttgatggca aaacgattga    120
aacttggcca gaagagagat agttttccca ttcgtacaca tcttttttgg aatgcacatt    180
aatgatctct cacaatggaa attaatgaaa attgatctcc gcagctagcc aaagttaaaa    240
aagaaatgaa gaggaaaaca tattttatag gcaactttca ctatatgcta gaatttccag    300
ggcgtttcaa tgctaatcga atacagtgac atgaaagcaa acatagcgaa atattaaga     360
aaatcaatca aaagaaaga aaaccaatt cccaaaaatc gcattgatct catggattta      420
tacaatacaa ttacatcaac cgttttttac aatgagaaat gttataaaaa gcagaaagtg    480
aaacacagaa acataaacaa aaattaacga aaagcttaga attaagttcg ccaagcgttt    540
tagttctact ttctagaatg tctaagtcgg tttagtgagt ttattgagct gtcttcggac    600
acaagtttac ttgtatatgt atataaagca atattatttg tgtagcctaa gtgacagtcc    660
caatcaaatc aaatccaatc caatatcacc cagtcccgga caattcccag caaaacaata    720
gactattttc gcgtacacat gtatcaatct taatttgaat taccacaaaa ccaagaaata    780
ctccaaccat acccaaatga aaaattattt ttgtaaattg tttgcatcaa gtgagcaggg    840
ggttaaacta aggaaccatc cttgctttat cctctgctta ttgctaatta gttttcacga    900
tgatctcggt aaagttttgt ggccttgcgc ccaaaagtcg taaagatttt tggtttgcca    960
taaatactcg aacaaaagt taagaaaaa cgaagcaaat ggaaaaaat cagaatgaaa       1020
cacaagaaat ttatattttt gacccaatgc tacttaatcc gttttttaat ttaagtatct    1080
ttactcgacc ttgtatatag cgcagttcga atcacagaat caaatgccat ttttgtatag    1140
aatttcgttt ggtgccaaaa cagtgacaga taattgtcta tgaacccgtg tatttcgcat    1200
attatacatt tatacatata tcgtaacttc aatgataagt ttgattctga aattttttgtc   1260
aactcaattt aagaaacatt tctgttgtag tttagtgatc gccggcagaa agcactttgt    1320
ttaattgtac atttttatatt atgctgtaat attttaatat acataaatat cattattgat    1380
ctcatgaata tgttcataag acaacaaaaa ttatatatat gaatacatct atgtgtatgt    1440
g                                                                    1441
```

<210> SEQ ID NO 73
<211> LENGTH: 1435
<212> TYPE: DNA
<213> ORGANISM: Drosophila erecta

<400> SEQUENCE: 73

```
atgattatg tttatttgta atattttttg tcattgtttg ttcatcatca tattcaaatt     60
ggtctcacaa tataatagtt ttaagctcca cgcccaggag gttgatggca aaacgattga    120
aacttggcca gaagagagat agttttccca ttcgtacaca gtcttttttg gaatgcacat    180
taatgatctc tcacaatgga aattaatgaa aattgatctc cgcagctagc caaagttaaa    240
aaagaaatga agaggaaaac atattttata ggcaattttc actatatgct agaatttccc    300
gggcgtttca tgctaatcg aatacagtga catgaaagca acatagcga aatattaag      360
aaaatcaatc aaaagaaag aaaaccaat tcccaaaaat cgcattgatc tcatggattt      420
atacaataca attacatcaa ccgttttttta caatgagaaa tgttataaaa agcagaaagt    480
gaaacacaga acataaaca aaattaacg aaaagcttag aattaagttc gccaagcgtt     540
ttagttctac tttctagaat gtctaagtcg gtttagtgag tttattacgc tgtcttcgga    600
```

```
cacaagttta cttgtatata aagcaatatt atttgtgtag cctaagtgac agtcccaatc      660
aaatccaagc caatccaata tcacccagtc ccggacattt cccagcaaaa caatagacta      720
ttttcgcgtt cacatgtatc aatcttaatt tgaattacca caaaacaatg aaatactaca      780
accataccca aatgaaaaat tattttttgta aattgtttgc atcaagtgag caggggatta     840
aattagggaa atatccttgc tttatcccct gcttattgct aattagtttt cacgatgatc      900
tcggtaaagt tttgtggcct tgcgcccaaa agtcgtacag atttttggtt tgccatgaaa      960
actcgaacaa aaagttaaag aaaaacgaag caaatggaaa aaaatcagaa tgaaacacaa     1020
gaaatttata tttttgaccc aatgctactt aatccgtttt ttaatttaag tatctttact     1080
cgaccttgta tatagcgcag ttcgaatcac agaatcaaat gccatttttg tatagaattt     1140
tgtttggtgc caaaacagtg acagataatt gtctatgaac ccgtgtattt cgcatattat     1200
acatttatac atatattgta acttcaatgc taagtttgat tctgaaattt tgtcgactca     1260
gtttaagaaa catttctgtt gtagtttagt gattgctagc agaaagcact ttgtttaatt     1320
gtacatttta tattatgctg taatatttta atatacataa atattattac tgatctcatg     1380
aatatgttca aagacaaca aaaattatat atatgaatac atctatgtgt atgtg           1435

<210> SEQ ID NO 74
<211> LENGTH: 1440
<212> TYPE: DNA
<213> ORGANISM: Drosophila melanogaster

<400> SEQUENCE: 74 atgatttatg тттаттттgta atattttttg tcattgtttg ttcatcatca tattcaaatt      60
ggtctcacaa tataatagtt ttaagctcca cgcccgggag attgatggca aaacgattga     120
aatttggcca gaagagagat agтттттcccc attcgtacac agтcттттттт ggaatgcaca     180

ttaatgatct ctcacaatgg aaattaatga aaattgatct ccgcagctag ccaaagttaa     240
aaaagaaatg aagaggaaaa catattctat aggcaatttt cactatatgc tagaatttcc     300
cgggcgtttc aatgctaatc gaatacagtg acatgaaagc aaacatagcg aaaatattaa     360
gaaaatcaat caaaagaaa gaaaaaccaa ttcccaaaaa tcgcattgat ctcatggatt     420
tatacaatac aattacatca accgттттттт tacaatgaga aatgttataa aaagcagaaa     480
gtgaaacaca gaaacataaa caaaaattaa cgaaaagctt agatataagt tcgccaagcg     540

ttttagttct атттttctaga atgtctaagt cggtttagtg agtttattaa gctgtcttcg     600 gacacaagtt таттттgtata taagcaatat таттттgтgта gcctaagtga cagtcccaat     660
caaatccaat ccaatatcac ccagtcccgg acatttccca gcaaaacaat agactattct     720
cgcgttcaca tgtatcaatc тттaатттgaa ttaccacaaa atgaaatgaa atactaaaac     780
catacacaaa tgaaaaatta tttttgtaaa ttgtttgcat caagtgagca aggggattag     840

ataaggaat catccttgct tatcccctg cttattgcta attagttttc acaatgatct     900
cggtaaagtt ttgtggcctt gcgcccaaaa agтcgтacaga ттттттggттт gccataaata     960 ctcgaacaaa aagttaatga aaacgaagc aaatggaaaa aaatcagaaa tgaaacacaa     1020
gaaatttata tttttgaccc aatgctactt aatccgtttt тgтaаттттаа gtatctttac     1080

tcgaccttgt atatagcgca gttcgaatca cagaatcaaa тgccaтттттт gтаtagaaттт     1140

ttatttggtg ccaaaacagt gacagataat taaatgtcta tgaacccgtg tatttcgcat     1200

attatacatt tatacatata tcgtaacttc aatgataagt tgattctga aattttgtca     1260
```

| actcaattta agaaacattt ctgttgtagt ttagtgattg ctagcagaaa gcactttgtt | 1320 |
| taattgtaca ttttatatta tgctgtaata ttttaatata cataaatatc attattgatc | 1380 |
| tcatgaatat gttcataaga caacaaaaat tatatatatg aatacatcta tgtgtatgtg | 1440 |

<210> SEQ ID NO 75
<211> LENGTH: 1436
<212> TYPE: DNA
<213> ORGANISM: Drosophila yakuba

<400> SEQUENCE: 75

| atgatttatg tttatttgta atatttttg tcattgtttg ttcatcatca tattcaaatt | 60 |
| ggtctcacaa tatataatag ttttaagctc cacgcccagg aggttgatgg caaaacgatt | 120 |
| gaaacttggc caggagagag atagttttcc cattcgtcac acagtctttt ttggaatgca | 180 |
| cattaatgat ctctcacaat ggaaattaat gaaaattgat ctccgcagct agccaaagtt | 240 |
| aaaaaagaaa tgatgaggaa acatatttt ataggcaatt ttcactatat gctagaattt | 300 |
| ccagggcgtt tcaatgctaa tcgaatacag tgacatgaaa gcaaacatag cgaaaatatt | 360 |
| aagaaaatca atcaaaaaga aagaaaaacc aattcccaaa aatcgcattg atctcatgga | 420 |
| tttatacaat acaattacat caaccgtttt ttacaatgag aaatgttata aaaagcagaa | 480 |
| agtgaaacac agaaacataa acaaaaatta acgaaaagct tagaattaag ttcgccaagc | 540 |
| gttttagttc tacatcttag aatgtctaag tcggtttagt gagtttatcg agctgtcttc | 600 |
| ggacacaagt ttacttgtat ataaagcaat attatttgtg tagcctaagt gacagtccca | 660 |
| atcaaatcaa atccaatcca atatcaccca gtcccggaaa aatcccagca aaacaataga | 720 |
| ctattttcgc gttcacatgt atcaatctta atttgacata ccacaaaaca aagaaatact | 780 |
| ccaaccacac ccaaatgaaa aattattttt gtaaattgtt tgcatcaaat gagcagggg | 840 |
| ttgaactaag gaaccatcct tgctttatcc cctgcttatt gctaattagt tttcacgatg | 900 |
| atctcggtaa agttttgtgg ccttgcgccc aaaagtcgta cagatttttg gtttgccata | 960 |
| aatactcgaa caaaaagtta agaaaaacg aagcaaatgg aaaaaaatca gaatgaaaca | 1020 |
| caagaaattt atatttttga cccaatgcta cttaatccgt tttttaattt aagtatcttt | 1080 |
| actcgacctt gtatatagcg cagttcgaat cacagaatca aatgccattt tgtatagaa | 1140 |
| ttttgtttgg tgccaaaaca gtgacagata attgtctatg aacccgtgta ttcgcatat | 1200 |
| tatacattta tacatatatc gtaacttcaa tgataagttt gattctgaaa ttttgtcaac | 1260 |
| tcaatttaag aaacatttct gttgtagttt agtgatttgc tagcagaaag cacttttgttt | 1320 |
| aattgtacat tttatattat gctgtaatat tttaatatat acataaatat cattactgat | 1380 |
| ctcatgaata tgttcataag acaacaaaaa ttatatatat gaatacatct atgtgt | 1436 |

<210> SEQ ID NO 76
<211> LENGTH: 1603
<212> TYPE: DNA
<213> ORGANISM: Drosophila pseudoobscura

<400> SEQUENCE: 76

| atgattagta tttttttttt gtaatatttt ttttgtcatt gttcatcatt gtcttcaaat | 60 |
| tggtctcaca atttagttgt ttaagtccca ggacccggga aatgtccagc cgggaaattg | 120 |
| tctgcccctg aaaaaggccg ccctctctcc gaaaatcttt tttggaacac gcacacaaat | 180 |
| gatctctccc aaatggaaat taatgcaagt tgatctccaa cgatagccaa agtcaaagga | 240 |
| aaaagtaatt caaacgaagg agaaggggaa agaccatgtt cagagggcaa cttccgattt | 300 |

| | | | |
|---|---|---|---|
| tgctggcgtt | ttctggccgt | ttcaatgcta | atcgaataca caacgtgaac atgaaagcga | 360 |
| aaatagtgaa | aaacaaaaaa | tcaaagaaa | ggtaaaaaca attcccaaaa atcgcattga | 420 |
| tctcatggat | ttatacaata | cacacagttt | tttttttaca atgagaaaaa aaatacaata | 480 |
| aaaaataaga | gaagaaaatg | aaaagtgaaa | cagaaacaga aacaaaaagg gaagagaaa | 540 |
| gagaaacgga | aaacggaaaa | caagagttaa | gtgtaagaaa agtctaggct taagttcgcc | 600 |
| aagcgtttta | gttctaaatt | caacagagtt | taaggtagat ttagtgagtt tttcacgcgt | 660 |
| ttattttgta | catacatata | cctaaagcaa | tattattctg tgtagccata agcgatagcc | 720 |
| cagacccca | gatacatgta | tacccagatt | ccagatccca gatcccagac tccatatcct | 780 |
| tatccactgc | cagccgcagc | cccagatata | catacataca ctttcaagca aaatagaaca | 840 |
| ctacacttct | caacttatga | actaatcatg | acacacacac acgcacacac acacaaacac | 900 |
| cacttccaaa | aacccaatga | aaaattaatt | ttgtaaattt gttgcatcaa atgaaccgga | 960 |
| aacggcggga | gcctgtcttc | ccctctggtt | cattgccaat tagttttcac aatgatctcg | 1020 |
| gtaaagttt | gtggcctcgc | agggcccaga | agtcaacatg gaaacattga tttctggcct | 1080 |
| gccatgaata | ctggaacaaa | aagttaaagg | aaagcagaag cagaagcaga agcagtagca | 1140 |
| gaagcagaat | cagaagcaaa | agcaaactat | attttgacc cgatgcgact tgatccgttt | 1200 |
| gttaaattta | agtatcttta | ctcgaccctg | tacatagcgc gcagttcgaa tcatagaatc | 1260 |
| aaatgccatt | tttgtataga | attttgtttg | gtgccaaaac agtgacagat aattgtctgc | 1320 |
| gacacacaca | cacacacaca | cacacacaca | cgcatacaca ttatacataa tagaatttat | 1380 |
| ttatcctaag | ctcgatccta | agttcaacaa | ttcagcaatt tgtcaattca attcaactta | 1440 |
| ggaaataatc | ctcttttttt | ttgttgtttt | tcgtgttcgg aagaagcgca agacttcgtt | 1500 |
| taattgtaca | ttttatatat | tatgctgtaa | tattttaata tgcataaata atatcattat | 1560 |
| tgatctcatg | aatatgttca | taagacaaaa | taagcagcaa caa | 1603 |

<210> SEQ ID NO 77
<211> LENGTH: 1568
<212> TYPE: DNA
<213> ORGANISM: Drosophila ananassae

<400> SEQUENCE: 77

| | | | |
|---|---|---|---|
| atgatttatg | tttaattgta | atttttttgtc | attgtttgtt catcatcatc ttcaaattgg | 60 |
| tctcacaatc | tagtagttaa | gccccccgccc | cagggagcga gttcgagcga ggttgaaaat | 120 |
| tcgcccagaa | atagcgatag | ggttatccca | ttctcagaca gtcttttttt ggaatgcaca | 180 |
| cgaatgatct | ctcacaatgg | aaattaatgg | aaattgatct ccgcacatag ccaaagtaaa | 240 |
| aaagaaatg | aaaaggaaac | cccctcattt | tcgtggcgat tttcaataat cactttcaga | 300 |
| gctccccagg | gcgtttcaat | gctaatcgat | taccgtgaca tgaaagcgaa catagcgaaa | 360 |
| atagtaagga | aaattaatca | aaaagaata | aataagaaag atagaaaaga aaaacaatt | 420 |
| cccaaaaatc | gcattgatct | catggattta | tttacattac aaatatttca accgttctt | 480 |
| acactgaaaa | gacaaatgtt | atgaaaagca | gaaagtgaaa agtgaaaaca gagaaacagt | 540 |
| aaacaaaaat | taatgaaaag | ctaatcttaa | gttcgcaaag cgttttagtt taagctttag | 600 |
| ttatagatta | aagtcgattt | agttcgtttt | ttgagctgtc tctgtatggc agtctctcct | 660 |
| tattattatt | attttttttt | tttgtatata | gagcaatatt atttgaatat gatataagtg | 720 |
| agataccact | taagtaccca | tcatcaaatc | caatccaatc ccagccagat cccagaccat | 780 |

```
gacacacaat gaaatagaat atgctttctc gtacatacct gcctatgtat taatcataat    840
ttgaattatc acaaacaaat caaaaacagt acaatacttc caaaacccca atgaaaaatt    900
atttttgtaa atttttttgc atcaaatgaa ccgggatggc caagacagtt taagattatt    960
tcttaaagct accttcctgg ttcattgcta attagttttc acaatgatct cggtaaagtt   1020
ttgtggccta gcgcccagaa gtcgacaaca agattttttgg ttgccataaa tactcgaaca   1080
aaaaagttag agaaaaacga agcaaaagga acaagtaaat cagaatacat gaaatttata   1140
tacatacgtt tcacccaatg cgacttaatc cgttttttgtt ttttattttgt aaatttaagt   1200
atctctactc gacctacttg tatatagtgc agttcgaatc atagaatcaa atgccatttt   1260
tttgtgtata gaattttgtt tggtgccaaa atatgaagag atatgagcgc gtatatttga   1320
atactatacc agtacatata atacatatat cgtaacttca atcatatagg tttcttgatt   1380
cgtcaatcca atttaagaat taatttctgt ttatgttttg tgttcttcgg aagcaggaaa   1440
atattgttta acttgtacat tttatattat gtggtaatat tttaatatac ataaatatca   1500
ttactgatct catgaatatg ttcataagac aacaacaatt ataaatatat ataaatatga   1560
ataaatct                                                             1568

<210> SEQ ID NO 78
<211> LENGTH: 1676
<212> TYPE: DNA
<213> ORGANISM: Drosophila virilis

<400> SEQUENCE: 78
ttagttaaat ttggtagtca gtaagcagga tatattttca tgaggattat tttgttcatt     60
cttcaaattg gtctcacaat ttagttatta agcaacattg ttcaagaaat ttgcgcaaaa    120
tgtccattga aatagtccaa agcttcacga cacgttttca ggtttacctt tggttaacac    180
tcaaagccaa gcgttgaatg atctcttaac tggaaattta tagagggcgc aactcaattg    240
atctccatag ctagccaaag tcaaaagtca acacacgcag caaatcaaat ttttgtttgt    300
tttttttatt atttttttggt aagtttcaaa gcattttgcc aaatttcttg acgtttcaat    360
gctaatcgaa cagtgaaaaa atagtaagga atttaaagag caaaaaataa ttaagaaaat    420
gaacatatta aagaaaaga aaatgaaaa acaaaaaaaa aaaactatt cccaaaaatc    480
gcattgatct catggatttt ttttatcatt tacatcagca attttttact tgcattaaac    540
gcgatgagaa atatgtacat taggcataat tatgtaaaag tttaggttta gaatcgccaa    600
gcgttttagt ttacatattc atagccttaa gtttcttttta tgtaaagttt tccgcttgtc    660
attcgacaaa tcaaagcaat tcaaatctaa gtaaatgtat tgtttatcat atgttaaatg    720
cctgtaagta gagcaatatt ttttggtagc ttaagagtta ttcatttttac agacgagata    780
cagagagaaa gggagagttg cccacacata cactagttaa tataacagca gcaagcagca    840
aaggtagaca aaatttgttt attatgattt tttcttacgt attttttttt tatacacata    900
cccataattt gtaaacaact attccacaca cccaaaaaca aaacaaaaa aaaaaaaaa    960
acaaaaacga aaaaaatcac aaaaaatcta tgaaaatttt tgtaaatttt tctaaaatga   1020
actcaacgca aagttgtcat tggccagcaa aattgttgtg ttttgttgcc agtgcccagc   1080
gccagcgatg gttcattcta attagttttc acaatgatct cggtaaagtt ttgtggccgc   1140
gcgcccaaaa gtcaacaaga ttttggttg ccataaactg aaacaaggca gaaaagcaag   1200
aaacaaaaat aaaatgaatc acatagcgaa aatttgttta ttttattcca tgcgaacttc   1260
cgacattaaa ttaagtaatt cgtaatttgt atatagcgca aaaatcaaat gccattttgt   1320
```

```
atagattgtt ggtgccaaaa cagtgaaaat gtgtgttaaa tatgtgctgc caattttttct    1380 tattgaaagc tgcgatgaac acatattcaa acttacataa cttcaattac gtttagactt    1440
aagtccccat tattttcaat atgtattctt aaataaaaat gcatatatca atatgtgtta    1500
ttctttgtgt aaagctcaag cgaacgcaca tatatcttgt acattttatc ttatgctgta    1560
ataatttaat atatataaag atatatgtat atatatatat cttatatcac tatgatctca    1620
tgaatatgtt cataagacaa aagtatatat gtaaatgaaa acaatacaa aacgca         1676
```

<210> SEQ ID NO 79
<211> LENGTH: 1832
<212> TYPE: DNA
<213> ORGANISM: Drosophila mojavensis

<400> SEQUENCE: 79

```
ttagttaaat ttgttagtca gtaagctttg attttttcaag tggattacat tttgttcatt    60
cttcaaattg gtctcacaat ctagttttaa gcacacattg tacaagaaat ttgcgcaaca    120
attgaaattt accaaaagca acgggaaagg gtggacgaaa cattttcagg tttatctttg    180
gttaacacac tcaaagccaa gcgttgaatg atctctaaaa actggaaatt tatagaacac    240
tcaattgatc tccacagcta gccaaagtca aaagtcaaac acacacacat acacacacat    300
gcagcaaatc aaatttatat ttatgtcccc tttctgtatt tttggtaact tttggtaaat    360
ttcaatttca gttttgccta aatttcttga cgtttcaatg ctaatcgaac agtggaaaac    420 aaaaatacccg aaatgaaaac aaaataaaaa tatattagaa aattaacata tgaaaagaaa    480
aagaaaaaaa actattccca aaaatcgcat tgatctcatg gatttttta tcatttacat    540 cagcaatttt ttacttgcat tgagaaaata ttattgtaaa agtctagggt taagatcgcc    600
aagcgtttta gtttacatat ttcttaacac taagttttta tgtctaaagt taaatgcaaa    660
aaaaaaaaaa aacacaaaa aaaaaaacac taaaaaaaaa aaaaaatca aaaacttaaa    720 aaatatggga aaaaatgtac atcgaatcta agtaaatgta tttgtttatc atatgttaaa    780
tgcctgtaag tagcgcaata ttttttgtta gctttaagat aaaatcattt cgcagacggc    840
aaaggcaaag aaagggacgt aaagagttag agaaagagag agagagagag aagatacact    900
agttaatgta aacgcagcaa gcagcaaaag tagagaaaat tttgtttaat attcatgttt    960
ttttttctta cgtatttttt tttttttttt attattatac atacttacat ttaatttgta    1020
tacaactatt ccaagccccc aacccaaaaa aaaaaaaaa caaacaaca aaaaactcaa    1080 tgaaaatttt tgtaaatttt tctaaaatga actcaacgca aatattctgt caccgaccgc    1140
agcgaaggag caatttgcat tgctctttgc cttgggagtg gcagaagttg cgccgattc    1200 attctaatta gttttcacat tgatctcggt aaagttttgt ggccgcgcgc ccagaagtca    1260
tcaagatttt tggttgccat aaactgaagc aaggcagaaa gaacaagcaa gaaacaaaat    1320
atatatcaaa tgaatcacat agcgacaaat ttttgtttta ttttctattc catgcgacgt    1380
acttccgacc taaaattaag taattcgtaa attcgtaact cgtaatttgt aatttgtata    1440
tatcgcaaaa atcgaaatgc catttttttgt atagatcgtt ggtgccaaaa cagttgaatt    1500
gtgtgttaaa cagtgtagga tggagctgcc agcaacggga gttcgcattg agagctgcca    1560
tcgtaacact tacgcattcg attcaaaact cccaattata aatagagtta agctcccct    1620 taaaatatttt tcaatatgta ttttttctgtg tgtgggaaca caacatttat acaacttgta    1680
cattttatct tatgctgtaa tttaatatat atatatatat atatatatat ataaaaaga    1740
```

-continued atatataaat atataaaata tcactatgat ctcatgaata tgttcataag acgaaagtat    1800
atatgtaaat taaataaata cgcataaata ta                                  1832

<210> SEQ ID NO 80
<211> LENGTH: 22
<212> TYPE: RNA
<213> ORGANISM: Unknown
<220> FEATURE:
<223> OTHER INFORMATION: miR-196b sequence

<400> SEQUENCE: 80
uagguaguuu cauguuguug gg                                             22

<210> SEQ ID NO 81
<211> LENGTH: 44
<212> TYPE: RNA
<213> ORGANISM: Homo sapiens

<400> SEQUENCE: 81
uucugcuaag uucucccaac aacaugaaac ugccuauuca cgcc                     44

<210> SEQ ID NO 82
<211> LENGTH: 44
<212> TYPE: RNA
<213> ORGANISM: Mus musculus

<400> SEQUENCE: 82
uucugcuaag uuucccaac aacaugaaac ugccuauuca cgcc                      44

<210> SEQ ID NO 83
<211> LENGTH: 44
<212> TYPE: RNA
<213> ORGANISM: Rattus norvegicus

<400> SEQUENCE: 83
uucugcuaag uuucccaac aacaugaaac ugccuauuca cgcc                      44

<210> SEQ ID NO 84
<211> LENGTH: 44
<212> TYPE: RNA
<213> ORGANISM: Xenopus laevis

<400> SEQUENCE: 84
aaaacaaaag acaaaccaac aacaugaaac ugccuaauug agau                     44

<210> SEQ ID NO 85
<211> LENGTH: 42
<212> TYPE: RNA
<213> ORGANISM: Danio rerio

<400> SEQUENCE: 85
aaauuacuga cuuccaacaa caugaaacug ccuauuuaug cc                       42

<210> SEQ ID NO 86
<211> LENGTH: 44
<212> TYPE: RNA
<213> ORGANISM: Takifugu sp.

<400> SEQUENCE: 86
caauuaauga aauuccaac aacaugaaac ugccuauuua ugcc                      44

<210> SEQ ID NO 87
<211> LENGTH: 22

```
<212> TYPE: RNA
<213> ORGANISM: Unknown
<220> FEATURE:
<223> OTHER INFORMATION: miR-375 sequence

<400> SEQUENCE: 87
uuuguucguu cggcucgcgu ga                                          22

<210> SEQ ID NO 88
<211> LENGTH: 84
<212> TYPE: DNA
<213> ORGANISM: Mus musculus

<400> SEQUENCE: 88
aagtatccta gttcatgtac atccgaatgc taactaatac tgtgtttaag tttcgtgttg    60
caagaacaaa tggaataaac ttga                                          84

<210> SEQ ID NO 89
<211> LENGTH: 84
<212> TYPE: DNA
<213> ORGANISM: Rattus norvegicus

<400> SEQUENCE: 89
aagtatccta gttcatgtac atccgaatgc taactaatac tgtgtttaag tttcgtgttg    60
caagaacaaa tggaataaac ttga                                          84

<210> SEQ ID NO 90
<211> LENGTH: 82
<212> TYPE: DNA
<213> ORGANISM: Gallus gallus

<400> SEQUENCE: 90
tatcatggtt catagacatc agaatgcaaa atgatactgt attttaagt ttgtgttgca     60 agaatgaatg gaataaactt ga                                            82

<210> SEQ ID NO 91
<211> LENGTH: 81
<212> TYPE: DNA
<213> ORGANISM: Bos taurus

<400> SEQUENCE: 91
tatcctagtt catgtacatc agaatgctaa ataatactgt gtttaagttt tgtgttgcaa    60
gaacaaatgg aataaacttg a                                             81

<210> SEQ ID NO 92
<211> LENGTH: 85
<212> TYPE: DNA
<213> ORGANISM: Homo sapiens

<400> SEQUENCE: 92
aagtatccta gttcatgtac atccgaatgc taaataatac tgtgttttaa gttttgtgtt    60
gcaagaacaa atggaataaa cttga                                         85

<210> SEQ ID NO 93
<211> LENGTH: 85
<212> TYPE: DNA
<213> ORGANISM: Pan troglodytes

<400> SEQUENCE: 93
aagtatccta gttcatgtac atccgaatgc taaataatac tgtgttttaa gttttgtgtt    60
```

```
gcaagaacaa atggaataaa cttga                                            85

<210> SEQ ID NO 94
<211> LENGTH: 94
<212> TYPE: DNA
<213> ORGANISM: Xenopus laevis

<400> SEQUENCE: 94
taatattttg ttaataggct tcctataatc gccagtagct cctccggcca cactcgcatt     60
catgtcaata acaagaaggc tgaattaaat ctga                                  94

<210> SEQ ID NO 95
<211> LENGTH: 96
<212> TYPE: DNA
<213> ORGANISM: Danio rerio

<400> SEQUENCE: 95
gaatttccct tcactccgct tccctcctcc agcgctccga cattcccgtc acattgtaga     60
tgctcaaaga acaaatatta gacttcagac gctcga                                96

<210> SEQ ID NO 96
<211> LENGTH: 34
<212> TYPE: RNA
<213> ORGANISM: Danio rerio

<400> SEQUENCE: 96
gacauuggau auugaggaa aaaccauucc auuu                                   34

<210> SEQ ID NO 97
<211> LENGTH: 43
<212> TYPE: RNA
<213> ORGANISM: Gallus gallus

<400> SEQUENCE: 97
aaauguggau auugaagga gagggaaaa aagcauucca uag                          43

<210> SEQ ID NO 98
<211> LENGTH: 33
<212> TYPE: RNA
<213> ORGANISM: Sus scrofa

<400> SEQUENCE: 98
aaaaguggau auugaagaa aagcauucca uau                                    33

<210> SEQ ID NO 99
<211> LENGTH: 33
<212> TYPE: RNA
<213> ORGANISM: Mus musculus

<400> SEQUENCE: 99
aaagguggau auugaagaa aagcauucca uau                                    33

<210> SEQ ID NO 100
<211> LENGTH: 32
<212> TYPE: RNA
<213> ORGANISM: Rattus norvegicus

<400> SEQUENCE: 100
aaaguggaua uugaagaaa agcauuccau au                                     32

<210> SEQ ID NO 101
<211> LENGTH: 32
```

```
<212> TYPE: RNA
<213> ORGANISM: Pan troglodytes

<400> SEQUENCE: 101
aaaguggaua uuugaagaaa agcauuccau au                                    32

<210> SEQ ID NO 102
<211> LENGTH: 32
<212> TYPE: RNA
<213> ORGANISM: Homo sapiens

<400> SEQUENCE: 102
aaaguggaua uuugaagaaa agcauuccau au                                    32

<210> SEQ ID NO 103
<211> LENGTH: 38
<212> TYPE: RNA
<213> ORGANISM: Canis lupus familiaris

<400> SEQUENCE: 103
gcgccgccaa uaugcacugu acauuccaca agcauugc                              38

<210> SEQ ID NO 104
<211> LENGTH: 38
<212> TYPE: RNA
<213> ORGANISM: Xenopus laevis

<400> SEQUENCE: 104
aucaccccaa uaugcacugu acauuccaca agcauugc                              38

<210> SEQ ID NO 105
<211> LENGTH: 38
<212> TYPE: RNA
<213> ORGANISM: Gallus gallus

<400> SEQUENCE: 105
ccuuccaaau uaugcacugu acauuccaca agcauugc                              38

<210> SEQ ID NO 106
<211> LENGTH: 38
<212> TYPE: RNA
<213> ORGANISM: Macropus eugenii

<400> SEQUENCE: 106
gcccugccaa uaugcacugu acauuccaca agcauugc                              38

<210> SEQ ID NO 107
<211> LENGTH: 38
<212> TYPE: RNA
<213> ORGANISM: Bos taurus

<400> SEQUENCE: 107
gcgccgccag uaugcacugu acauuccaca agcauugc                              38

<210> SEQ ID NO 108
<211> LENGTH: 38
<212> TYPE: RNA
<213> ORGANISM: Mus musculus

<400> SEQUENCE: 108
gcgccgccaa uaugcacugu acauuccacg agcauugc                              38

<210> SEQ ID NO 109
```

```
<211> LENGTH: 38
<212> TYPE: RNA
<213> ORGANISM: Rattus norvegicus

<400> SEQUENCE: 109
gcgccgccaa uaugcacugu acauuccacg agcauugc                               38

<210> SEQ ID NO 110
<211> LENGTH: 38
<212> TYPE: RNA
<213> ORGANISM: Pan troglodytes

<400> SEQUENCE: 110
gcgccgccaa uaugcacugu acauuccaca agcauugc                               38

<210> SEQ ID NO 111
<211> LENGTH: 38
<212> TYPE: RNA
<213> ORGANISM: Homo sapiens

<400> SEQUENCE: 111
gcgccgccaa uaugcacugu acauuccaca agcauugc                               38

<210> SEQ ID NO 112
<211> LENGTH: 42
<212> TYPE: RNA
<213> ORGANISM: Mus musculus

<400> SEQUENCE: 112
gggcauuucc cccaaugaaa uauacaagua aacauuccaa ca                          42

<210> SEQ ID NO 113
<211> LENGTH: 42
<212> TYPE: RNA
<213> ORGANISM: Equus caballus

<400> SEQUENCE: 113
gggcauuccc cccaaugaaa uacacaagua aacauuccaa ca                          42

<210> SEQ ID NO 114
<211> LENGTH: 42
<212> TYPE: RNA
<213> ORGANISM: Pan troglodytes

<400> SEQUENCE: 114
gggcguuucc cccaaugaaa uacauaagua aacauuccaa ca                          42

<210> SEQ ID NO 115
<211> LENGTH: 42
<212> TYPE: RNA
<213> ORGANISM: Homo sapiens

<400> SEQUENCE: 115
gggcguuucc cccaaugaaa uacacaagua aacauuccaa ca                          42

<210> SEQ ID NO 116
<211> LENGTH: 39
<212> TYPE: RNA
<213> ORGANISM: Sus scrofa

<400> SEQUENCE: 116
gggcauuucc cccagugaaa uauacaagua aacauucca                              39
```

```
<210> SEQ ID NO 117
<211> LENGTH: 38
<212> TYPE: RNA
<213> ORGANISM: Capra hircus

<400> SEQUENCE: 117
gggcauuucc cccaaugaaa uaaguaaaca uuccaaca                                   38

<210> SEQ ID NO 118
<211> LENGTH: 38
<212> TYPE: RNA
<213> ORGANISM: Bos taurus

<400> SEQUENCE: 118
gggcauuucc cccaaugaaa uaaguaaaca uuccaaca                                   38

<210> SEQ ID NO 119
<211> LENGTH: 38
<212> TYPE: RNA
<213> ORGANISM: Ovis aries

<400> SEQUENCE: 119
gggcauuucc cccaaugaaa uaaguaaaca uuccaaca                                   38

<210> SEQ ID NO 120
<211> LENGTH: 41
<212> TYPE: RNA
<213> ORGANISM: Struthio camelus

<400> SEQUENCE: 120
gggcauucuc ccagugaaca augcaacuaa acauuccaau a                               41

<210> SEQ ID NO 121
<211> LENGTH: 41
<212> TYPE: RNA
<213> ORGANISM: Gallus gallus

<400> SEQUENCE: 121
gggcauucuc ccacugaaca augcaacuaa acauuccaau a                               41

<210> SEQ ID NO 122
<211> LENGTH: 41
<212> TYPE: RNA
<213> ORGANISM: Xenopus laevis

<400> SEQUENCE: 122
gggcauucuc ccucuaaaca auucaaauac acauuccaau g                               41
```